United States Patent [19]
Sanechika et al.

[11] Patent Number: 5,547,593
[45] Date of Patent: Aug. 20, 1996

[54] LUBRICANT OIL COMPOSITION COMPRISING A FLUORINE-CONTAINING AROMATIC COMPOUND AND AN ALKYL- OR ALKYL DERIVATIVE-SUBSTITUTED AROMATIC COMPOUND, AND A REFRIGERANT COMPOSITION CONTAINING THE SAME

[75] Inventors: Kenichi Sanechika, Nobeoka; Hiroyuki Fukui; Masanori Ikeda, both of Fuji, all of Japan

[73] Assignee: Asahi Kasei Kogyo Kabushiki Kaisha, Osaka, Japan

[21] Appl. No.: 289,220

[22] Filed: Aug. 11, 1994

[30] Foreign Application Priority Data

Aug. 11, 1993 [JP] Japan .................................. 5-199527

[51] Int. Cl.$^6$ .............................................. C10M 131/10
[52] U.S. Cl. .................... 508/207; 568/641; 568/655; 508/257; 508/435; 508/441; 508/549; 508/550; 508/556; 508/561; 508/568; 508/570; 508/580
[58] Field of Search ........................... 252/58, 54, 48.8

[56] References Cited

U.S. PATENT DOCUMENTS

| | | | |
|---|---|---|---|
| 4,359,394 | 11/1982 | Gainer et al. | 252/58 |
| 4,405,529 | 9/1983 | Siddens et al. | 260/465 F |
| 4,753,745 | 6/1988 | Kostusyk et al. | 252/58 |
| 4,755,316 | 7/1988 | Magid et al. | 252/68 |
| 4,880,553 | 11/1989 | Kostusyk et al. | 252/58 |
| 4,897,211 | 1/1990 | Dekura et al. | 252/58 |
| 4,990,418 | 2/1991 | Mukoh et al. | 430/56 |
| 5,096,606 | 3/1992 | Hagihara et al. | 252/68 |
| 5,254,274 | 10/1993 | Ho et al. | |
| 5,294,356 | 3/1994 | Tanaka et al. | 252/56 R |
| 5,326,486 | 7/1994 | Mizui et al. | 252/46.6 |

FOREIGN PATENT DOCUMENTS

| | | |
|---|---|---|
| 0406479 | 1/1991 | European Pat. Off. |
| 0432273 | 6/1991 | European Pat. Off. |
| 0528043 | 2/1993 | European Pat. Off. |
| 0556662 | 8/1993 | European Pat. Off. |
| 0557796 | 9/1993 | European Pat. Off. |
| 246788 | 6/1987 | Germany . |
| 60-96684 | 5/1985 | Japan . |
| 1-118598 | 5/1989 | Japan . |
| 2245587 | 1/1992 | United Kingdom . |

OTHER PUBLICATIONS

English language abstract of Japanese Patent No. 58171487.

*Primary Examiner*—Ellen M. McAvoy
*Attorney, Agent, or Firm*—Birch, Stewart, Kolasch & Birch, LLP

[57] ABSTRACT

Disclosed is a lubricant oil composition comprising: (A) a fluorine-containing aromatic compound, and (B) an alkyl- or alkyl derivative-substituted aromatic compound having a kinetic viscosity of from 0.1 to 500 cSt as measured at 40 ° C., wherein:

the compound (A) is represented by the formula:

$$R(XR_f)_n \qquad (A)$$

wherein X represents an oxygen or a sulfur atom; n is an integer of from 1 to 4; R represents an n-valent, unsubstituted or substituted aromatic group having from 6 to 60 carbon atoms; and $R_f$ represents an unsubstituted or partially substituted fluorocarbon group having from 1 to 25 carbon atoms; and the compound (B) comprises at least one substituted aromatic nucleus, wherein a substituent is an unsubstituted or substituted alkyl group having from 1 to 30 carbon atoms, or a derivative thereof. The lubricant oil composition having a kinetic viscosity of from 2 to 500 cSt as measured at 40° C. The lubricant oil composition exhibits not only excellent miscibility with hydrofluorocarbon refrigerants and hydrofluoroether refrigerants over a wide temperature range, but also satisfy all requirements of properties for use thereof as a lubricant in refrigeration equipment, that is, low temperature fluidity, low moisture absorption properties, high electrical insulation, prolonged durability, and excellent lubricating properties.

34 Claims, 2 Drawing Sheets

5,547,593

LUBRICANT OIL COMPOSITION COMPRISING A FLUORINE-CONTAINING AROMATIC COMPOUND AND AN ALKYL- OR ALKYL DERIVATIVE-SUBSTITUTED AROMATIC COMPOUND, AND A REFRIGERANT COMPOSITION CONTAINING THE SAME

BACKGROUND OF THE INVENTION

1. Field of the Invention

The present invention relates to a lubricant oil composition. More particularly, the present invention is concerned with a lubricant oil composition for use in a refrigeration system, specifically a refrigeration system in which, from the viewpoint of the environmental protection, substitute refrigerants are used for chlorine-containing refrigerants, such as CFC-12 (1,1-dichloro- 1,1-difluoromethane) and HCFC-22 (chlorodifluoromethane), which are likely to destroy the ozone layer. Examples of substitute refrigerants include: (1) fluoroalkanes, particularly lower hydrocarbons having 1 to 5 carbon atoms, such as HFC-134a (1,1,1,2-tetrafluoroethane), HFC-134 (1,1,2,2-tetrafluoroethane), HFC-152a (1,1-difluoroethane), HFC-32 (difluoromethane), HFC-125 (pentafluoroethane), HFC-143a (1,1,1-trifluoroethane) and HFC-227ea (1,1,1,2,3,3,3-heptafluoropropane), which do not damage the ozone layer; (2) hydrofluoroethers (HFE) (hereinafter frequently referred to simply as "HFE"), which do not damage the ozone layer and, in addition, are expected to lower the GWP (Global Warming Potential); (3) mixtures of the refrigerants mentioned under (1) and (2) above.

2. Discussion Of Related Art

CFC-12 is still currently, widely used as a refrigerant in refrigeration equipment for car air conditioners and refrigerators, while HCFC-22 is widely used as a refrigerant in refrigeration equipment for room air conditioners. However, development of a refrigerant which can be used in substitution for chlorine-containing refrigerants, such as CFC-12 and HCFC-22, has been desired from the viewpoint of the protection of the ozone layer.

As substitute refrigerants, the above-mentioned lower hydrofluorocarbons having 1 to 5 carbon atoms are promising. Of these, hydrofluorocarbons having 1 to 2 carbon atoms are particularly preferred.

In conventional refrigeration systems using CFC-12 or HCFC-22, mineral oil or alkylbenzene is used as a lubricant for a compressor of the refrigeration system. CFC-12 and HCFC-22 exhibit high oleophilicity since they contain chlorine atoms, so that they are miscible with mineral oil and alkylbenzene over a wide temperature range. Accordingly, even in the refrigeration systems where evaporation and condensation of the refrigerant are repeated, phase separation of CFC-12 or HCFC-22 as the refrigerant from the lubricant does not occur.

However, various types of hydrofluorocarbon refrigerants (hereinafter frequently referred to simply as "HFC refrigerants") and HFE refrigerants are not satisfactorily miscible with hydrocarbon compounds, such as mineral oil and alkylbenzene, since such refrigerants contain no chlorine atom. Therefore, when a hydrocarbon compound, such as mineral oil or alkylbenzene, is used as a lubricant, various serious problems occur. For example, because the lubricant is replaced by the refrigerant in a compressor, the lubrication becomes unsatisfactory. And the lubricant adheres to the inner wall of the heat exchanger, leading to a lowering of the heat exchange efficiency.

A lubricant for use in refrigeration equipment employing, as a refrigerant, a hydrofluorocarbon (HFC) such as HFC-134a, and a hydrofluoroether (HFE), should be miscible with either HFC or HFE at least over a temperature range from 0° C. to 50° C., preferably over a range from –20° C. to 70° C., more preferably over a range from –40° C. to 90° C., and most preferably over a still wider temperature range.

Various polyalkylene glycol compounds, polyol ester compounds and polycarbonate compounds have been proposed as lubricants highly miscible with hydrofluorocarbons, such as HFC-134a, for use in combination with such hydrofluorocarbons. For example, polyalkylene glycols having at least two hydroxyl groups (especially, polyoxypropylene glycol) disclosed in the specification of U.S. Pat. No. 4,755,316, are described as exhibiting a good miscibility with hydrofluorocarbons, such as HFC-134a, over a wide temperature range. However, the temperature range over which polyalkylene glycols are miscible with HFC-134a is still unsatisfactory for their functioning as lubricants, and improvement of the miscibility, especially at high temperatures, is required.

Polyoxalkylene glycols have not only unsatisfactory lubricating properties under application conditions, but also high moisture absorption (or water absorption) properties. Therefore, various problems are likely to arise, such as corrosion of metals, and lowering of a volume resistivity (a lowering of a volume resistivity causes a problem in the case of a closed type refrigeration equipment, such as a refrigerator.) Accordingly, polyoxyalkylene glycols are not good lubricants for a refrigeration system from a practical point of view.

Polyol ester compounds, disclosed in Japanese Patent Application Laid-Open Specification Nos. 3- 128991 and 3-179091 and polycarbonate compounds in Nos.5-32688 and 5-86391, are generally considered to be also highly miscible with HFC-134a. However, since such compounds exhibit high moisture absorption properties due to the polar groups contained therein, a problem in durability in terms of hydrolysis resistance is caused.

In addition to the above-mentioned polyalkylene glycol and polyol ester oils, fluorine-containing oils are considered to be lubricants miscible with fluoroalkanes, such as HFC-134a.

With respect to the fluorine-containing oils, the following patent application publications are noted.

In Japanese Patent Application Laid-Open Specification No. 60-96684, it is taught that when a fluorolubricant oil, such as a fluorinated silicone or a perfluoropolyether, is used in a fluorocarbon working medium for a heat pump or the like, the heat resistance of the fluorocarbon working medium is improved. However, no description is made therein with respect to the miscibility of the lubricant oil with a hydrofluoroalkane to be used as a working medium.

Japanese Patent Application Laid-open Specification No. 1-118598 describes the use of fluorocompounds, such as a perfluoropolyether and a fluorinated silicone, as a lubricant for fluorocarbon refrigerants. However, no description is made therein with respect to the miscibility of such fluorocompounds with a hydrofluoroalkane at low temperatures below room temperature. Further, no description is made therein with respect to the miscibility of fluorocompounds, other than a perfluoropolyether and a fluorinated silicone, with a hydrofluoroalkane.

The present inventors previously examined the miscibilities of perfluoropolyethers having various structures indicated below, inclusive of perfluoropolyethers (trade name: Fomblin Y-06, Y-25 and Y-45, manufactured and sold by Nippon Montedison Co., Ltd., Japan) employed in Examples of Japanese Patent Application Laid-Open Specification Nos. 60-96684 and 1- 118598, with a fluoroalkane, such as HFC-134a, HFC-134 and HFC-152a.

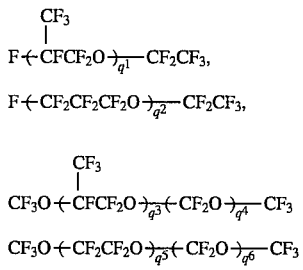

wherein each of $q^1$, $q^2$, $q^3$, $q^4$, $q^5$ and $q^6$ is a positive integer.

As a result, it was found that there were cases where miscibilities were observed at temperatures as high as about room temperature or more, but in any case, miscibilities were unsatisfactory at low temperatures. Accordingly, it was confirmed that such perfluoropolyethers were not suitable as a lubricant for use in refrigeration equipment employing a fluoroalkane, such as HFC-134a, HFC-134 and HFC-152a, as a refrigerant. Moreover, because such perfluoropolyethers are not miscible with various types of hydrocarbon oils, such as alkylbenzene and mineral oil, the perfluoropolyethers cannot also be used in the form of a mixed lubricant thereof with the above-mentioned hydrocarbon oils, for use in refrigeration equipment employing a hydrofluorocarbon refrigerant.

On the other hand, in EP 0 528 043 A1, it is described that the fluorine-containing aromatic compound represented by formula $R(XR_f)_n$, the definition of which is substantially the same as that of formula (A) hereof, exhibits excellent miscibility with HFC refrigerants, while exhibiting desirable characteristics, such as satisfactory heat resistance, lubricating properties and durability. It is also described therein to the effect that the compound of formula $R(XR_f)_n$ can be used in the form of mixtures with other oils; that the other lubricant oil usable in combination with the above compound is generally selected from those miscible with a fluoroalkane refrigerant to a certain degree, and more particularly, the other lubricant oil is selected from the group consisting of perfluoropolyether oils, perfluoropolyether oils having a carbonyl-containing group, such as a carboxyl group, a carboxylate group, an amido group, a ketone group and an ester group, or having a polar group, such as a hydroxyl group, an amino group, an imido group, an ether group, a benzoimidazol group, a phosphite group, a phosphine group, a nitrile group, a phosphotriazine group and a triazine group, chlorofluorocarbon oils, polyalkylene glycol oils, ester oils and fluorinated silicone oils; and that appropriate types of oils are selected from these oils, taking into consideration the miscibility thereof with the compound $R(XR_f)_n$ and the viscosity and lubrication characteristics of the resultant lubricating composition. However, in EP 0 528 043 A1, there is no description with respect the miscibility of the these mixtures (mixed oils) with HFC refrigerants.

In these situations, the present inventors have made extensive and intensive studies with a view toward further improving the properties of the lubricant having the structure disclosed in EP 0 528 043 A1 in order to provide a practically further improved lubricant exhibiting not only excellent miscibility with HFC refrigerants, such as HFC-134a, and HFE refrigerants over a wide temperature range, but also satisfying all requirements of properties for use thereof as a lubricant in refrigeration equipment, that is, low temperature fluidity, low moisture absorption properties, high electrical insulation, prolonged durability, excellent lubricating properties, high safety, such as low bioaccumulation (bioconcentration), and low cost.

As a result, it has surprisingly, unexpectedly been found that when the fluorine-containing aromatic compound (A) represented by formula $R(XR_f)_n$ as defined herein is mixed with a specific alkyl- or alkyl derivative-substituted aromatic compound (B) as defined herein, the resultant lubricant oil composition exhibits very excellent properties, such as high miscibility with HFC and HFE refrigerants over a wide temperature range, low temperature fluidity, low moisture absorption properties, and high electrical insulation, as compared to the compound (A) alone, without impairing the inherent excellent properties of the compound (A), such as high heat resistance, high hydrolysis resistance, and low bioaccumulation (bioconcentration). In this connection, it should be noted that the alkyl- or alkyl derivative-substituted aromatic compound (B) is available at low cost, so that the mixing of compound (A) with such a cheap compound (B) leads to a cost reduction, bringing about great advantages from a practical point of view.

The present invention has been completed, based on such novel findings.

SUMMARY OF THE INVENTION

It is therefore an object of the present invention to provide a novel lubricant oil composition exhibiting not only excellent miscibility with HFC refrigerants such as HFC-134a, and HFE refrigerants over a wide temperature range, but also satisfying requirements of properties for use thereof as a lubricant in refrigeration equipment, that is, low temperature fluidity, low moisture absorption properties, high electrical insulation, prolonged durability, excellent lubricating properties, high safety, such as low bioaccumulation (bioconcentration), and low cost.

It is another object of the invention to provide a refrigerant composition comprising the above-mentioned novel lubricant oil composition and the refrigerant, such as an HFC refrigerant and an HFE refrigerant.

The foregoing and other objects, features and advantages of the present invention will become apparent from the following detailed description and appended claims, taken in connection with the accompanying drawings.

DETAILED DESCRIPTION OF THE INVENTION

Figure 1:
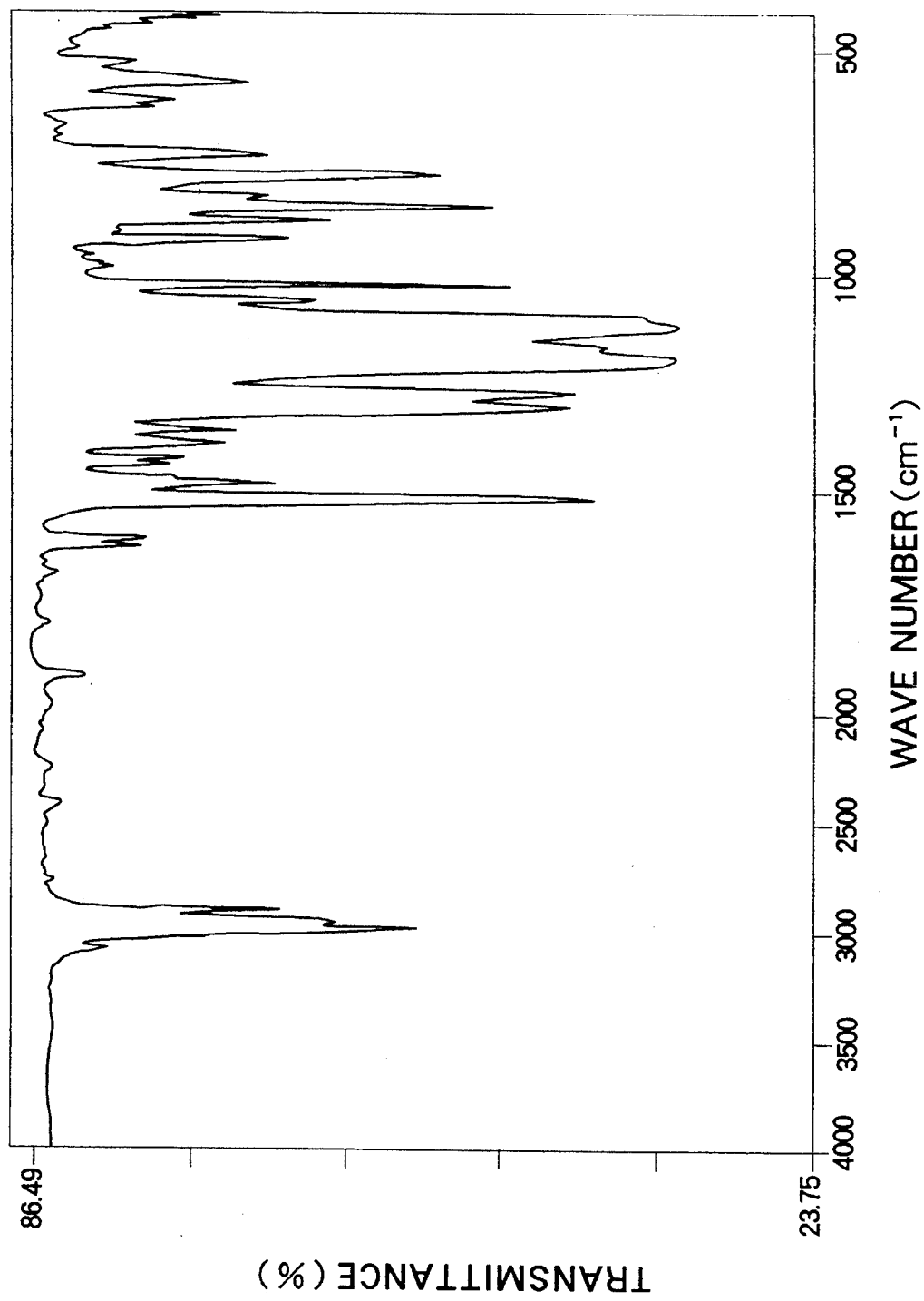
FIG. 1 is a chart showing the infrared spectrum of fluorine-containing aromatic compound [S3][compound (A)] prepared in Referential Example 3.

According to one aspect of the present invention, there is provided a lubricant oil composition comprising:

(A) a fluorine-containing aromatic compound, and (B) an alkyl- or alkyl derivative-substituted aromatic compound having a kinetic viscosity of from 0.1 to 500 cSt as measured at 40 ° C., wherein the fluorine-containing aromatic compound (A) is present in an amount of from 0.1 to 99.9 % by weight, based on the total weight of the fluorine-containing aromatic compound (A) and alkyl- or alkyl derivative-substituted aromatic compound (B).

The lubricant oil composition of the present invention has a kinetic viscosity of from 2 to 500 cSt as measured at 40° C.

In the lubricant oil composition of the present invention, the fluorine-containing aromatic compound being represented by the formula:

$$R(XR_f)_n \qquad (A).$$

In the formula (A), X represents an oxygen or a sulfur atom; and n is an integer of from 1 to 4.

In the formula (A), R represents an n-valent aromatic group, having from 6 to 60 carbon atoms, wherein n is as defined above, comprising at least one unsubstituted or substituted aromatic nucleus selected from the group consisting of an unsubstituted or substituted benzene nucleus and an unsubstituted or substituted naphthalene nucleus, wherein the ratio of carbon atoms in the aromatic nucleus of R to carbon atoms in R is from 0.10 to 1.0, with the proviso that when the n-valent aromatic group comprises at least two unsubstituted or substituted aromatic nuclei, the at least two aromatic nuclei are linked through a single bond or a linkage group containing no aromatic nuclei and having from 0 to 50 carbon atoms and a valence of from 2 to 6 to form a multinuclear structure.

In the formula (A), $R_f$ represents an unsubstituted or partially substituted fluorocarbon group having from 1 to 25 carbon atoms in which the ratio of fluorine atom or atoms to carbon atom or atoms is from 0.6 to 3, wherein the unsubstituted fluorocarbon group is selected from the group consisting of a fluoroalkyl group, a fluoroalkenyl group, a fluoroaryl group, a fluoroalkylaryl and a fluoroaralkyl group, in which each of the alkyl, alkenyl, aryl, alkylaryl and aralkyl groups is partially or entirely substituted with at least one fluorine atom, and the partially substituted fluorocarbon group has at least one substituent other than fluorine and hydrogen atoms in an amount such that the ratio of the at least one substituent to the total number of fluorine and hydrogen atoms of the partially substituted fluorocarbon group is not greater than 1.5, and wherein a main chain of the unsubstituted or partially substituted fluorocarbon group optionally has from 1 to 7 ether linkage.

In the formula (A), when n is an integer of from 2 to 4, the $XR_f$ groups are the same or different.

In the lubricant oil composition of the present invention, the alkyl- or alkyl derivative-substituted aromatic compound (B) comprises at least one substituted aromatic nucleus selected from the group consisting of a substituted benzene nucleus and a substituted naphthalene nucleus, wherein a substituent of the at least one substituted aromatic nucleus is an unsubstituted or substituted alkyl group having from 1 to 30 carbon atoms, or a derivative thereof.

As will be understood from the above, the essential feature of the lubricant oil composition of the present invention consists in comprising the fluorine-containing aromatic compound (A) and the alkyl- or alkyl derivative-substituted aromatic compound (B).

The alkyl- or alkyl derivative-substituted aromatic compound (B) is cheap, but has excellent properties, such as low temperature fluidity, low moisture absorption properties, and high electrical insulation. However, such a compound (B) has a problem in that although it is miscible with hydrofluorocarbons to some extent, the miscibility exhibited thereby is still not sufficient for it to be advantageously used as a lubricant for refrigeration equipment using hydrofluorocarbon (HFC) and hydrofluoroether (HFE) refrigerants. In addition, the compound (B) has another problem in that it inherently exhibits unsatisfactory lubricating properties.

However, as mentioned above, according to the present invention, it has unexpectedly been found that the alkyl- or alkyl derivative-substituted aromatic compound (B) exhibits excellent miscibility with the fluorine-containing aromatic compound (A) and that the resultant lubricant oil composition obtained by mixing compound (A) with compound (B) exhibits miscibility with HFC refrigerants, such as HFC-134a and HFC-32, and HFE refrigerants and, therefore, can be advantageously used as a lubricant for refrigeration equipment.

Further, it is noted that, in the above lubricant oil composition, the lubricating properties of aromatic compound (B) itself can also be remarkably improved. More surprisingly, it has also been found that the lubricant oil composition can synergistically exhibit more excellent lubricating properties than any of the fluorine-containing aromatic compound (A) alone and the alkyl- or alkyl derivative-substituted aromatic compound (B) alone, which are components of the lubricant oil composition.

Further, it should be noted that when the fluorine-containing aromatic compound (A) is used alone as a lubricant for refrigerants, it is unsatisfactory with respect to the desired low temperature fluidity, low moisture absorption properties and high electrical insulation, however, these properties can be remarkably improved by mixing the fluorine-containing aromatic compound (A) with the alkyl- or alkyl derivative-substituted aromatic compound (B).

Furthermore, it should be noted that, by changing the amount of the alkyl- or alkyl derivative-substituted aromatic compound (B) to be added to the fluorine-containing aromatic compound (A), the degree of dissolution of hydrofluorocarbon refrigerant in the refrigeration composition [composed of a refrigerant and a mixture of compound (A) and (B)] can be regulated, so that the viscosity and lubricating properties of the resultant refrigerant composition can be controlled. Thus, it has advantageously become possible to provide lubricant oil compositions suitably adapted for various types of refrigeration systems.

As mentioned above, when the fluorine-containing aromatic compound (A) is mixed with the alkyl- or alkyl derivative-substituted aromatic (B), respective drawbacks inevitably accompanying the compound (A) and the compound (B) can be eliminated, so that an excellent lubricant oil composition can be provided, which can simultaneously satisfy all requirements of properties for use thereof as a lubricant in the refrigeration system employing HFC and HFE refrigerants, such as excellent miscibility with HFC and HFE refrigerants, satisfactory low temperature fluidity, low moisture absorption properties, high electrical insulation, and durability.

This is an unexpected synergistic effect of the present invention, which has not been achieved by the use of compound (A) alone or compound (B) alone. The reasons why the compound (A) has excellent miscibility with a variety of HFC refrigerants (eg., HFC-134a) and HFE refrigerants, have not yet been clearly elucidated. However, the following reasons can be presumed.

Each of HFC and HFE refrigerants has at least one C-F bond and at least one C-H bond, and, hence, it is believed to have a hybrid structure formed of a fluorocarbon group and a hydrocarbon group.

Therefore, it can be understood that the fluorocarbon group of such a refrigerant exhibits affinity to conventional perfluorinated oils (e.g., a perfluoropolyether), whereas the hydrocarbon group thereof does not exhibit affinity to the perfluorinated oil at all.

On the other hand, it has been known that HFC refrigerants, such as HFC-134a, exhibit a miscibility with a perfluorinated polyether to some extent, but the miscibility is unsatisfactory in a low temperature range. This is believed to be due to the fact that the HFC refrigerant has a hydrocarbon group which has low affinity to the perfluorinated polyether.

In the fluorine-containing compound represented by the formula:

$$R(XR_f)_n \qquad (A)$$

the aromatic group R comprising at least one aromatic nucleus is linked to a fluorocarbon group $R_f$ through an oxygen or a sulfur atom. The aromatic group R in formula (A) has affinity to a hydrocarbon group of HFC and HFE refrigerants, whereas the fluorocarbon group $R_f$ in formula (A) has affinity to a fluorocarbon group of such refrigerants. Thus, the fluorine-containing aromatic compound (A) has affinity to both of the fluorocarbon group and hydrocarbon group of HFC and HFE refrigerants, so that the fluorine-containing compound (A) exhibits excellent miscibility with such refrigerants over a wide temperature range.

In this connection, it should be noted that the fluorocarbon group $R_f$ in the fluorine-containing aromatic compound (A) plays an important role in the achievement of miscibility of the compound (A) with HFC or HFE refrigerant. This can be understood from the following experimental facts.

Compounds, respectively, represented by formula (1—1) wherein $R_f$ is —$CF_2CF_2H$ and by formula (1-2) wherein $R_f$ is —$CF_2H$ exhibit miscibility with HFC-134a at from −78° C. to 90° C., whereas a compound represented by formula (1-0) wherein —$CH_2CH_2$ (containing no fluorine atom) is used instead of $R_f$ does not exhibit miscibility with HFC-134a at temperature in the range from room temperature to 90° C.

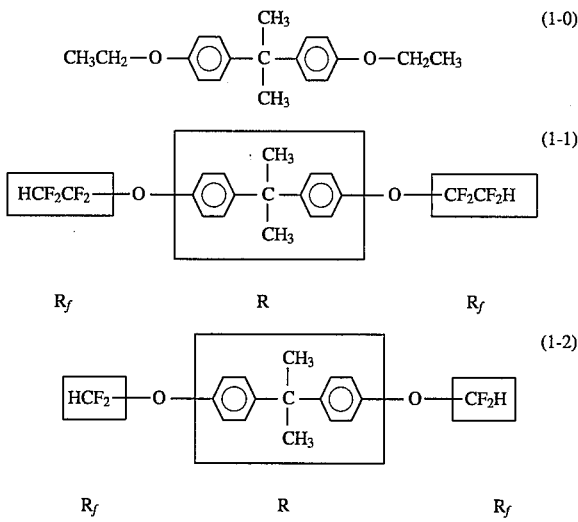

It was found by the present inventors for the first time that the compound (A) comprising the R group and the $R_f$ group exhibits a satisfactory miscibility with HFC and HFE refrigerants having a hybrid structure formed of a fluorocarbon group and a hydrocarbon group.

Since R in formula (A) is a group containing at least one aromatic nucleus, the compound (A) exhibits high stability, as compared to a compound in which the R group in formula (A) is replaced with a saturated alicyclic or a saturated aliphatic hydrocarbon group. The reason for this has not yet been elucidated, however, it is believed to reside in that a R-X-$R_f$ bond is stable when R is a group containing at least one aromatic nucleus, as compared to the case where R is replaced with a saturated alicyclic or a saturated aliphatic hydrocarbon group.

Therefore, with respect to R and $R_f$ in formula (A), there are no other specific restrictions as long as R and $R_f$ satisfy the requirements specified herein.

The mechanism of an achievement of miscibility between the HFC and HFE refrigerants and the lubricant oil composition comprising in combination the fluorine-containing aromatic compound (A) and the alkyl- or alkyl derivative-substituted aromatic compound (B) has not yet been elucidated, but is believed to be as follows.

As mentioned above, the fluorine-containing aromatic compound (A) exhibits excellent miscibility with HFC and HFE refrigerants. On the other hand, it has been found that the fluorine-containing aromatic compound (A) exhibits excellent miscibility with various types of the alkyl- or alkyl derivative-substituted aromatic compounds (B) to be used in the present invention.

That is, the fluorine-containing aromatic compound (A) has amphiphilic characteristics such that it exhibits excellent miscibility not only with HFC and HFE refrigerants, but also with the alkyl- or alkyl derivative-substituted aromatic compound (B).

Therefore, in the refrigerant composition comprising the above-mentioned three components, namely (1) the fluorine-containing aromatic compound (A), (2) the alkyl- or alkyl derivative-substituted aromatic compound (B), and (3) HFC and/or HFE refrigerant, the fluorine-containing aromatic compound (A) is believed to serve as a miscibility agent for the alkyl- or alkyl derivative-substituted aromatic compound (B) and the HFC and/or HFE refrigerant.

Hereinbelow, the present invention will be described in more detail.

The fluorine-containing aromatic compound (A) to be used in the present invention is substantially the same as the fluorine-containing aromatic compound (I) disclosed in EP 0 528 043 A1.

As mentioned above, in order for the fluorine-containing aromatic compound (A) to exhibit high affinity not only to HFC and HFE refrigerants, but also to the alkyl- or alkyl derivative-substituted aromatic compound (B), it is important that the R group in formula (A) be an aromatic group containing at least one aromatic nucleus.

Therefore, with respect to the R group of formula (A), as long as the R group is an aromatic group containing at least one aromatic nucleus, there is no other specific limitations. That is, in formula (A), R represents an aromatic group comprising at least one unsubstituted or substituted aromatic nucleus, wherein when the aromatic group comprises two or more aromatic nuclei, the aromatic nuclei are linked through a linkage group.

A substituent of the at least one aromatic nucleus, and the above-mentioned linkage group can be selected from various types of hydrocarbon groups, polar groups stable under application conditions, and groups containing a polar group.

Even when R contains various types of polar groups, the fluorine-containing aromatic compound (A) exhibits excellent miscibility with HFC and HFE refrigerants. The reason for this is believed to be as follows. HFC and HFE refrigerants have at least one polarized C-H bond due to the electron attractive activity of the fluorine atom of the refrigerant. The polarized C-H bond exhibits strong interaction with various types of polar groups. As a result, even when R contains a polar group, the miscibility of the fluorine-containing aromatic compound (A) with HFC and HFE refrigerants are not inhibited.

As is understood from the above, the structure of R is not specifically restricted as long as R contains at least one unsubstituted or substituted aromatic nucleus. The ratio of carbon atoms in the aromatic nucleus (nuclei) in R to the carbon atoms in the entire structure of R is 0.1 to 1.0, preferably not smaller than 0.2, and more preferably not smaller than 0.5. The number of carbon atoms contained in R is 6 to 60, preferably 6 to 40 and more preferably 6 to 30.

As mentioned above, R may contain a substituent and/or a linkage group in which the number of carbon atoms is 50 or less, preferably 20 or less, and more preferably 15 or less.

With respect to the aromatic nucleus in R, various types of groups exhibiting aromaticity can be used. The aromatic nucleus in the present invention can also contain a heteroatom, such as a nitrogen atom, an oxygen atom, and a sulfur atom. However, it is generally preferable that the aromatic nucleus be selected from aromatic hydrocarbon groups having from 6 to 14 carbon atoms, taking into consideration stability and availability thereof. Preferably, the aromatic nucleus in R is selected from benzene and naphthalene nuclei. Especially is preferred a benzene nucleus.

With respect to the bonding of R to the —$XR_f$ group in the fluorine-containing aromatic compound (A), it is especially preferred that the aromatic nucleus of R be directly bonded to the —$XR_f$ group, since a highly stable compound represented by formula (A) can be easily synthesized.

In formula (A), X represents an oxygen atom or a sulfur atom. When X represents an oxygen atom, the following advantages are brought about:

1) fluorine-containing aromatic compounds can be produced at low cost in high yield from cheap raw materials, and 2) fluorine-containing aromatic ether compounds exhibit extremely high stability.

The value of n in formula (A) depends on the valence of R. In order to facilitate the synthesis of compound (A) and control the viscosity of compound (A) at a value in an appropriate range, n is generally selected from integers of 1, 2, 3 and 4, preferably selected from 2, 3 and 4, and more preferably 2.

When n of formula (A) is 2 or greater, $R_f$ groups may be the same or different.

As mentioned above, R represents an n-valent aromatic group, having from 6 to 60 carbon atoms, wherein n is as defined above, comprising at least one unsubstituted or substituted aromatic nucleus selected from the group consisting of an unsubstituted or substituted benzene nucleus and an unsubstituted or substituted naphthalene nucleus, wherein the ratio of carbon atoms in the aromatic nucleus of in the at least one unsubstituted or substituted aromatic nucleus to carbon atoms in the entire structure of R is from 0.10 to 1.0, with the proviso that when the n-valent aromatic group comprises at least two unsubstituted or substituted aromatic nuclei, the at least two aromatic nuclei are linked through a single bond or a linkage group containing no aromatic nuclei and having from 0 to 50 carbon atoms and a valence of from 2 to 6 to form a multinuclear structure.

Preferred examples of the n-valent aromatic groups R are represented by the formula:

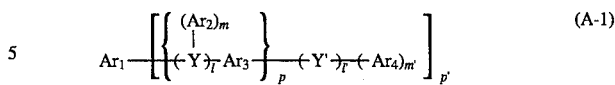
(A-1)

wherein:
p is an integer of from 0 to 2,
p' is an integer of from 0 to 4,
each of l and l' is independently 0 or 1,
m is an integer of from 0 to 2, and
m' is an integer of from 0 to 5.

Each of $Ar_1$, $Ar_2$, $Ar_3$ and $Ar_4$ is independently an unsubstituted or substituted aromatic nucleus selected from the group consisting of an unsubstituted or substituted benzene nucleus and an unsubstituted or substituted naphthalene nucleus. It is especially preferred that the aromatic nucleus be an unsubstituted or substituted benzene nucleus. Substituents of the substituted aromatic nucleus (to which at least one monovalent substituent is bonded) are described below.

On the other hand, Y and Y' are multivalent linkage groups having a valence of from 2 to 4, preferably 2, and a valence of from 2 to 6, preferably from 2 to 3, more preferably 2, respectively, and are each independently selected from the group consisting of the following ($a_1$), ($a_2$) and ($a_3$):

(I) ($a_1$) a 2 to 6-valent saturated or unsaturated hydrocarbon group having from 1 to 20 carbon atoms, preferably from 1 to 15 carbon atoms, more preferably from 1 to 10 carbon atoms, which is optionally, partially or entirely substituted with a fluorine atom. When the hydrocarbon group is partially or entirely substituted with a fluorine atom, the ratio of fluorine atoms in the hydrocarbon group to carbon atoms in the hydrocarbon group is from 0.05 to 2, preferably from 0.2 to 2, more preferably from 0.5 to 2.

Examples of multivalent groups include the following groups:

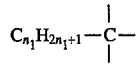

wherein $n_1$ is an integer of from 0 to 19, preferably from 1 to 12, for example,

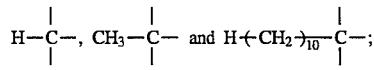

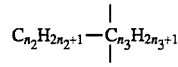

wherein $n_2$ and $n_3$ are each independently an integer of from 0 to 19, preferably from 1 to 12, for example,

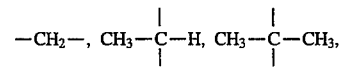

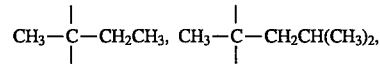

-continued

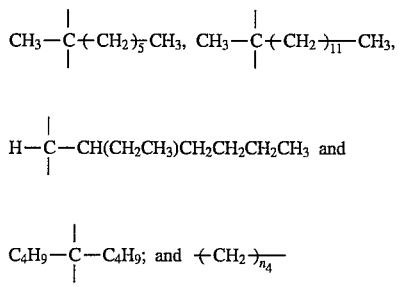

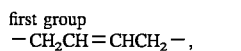

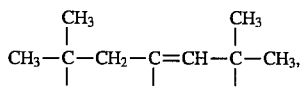

wherein $n_4$ is an integer of from 2 to 12 (examples thereof include —$CH_2CH_2$— and —$CH_2CH_2CH_2CH_2$—).

Examples of multivalent groups having other structures include:

first group
—$CH_2CH=CHCH_2$—,

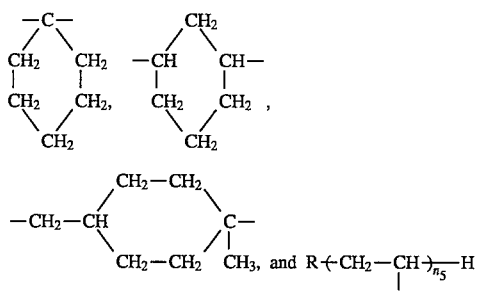

(wherein R represents a hydrogen atom or a $C_1$-$C_6$ alkyl group, and $n_5$ is an integer of from 2 to 6),
(this first group is an example of Y' for formula (A-1) wherein l is 0, l' is 1, m' is 5 and p' is 1); and second group

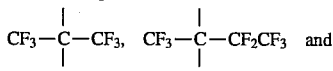

(II) ($a_2$) a bivalent or a trivalent group having from 0 to 20 carbon atoms, preferably from 0 to 12, more preferably from 0 to 8, selected from the group consisting of the following ($a_2$-1) to ($a_2$-4):

($a_2$-1) an oxygen atom (—O—), ($a_2$-2) a carbonyl-containing multivalent group selected from the group consisting of a carbonyl group, an ester linkage, an amide linkage and a carbonate linkage, ($a_2$-3) a sulfur atom (—S—), or a sulfur-containing multivalent group selected from the group consisting of a sulfonyl group and a sulfinyl group, and ($a_2$-4) a multivalent group containing a nitrogen atom, a phosphorus atom or a silicon atom, which is selected from the group consisting of groups respectively represented by the following formulae:

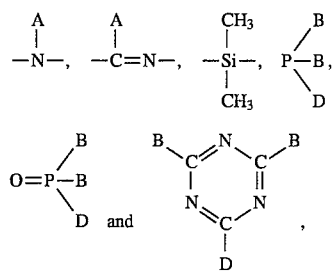

wherein:
A represents a single bond, a hydrogen atom or an alkyl group having from 1 to 6 carbon atoms,
B represents a single bond or an oxygen atom (—O—),
D represents a single bond, an oxygen atom (—O—), —R or —OR in which R represents an alkyl group having from 1 to 20 carbon atoms.

Multivalent linkage groups Y and Y' may form a structure in which 2 or 3 types of the above-mentioned multivalent groups are combined, or may form a heteroatom-containing ring structure in which the above-mentioned multivalent groups are bonded to an aromatic nucleus at two carbon atoms thereof.

Examples thereof are shown below:

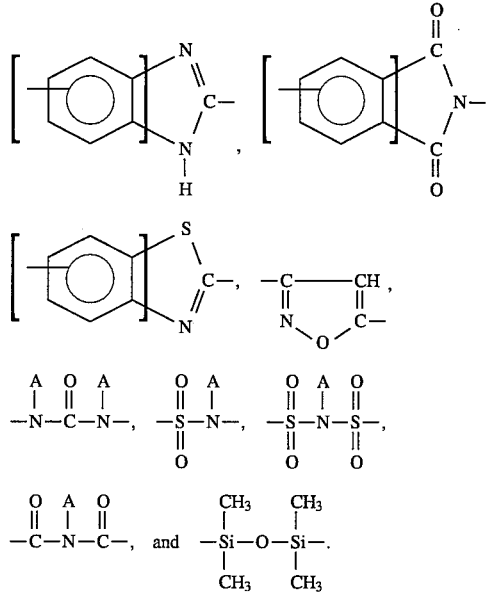

When the multivalent linkage groups have an asymmetrical structure, such as an ester linkage, the ester linkage means the both structures of

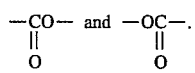

Illustrative examples of multivalent linkage groups ($a_2$) are shown below:

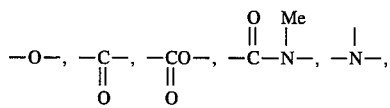

-continued

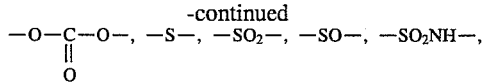

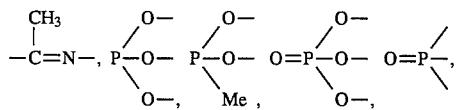

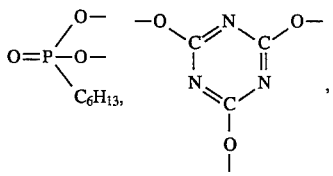

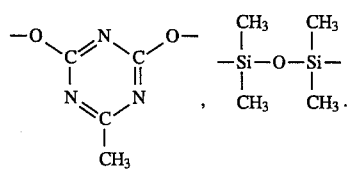

[III] (a₃) a 2 to 6-valent group having from 1 to 50 carbon atoms and having a structure such that the group (a1) has the group (a2) introduced therein or to a terminal thereof, i.e., a 2 to 6-valent group having a structure such that at least one multivalent group ($a_2$) is bonded to the carbon skeleton of the group ($a_1$1), and/or a structure such that at least one multivalent group $A_2$) is introduced between a carbon-carbon bond of the carbon skeleton of the group (a1).

The number of the multivalent group $A_2$) contained in the 2 to 6-valent group (a3) is generally from 1 to 6, preferably from 1 to 4, more preferably 1 to 3. When the 2 to 6-valent group (a3) contains a polyalkylene oxide structure or a polydimethylsiloxane structure, the upper limit of the number of the multivalent groups ($A_2$) is 20.

The number of the carbon atoms contained in the group (a3) is generally from 1 to 20, preferably from 2 to 12, more preferably from 2 to 8. When the group ($_3$) contains a polyalkylene oxide structure or a polydimethylsiloxane structure, the upper limit of the carbon atoms in the group ($_3$) is 50.

Particular examples of the group ($_3$) are shown below:
—OCH₂—, —OCH₂CH₂—, —CH₂₀CH₂—,
—O—(CH₂CH₂O—)ₙ(wherein n is an integer of from 1 to 9),

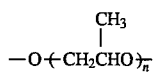

(wherein n is an integer of from 1 to 7),
—O—(CH₂CH₂CH₂CH₂O—)ₙ (wherein n is an integer of from to 5),

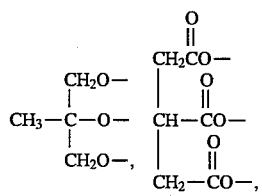

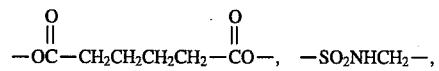

-continued

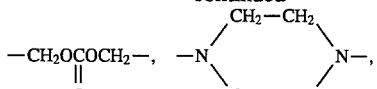

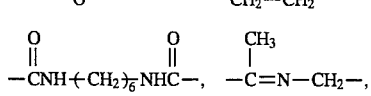

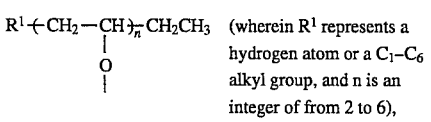

R¹—(CH₂—CH)ₙ—CH₂CH₃ (wherein R¹ represents a hydrogen atom or a C₁–C₆ alkyl group, and n is an integer of from 2 to 6),

—OCF₂CF₂CF₂CF₂O—, —OCH₂CF₂CF₂CH₂O—,

—CH₂OCH₂CF₂CF₂CF₂CF₂CH₂OCH₂—,

—CH₂CH₂CF₂CF₂CH₂CH₂—, and

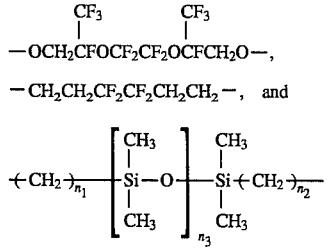

(wherein R¹ represents a hydrogen atom or a C₁–C₆ alkyl group, and n is an integer of from 2 to 6),
n₂ independently represents an inteter of from 0 to 3, and n₃ represents an integer of from 0 to 20, preferably from 1 to 12, more preferably from 1 to 8.

Each of the substituted aromatic nuclei $Ar_1$, $Ar_2$, $Ar_3$ and $Ar_4$ has at least one monovalent substituent independently selected from the group consisting of the following ($b_1$) to ($b_4$):

($b_1$) a monovalent hydrocarbon group having from 1 to 30 carbon atoms, which is selected from the group consisting of an alkyl, an alkenyl, a cycloalkyl and a cycloalkenyl group, ($b_2$) a monovalent group selected from the group consisting of a hydroxyl group, a thiol group, a nitrile group, a nitro group, a fluorine atom and a chlorine atom, ($b_3$) a substituted monovalent hydrocarbon group having 50 or less carbon atoms, wherein the monovalent hydrocarbon group is substituted with at least one substituent selected from the group consisting of the monovalent group $b_2$) defined above and the bivalent group ($a_2$) defined for the linkage groups Y and Y', with the proviso that the sum of the number of the monovalent group $b_2$) and the number of the bivalent group ($a_2$) is from 1 to 3, and ($b_4$) a fluorine-substituted monovalent group having a structure such that at least one hydrogen atom of carbon-to-hydrogen bonds of the monovalent hydrocarbon group ($b_1$) or the substituted monovalent hydrocarbon group ($b_3$) is substituted with a fluorine atom,
with the proviso that the sum, per aromatic nucleus, of the number of substituents bonded to the aromatic nucleus of each of $Ar_1$, $Ar_2$, $Ar_3$ and $Ar_4$ and the number of the linkage groups Y and Y' is from 0 to 4 and that each —XR$_f$ group of formula (A) is bonded to a carbon atom, preferably a carbon atom of the aromatic nucleus, of the R group represented by formula (A-1).

The sum, per aromatic nucleus, of the number of substituents bonded to the aromatic nucleus of each of $Ar_1$, $Ar_2$, $Ar_3$ and $Ar_4$ and the number of the linkage groups Y and Y' is from 0 to 4, preferably from 1 to 2, more preferably 1.

Examples of substituents of the aromatic nuclei represented by $Ar_1$, $Ar_2$, $Ar_3$ and $Ar_4$ are shown below:

—$CH_3$, —$CH_2CH_3$, —$CH(CH_3)_2$, —$C(CH_3)_3$, —$(C_2H_4)_{n_a}H$ (wherein $n_a$ is an integer of from 2 to 10), —$(C_3H_6)_{n_b}H$ (wherein $n_b$ is an integer of from 1 to 10),

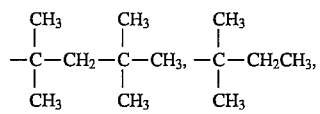

—$CH(CH_3)$—$C_{n_c}H_{2n_c+1}$ (wherein $n_c$ is an integer of from 1 to 20),

—$C(CH_3)_2$—$C_{n_d}H_{2n_d+1}$ (wherein $n_d$ is an integer of from 1 to 20),

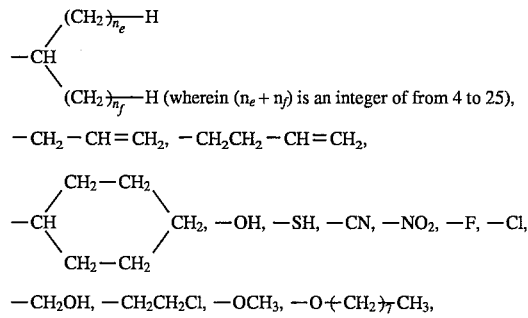

(wherein $(n_e + n_f)$ is an integer of from 4 to 25),

—$CH_2$—$CH$=$CH_2$, —$CH_2CH_2$—$CH$=$CH_2$,

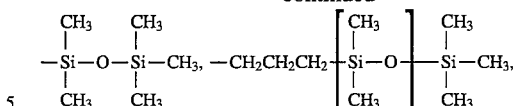, —OH, —SH, —CN, —$NO_2$, —F, —Cl,

—$CH_2OH$, —$CH_2CH_2Cl$, —$OCH_3$, —O$(CH_2)_7CH_3$,

—$OCH_2CH_2OCH_3$, $(OCH_2CH_2)_{20}$—$OC_4H_9$, $(OC_3H_6)_{10-15}OCH_2CH_3$, $(OCH_2CH_2CH_2CH_2)_2 OCH_2CH_2CH_2CH_3$,

—$OCH_2CH_2OCH_2CH_2OCH_3$, 

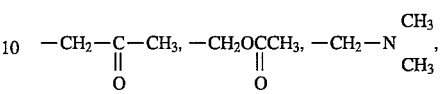

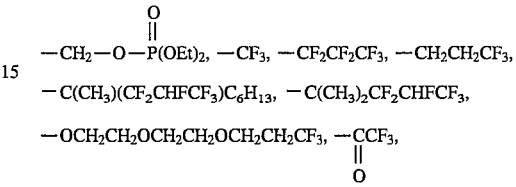

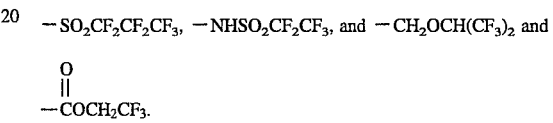

—S—$C_4H_9$, —$SO_2NMe_2$, —$NHSO_2CH_3$, —S(=O)—$CH_3$, —$SO_2C_6H_{13}$,

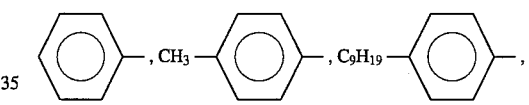

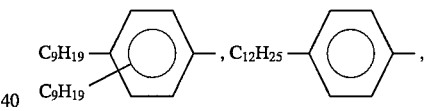

—Si—O—Si—$CH_3$, —$CH_2CH_2CH_2$[Si—O]$_{10}$—Si—$CH_3$

—$CH_2OCH_2CH_3$, —$CH(CH_3)O$—$(CH_2CH_2O)_5CH_3$,

—$CH_2$—C(=O)—$CH_3$, —$CH_2OCCH_3$(=O), —$CH_2$—$N(CH_3)_2$,

—$CH_2$—O—P(=O)(OEt)$_2$, —$CF_3$, —$CF_2CF_2CF_3$, —$CH_2CH_2CF_3$,

—$C(CH_3)(CF_2CHFCF_3)C_6H_{13}$, —$C(CH_3)_2CF_2CHFCF_3$,

—$OCH_2CH_2OCH_2CH_2OCH_2CH_2CF_3$, —$CCF_3$(=O),

—$SO_2CF_2CF_2CF_3$, —$NHSO_2CF_2CF_3$, and —$CH_2OCH(CF_3)_2$ and

—$COCH_2CF_3$(=O).

In the above formulae, Me and Et mean methyl and ethyl, respectively.

Specific examples of R in formula (A), in which the above-mentioned substituents and linkage groups are contained, include the following groups:

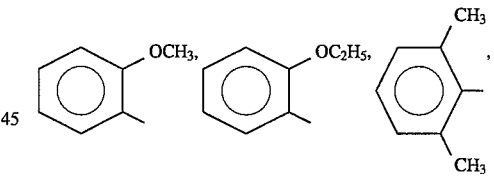

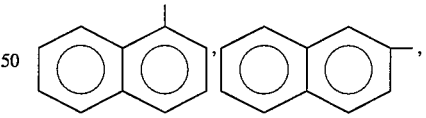

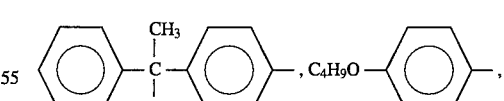

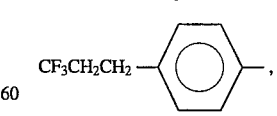

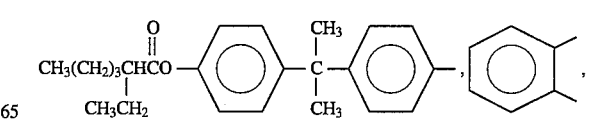

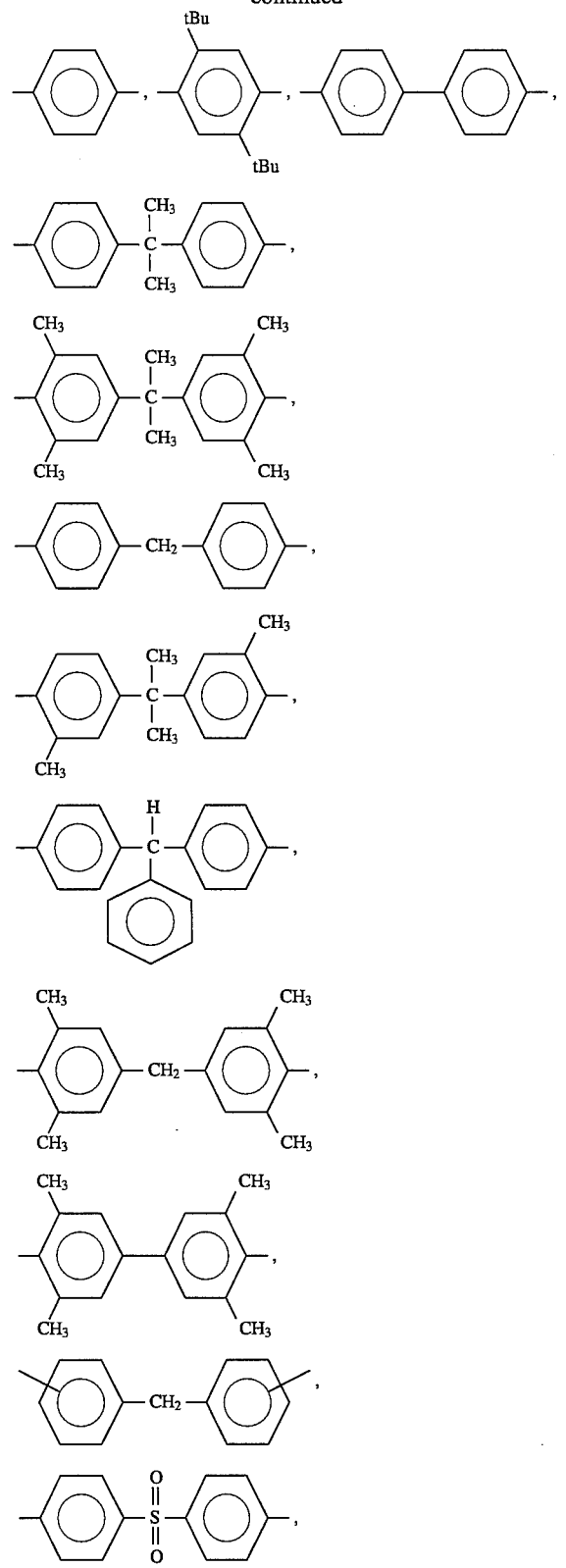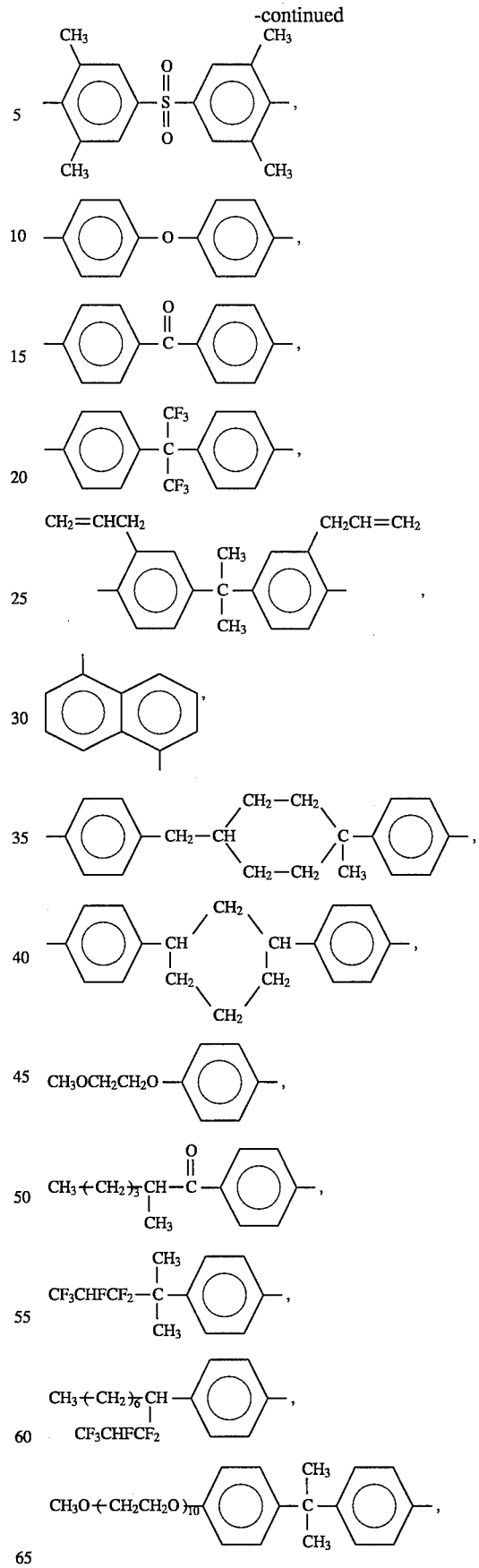

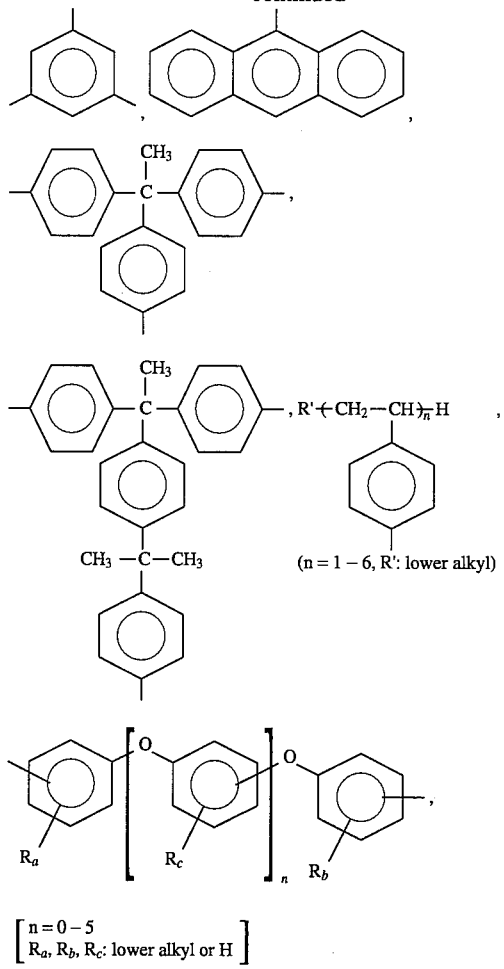

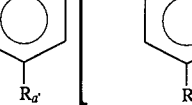

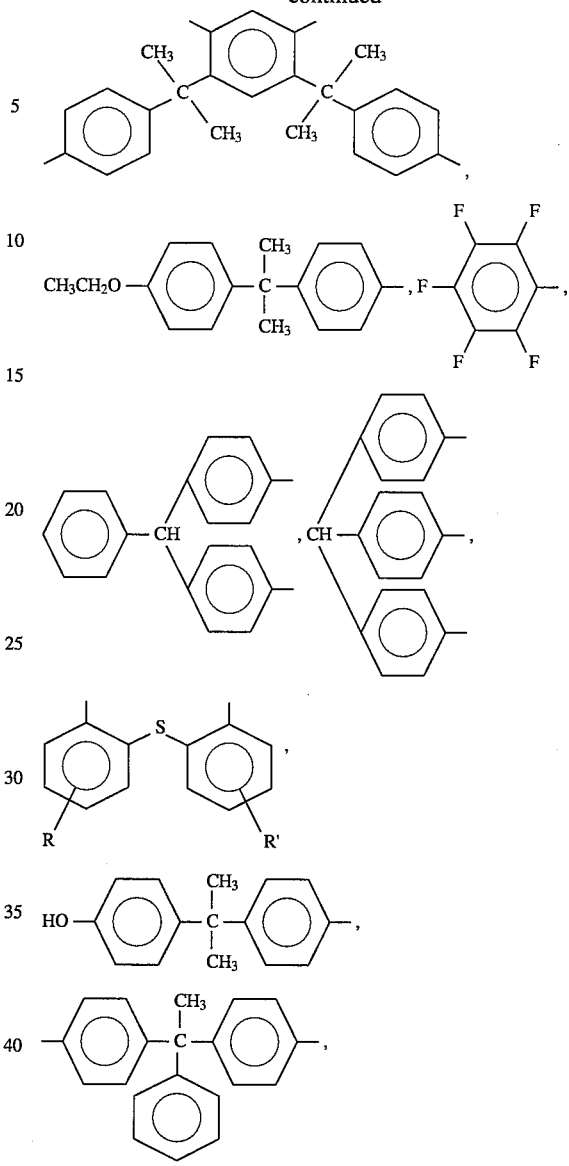

In formula (A), $R_f$ represents an unsubstituted or partially substituted fluorocarbon group having from 1 to 25 carbon atoms, and having a valence of 1.

The above-mentioned unsubstituted fluorocarbon group is selected from the group consisting of a fluoroalkyl group, a fluoroalkenyl group, a fluoroaryl group, a fluoroalkylaryl and a fluoroaralkyl group, in which each of the alkyl, alkenyl, aryl, alkylaryl and aralkyl groups is partially or entirely substituted with at least one fluorine atom. Of these groups, fluoroalkyl groups and fluoroalkenyl groups are preferred because their synthesis is easy.

The partially substituted fluorocarbon group has at least one substituent other than fluorine and hydrogen atoms.

The main chain of the unsubstituted or partially substituted fluorocarbon group may optionally have at least one ether linkage therein.

When the main chain includes at least one ether linkage, the number of the ether linkages is from 1 to 7, preferably from 1 to 3.

In addition, as $R_f$, the unsubstituted or partially substituted fluorocarbon group or its derivative group having at least one ether linkage therein may be substituted with other substituent.

When the $R_f$ contains a substituent other than a fluorine atom and an ether linkage, the number of such substituents is generally from 1 to 4, preferably from 1 to 2, more preferably 1.

As such a substituent, there is no particular limitation as long as the fluorine-containing aromatic compound (A) is stable during the use in a refrigerator. However, the following examples of substituents can be mentioned:

(1) a halogen atom, exclusive of a fluorine atom, i.e., a chlorine atom, a bromine atom and an iodine atom. Of these, a chlorine atom is preferred;

(2) an active hydrogen-containing monovalent group selected from the group consisting of a hydroxyl group, an amino group and a thiol group, with the proviso that the active hydrogen-containing group is not bonded to the carbon atom having a halogen atom bonded thereto; and (3) a monovalent group having from 1 to 10 carbon atoms, preferably from 1 to 6 carbon atoms, more preferably from 1 to 3 carbon atoms, and selected from the group consisting of a thioalkoxy group, an alkyl-substituted amino group, an acyl group, an acyloxy group, a carboalkoxy group, a nitrile group, an amido group and an imido group, which are optionally substituted with at least one fluorine atom.

The ratio of the at least one substituent to the total number of fluorine and hydrogen atoms of the partially substituted fluorocarbon group is not greater than 1.5, preferably not greater than 1.0.

Of these partially substituted fluorocarbon groups mentioned above, ether linkage-containing fluorocarbon groups and chlorine-containing fluorocarbon groups are preferred because not only is excellent stability exhibited but also synthesis is easy.

In $R_f$, the ratio of fluorine atom to carbon atom is generally from 0.6 to 3, preferably from 1 to 3, and more preferably from 1.5 to 3. When the ratio of fluorine atom to carbon atom in $R_f$ is too low, unfavorably, the compound of formula (A) is likely to exhibit poor miscibility with hydrofluorocarbons or fluorine-containing ether refrigerants and exhibit poor stability.

The number of carbon atoms in $R_f$ is generally in the range of from 1 to 25, preferably from 1 to 10, and more preferably from 1 to 3. When the number of carbon atoms in $R_f$ is greater than 25, unfavorably, various problems arise such that it is difficult to obtain raw materials and also to synthesize a product therefrom, that synthesis and subsequent purification thereof are time-consuming, and that the viscosity of an obtained product becomes too high.

As the structure of $R_f$, there is no particular limitation as long as the above-mentioned requirements are satisfied. The representative structure of $R_f$ is shown below, but is not limited to the following structure.

A preferred structure of the unsubstituted or partially substituted fluorocarbon group $R_f$ of formula (A) is represented by the formula:

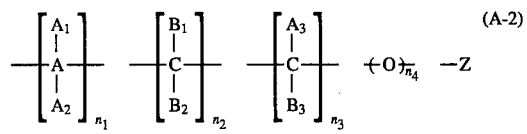

wherein:

each of $A_1$, $A_2$ and $A_3$ is independently a fluorine atom or a fluoroalkyl group having from 1 to 6 carbon atoms, preferably from 1 to 3 carbon atoms, more preferably a fluorine atom or $—CF_3$, wherein the fluorine atom is optionally replaced with or the fluoroalkyl group is optionally substituted with at least one substituent selected from the group consisting of:

($C_1$) a halogen atom, exclusive of a fluorine atom, ($C_2$) an active hydrogen-containing monovalent group selected from the group consisting of a hydroxyl group, an amino group and a thiol group, with the proviso that the active hydrogen-containing group is not bonded to the carbon atom having a halogen atom bonded thereto, and ($C_3$) a monovalent group having from 1 to 10 carbon atoms, and selected from the group consisting of a thioalkoxy group, an alkyl-substituted amino group, an acyl group, an acyloxy group, a carboalkoxy group, a nitrile group, an amido group and an imido group, which are optionally substituted with at least one fluorine atom, each of $B_1$, $B_2$ and $B_3$ is independently a hydrogen atom or an alkyl group having from 1 to 6 carbon atoms, preferably from 1 to 3 carbon atoms, more preferably a hydrogen atom or $CH_3$, wherein the hydrogen atom is optionally replaced with or the alkyl group is optionally substituted with a substituent selected from the group consisting of:

($C_1$) a halogen atom, exclusive of a fluorine atom, ($C_2$) an active hydrogen-containing monovalent group selected from the group consisting of a hydroxyl group, an amino group and a thiol group, with the proviso that the active hydrogen-containing group is not bonded to the carbon atom having a halogen atom bonded thereto, and ($C_3$) a monovalent group having from 1 to 10 carbon atoms, and selected from the group consisting of a thioalkoxy group, an alkyl-substituted amino group, an acyl group, an acyloxy group, a carboalkoxy group, a nitrile group, an amido group and an imido group, which are optionally substituted with a fluorine atom, Z is a terminal group selected from the group consisting of a hydrogen atom, a fluorine atom, a phenyl group and a phenyl group substituted with an alkyl group having from 1 to 10 carbon atoms, wherein the phenyl group and substituted phenyl group are further unsubstituted or substituted with at least one fluorine atom, $n_1$ is an integer of from 0 to 25, and each of $n_2$ and $n_3$ is independently an integer of from 0 to 10, with the proviso that ($n_1+n_3$) is not zero, $n_4$ is an integer of from 0 to 7.

In formula (A-2), when $n_1$ is an integer of 2 or more, the ($CA_1A_2$) units are the same or different, when $n_2$ is an integer of 2 or more, the ($CB_1B_2$) units are the same or different, and when $n_3$ is an integer of 2 or more, the ($CA_3B_3$) units are the same or different.

In formula (A-2), the ($CA_1A_2$), ($CB_1B_2$), ($CA_3B_3$) and $-(-O-)-$ units may be arranged in any order, with the proviso that the $-(-O-)-$ units are not directly linked to each other, that the $-(-O-)-$ unit is not positioned at a terminal of formula (A-2) and not directly linked to a hydrogen atom or a fluorine atom, and that a main chain of formula (A-2) optionally contains one or two double bonds each formed, between a unit selected from ($CA_1A_2$), ($CB_1B_2$) and ($CA_3B_3$) units and a neighbouring unit selected from ($CA_1A_2$), ($CA_2B_2$) and ($CA_3B_3$), by a connection of $A_1$-$B_1$, $A_1$-$A_3$, $B_1$-$A_3$, $A_2$-$B_2$, $A_2$-$B_3$ or $B_2$-$B_3$ thereof in which each of $A_1$, $A_2$, $A_3$, $B_1$, $B_2$ and $B_3$ is a single bond.

The fluorine atoms or hydrogen atoms of $R_f$ represented by formula (A-2) may be partially substituted with at least one substituent selected from the group consisting of a halogen atom exclusive of a fluorine atom, an active hydrogen-containing monovalent group and a substituent having not more than 10 carbon atoms, provided that the number of the substituents is from 1 to 4.

Examples of $R_f$ groups are set out below, which are, however, only some examples of $R_f$ groups. These examples should not be construed to be limiting the present invention, and other various $R_f$ groups can be employed.

$$Z^7-(CF_2)_{L_1}-(CH_2)_{L_2}- \quad (1)$$

wherein $Z^7$ represents a fluorine atom, a chlorine atom, an iodine atom or a hydrogen atom, $L_1$ is an integer of from 1 to 18, and $L_2$ is 0, 1 or 2.

Specific examples of groups of formula (1) include the following groups:
$CF_3-$, $CF_3CH_2-$, $CF_3CH_2CH_2-$,
$F-(CF_2)_2-$, $F-(CF_2)_3-$, $F-(CF_2)_6-$,
$F-(CF_2)_{10}-$, $F-(CF_2)_2-CH_2-$,
$F-(CF_2)_4-CH_2-$, $F-(CF_2)_4-CH_2CH_2-$,
$F-(CF_2)_8-CH_2CH_2-$,
$I-(CF_2)_4-CH_2CH_2-$, $C_1CF_2-$,
$Cl-(CF_2)_2-$, $C_1-(CF_2)_4-$,
$Cl(CF_2)_3-CH_2-$, $BrCF_2CF_2-$, $BrCF_2-$,
$I-CF_2-$, $I-(CF_2)_3-CH_2-$,
$H-(CF_2)_3CH_2-$, $H-(CF_2)_{10}-CH_2-$,
$HCF_2-$, $HCF_2CH_2CH_2-$, $HCF_2CH_2-$, and
$I-(CF_2)_2-CH_2CH_2-$.

$$\begin{matrix} & CF_3 & & CF_3 \\ & | & & | \\ F-(CFCF_2O)_{L_2}- & CFCH_2- \end{matrix} \quad (2)$$

wherein $L_2$ is an integer of from 1 to 7.

$$F\left[\begin{matrix} CF_3 \\ | \\ CFCF_2O \end{matrix}\right]_{L_{2'}} CX'FCF_2- \quad (3)$$

wherein $L_2'$ is an integer of from 1 to 7, and $X'$ represents a hydrogen atom, a chlorine atom or a bromine atom.

$$F-(CF_2CF_2O)_{L_3}-CF_2CH_2- \quad (4)$$

wherein $L_3$ is an integer of from 1 to 11.

$$F-(CF_2CF_2CF_2O)_{L_4}-CF_2CF_2CH_2- \quad (5)$$

wherein $L_4$ is an integer of from 1 to 7.
$CF_3CHF-$, $CH_3CF_2-$, $CH_2FCF_2-$,
$CF_2HCF_2-$, $CH_2F-$,
$CHF_2CH_2-$, $CF_3CCl_2-$, $CF_3CHCl-$,
$CF_3CFCl-$, $CFCl_2CF_2-$,
$CHFClCF_2-$, $C_6F_5-$, $CHCl_2CF_2-$,
$CH_3CHFCH_2-$, $CH_2FCH(CH_3)-$,
$CF_3CHFCF_2-$, $CF_3CF_2CHFCF_2-$,
$HOCH_2CF_2CF_2CH_2-$, $CH_2ClCF_2-$, and $CF_3CHClCF_2-$.

$$-CZ_3Z_4CFZ_3Z^4 \quad (6)$$

wherein each of $Z^3$ and $Z^4$ independently represents a fluorine atom, a chlorine atom, a bromine atom, a $CF_3$ group or a hydrogen atom.

$$-CH_2CHCH_2OCH_2R_f' \quad (7)$$
$$\quad\quad |$$
$$\quad\quad OH$$

wherein $R_f'$ represents a fluorocarbon residue having from 1 to 16 carbon atoms.

$$-CF_2CX^1X^2H \quad (8)$$

wherein each of $X^1$ and $X^2$ independently represents a fluorine atom, a chlorine atom or a hydrogen atom.

$$-C_{n'}F_{2n'-1} \quad (9)$$

wherein $n'$ is an integer of from 2 to 20. Examples of group (9) include the following groups of formulae (10) and (11):

$$-C_{3m}F_{6m-1} \quad (10)$$

wherein $m$ is an integer of 2 or more, preferably from 2 to 6.

$$-C_{2m}F_{4m'-1} \quad (11)$$

wherein $m'$ is an integer of 2 or more, preferably from 2 to 10.

$$-C_{n'}F_{2n'}H \quad (12)$$

wherein $n'$ is an integer of from 2 to 20. Examples of group (12) include the following groups of formulae (13) and (14):

$$-C_{3m}F_{6m}H \quad (13)$$

wherein $m$ is an integer of 2 or more, preferably from 2 to 6.

$$-C_{2m}F_{4m}H \quad (14)$$

wherein $m'$ is an integer of 2 or more, preferably from 2 to 10.

Specific examples of groups represented by formulae (9) to (14) include the following groups:
$CF_2=CF-$, $CF_2=CFCF_2-$, $CF_3CF=CF-$,
$CF_3CF_2CF=CF-$, $(CF_3)2C=CF-$, $C_6F_{11}-$, $C_9F_{17}-$,
$C_{12}F_{23}-$, $C_{15}F_{29}-$, $C_{10}F_{19}-$, $CF_3CHFCF_2-$, $C_6F_{12}H-$,
$C_9F_{18}H-$, $C_4F_8H-$, and $C_{10}F_{20}H-$.

In addition, the following groups can also be used.
$CFCl=CF-$, $CFCl_2CF_2CF=CF-$, $CF_3CCl=CF-$,
$CCl_2=CF-$, $CHCl=CF-$, $(CF_3)_2CH-$,
$CF_3CFClCFCl-$ and $-CF(C_2F_5)CH(CF_3)CF_2OC_6H_4-$
$C_6H_{13}$.

The fluorine—containing aromatic compound to be employed in the present invention and represented by formula (A) can be synthesized by various methods.

Hereinbelow, an illustrative mode of synthesis is described for a compound represented by formula (A), wherein n is 1. Other compounds of formula (A) wherein n is 2, 3, or 4 may also be synthesized according to a similar procedure: (1) Reaction of a phenol or a thiophenol with a fluorine-containing olefin:

A number of methods are known for the synthesis of fluorine-containing aromatic compounds by the reaction of phenols or thiophenols with fluorine-containing olefins.

Representative examples of methods are illustrated below, wherein a perfluoroolefin is used as a fluorine-containing olefin:

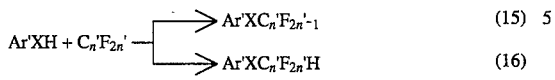

(15)
(16)

wherein Ar' represents a monovalent aromatic group, X represents an oxygen atom or a sulfur atom, and n' is an integer of from 2 to 20.

Representative examples of reactions between phenols and fluorine-containing olefins, are indicated below.

For example, Advance in Fluorine Chemistry, 4, 50 (1965) indicates examples of reactions similar to those of formulae (15) and (16) in connection with the ionic reactions of the following various types of fluorine-containing olefins with phenols, alcohols or thiophenols.

$CF_2=CF_2$, $CF_2=CFCl$, $CF_2=CFBr$,
$CF_2=CFH$, $CF_2=CHCl$, $CF_2=CCl_2$,
$CHF=CCl_2$, $CF_3CF=CF_2$, $CClF_2CF=CF_2$,
$CF_3CCl=CF_2$, $CF_3CF=CCl_2$, $CF_3CCl=CClF$,
$CF_3CH=CH_2$, $CF_3CH=CHCl$, $CF_3CCl=CHCl$,
$CF_3CCl=CCl_2$, $CF_3CF_3CF_2CF=CF_2$,
$CF_3CF=CFCF_3$, $(CF_3)_2C=CF_2$,
$CF_2=CF-CF=CF_2$,

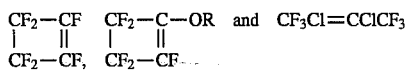

wherein $R_1$ represents an alkyl group.

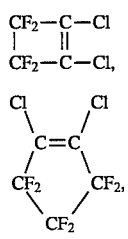

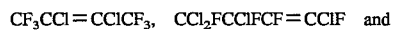

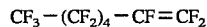

journal of American Chemical Society, 73, 5831 (1951) discloses the reaction:

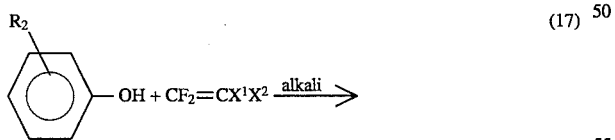
(17)

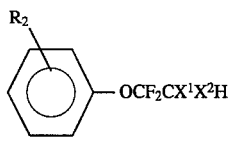

wherein $R_2$ represents a hydrogen atom or an alkyl group, and $X^1$ and $X^2$ each independently represent a fluorine atom a chlorine atom or a hydrogen atom.

142nd Meeting American Chemical Society, Atlantic City, N.J., Sept. 1962 Abs, P19U discloses the reaction:

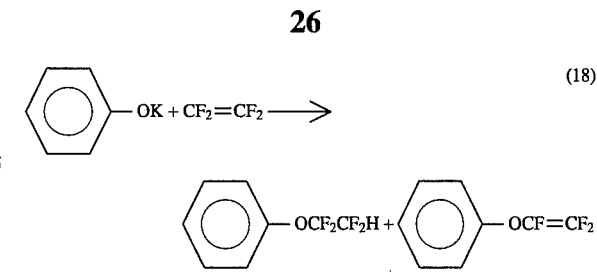
(18)

Journal of American Chemical Society, 82, 5116 (1960) discloses the reaction:

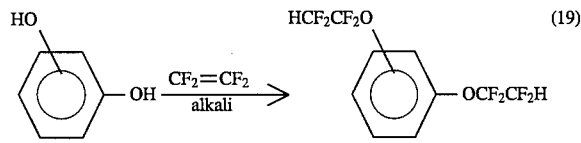
(19)

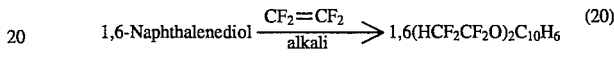
(20)

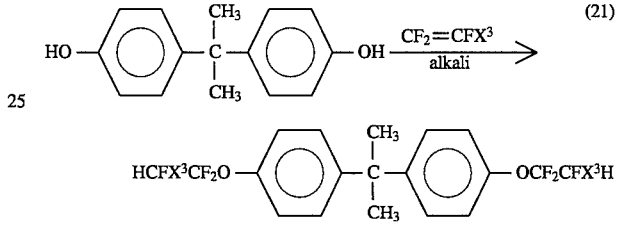
(21)

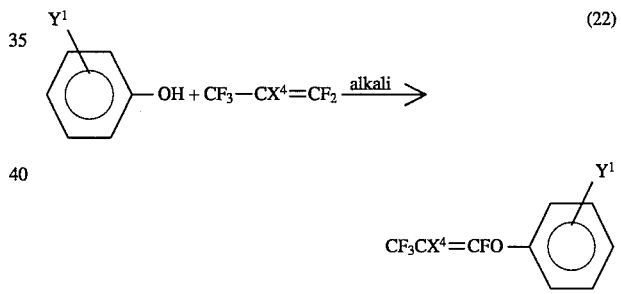

wherein $X^3$ represents a chlorine atom or a fluorine atom.

Nippon Kagakukai-shi 1975, 311 discloses the reaction:

(22)

wherein $Y^1$ represents a hydrogen atom, —OMe or —NO$_2$, and $X^4$ represents a fluorine atom or —CF$_3$.

$$PhOH + CF_3CF=CF_2 \rightarrow CF_3CHFCF_2OPh \qquad (23)$$

Unsaturated bond-containing oligomers derived from various fluorine-containing olefins, such as a hexafluoropropene (HFP) oligomer of formula (24) below, a tetrafluoroethylene (TFE) oligomer of formula (25) below and a chlorotrifluoroethylene oligomer, can also be used as a raw material in the synthetic reactions as represented by formulae (15) and (16) above.

$$C_{3m}F_{6m} \qquad (24)$$

wherein m is an integer of 2 or greater, preferably from 2 to 6.

$$C_{2m'}F_{4m'} \qquad (25)$$

wherein m' is an integer of 2 or greater, preferably from 2 to 10.

Examples of reactions of such oligomers include the following reactions:

Bull. Chem. Soc. Japan, 49 502 (1976) discloses the reaction:

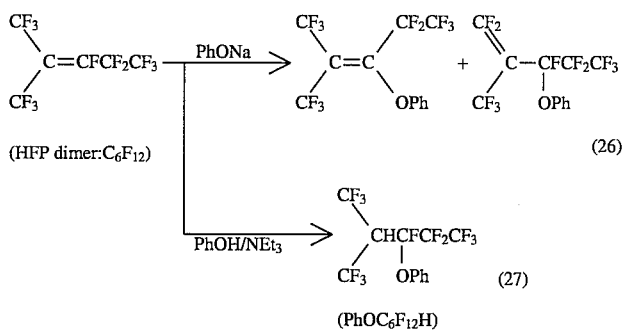

(26)

(27)

wherein Et represents an ethyl group.

Nippon Kagakukai-shi 1978, 253 discloses the reaction:

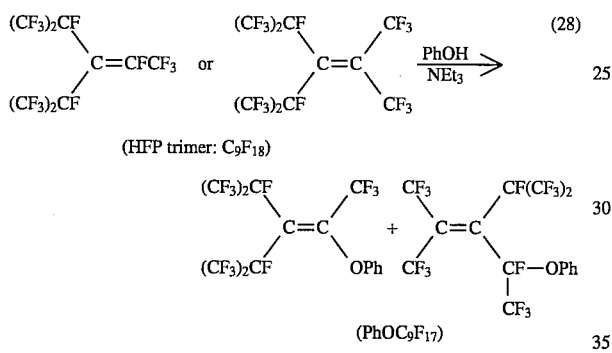

(28)

"Oligomer" edited by Okawara, Saegusa and Higashimura and published by Kodansha Scientific Ltd. (1976) pages 288 to 291, discloses representative examples of reactions between various TFE pentamers ($C_{10}F_{20}$) or HFP trimers ($C_9F_{18}$) and phenols, as represented by the following formulae:

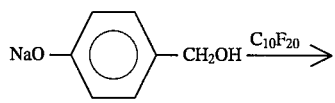

(29)

(30)

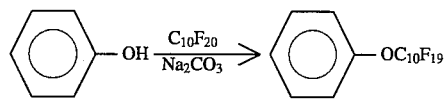

(31)

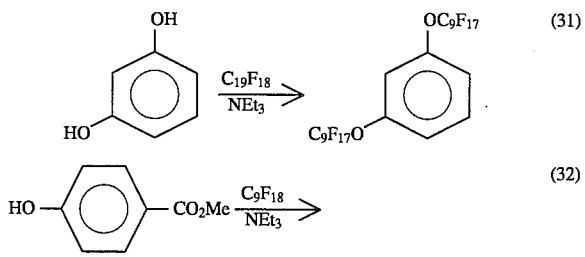

(32)

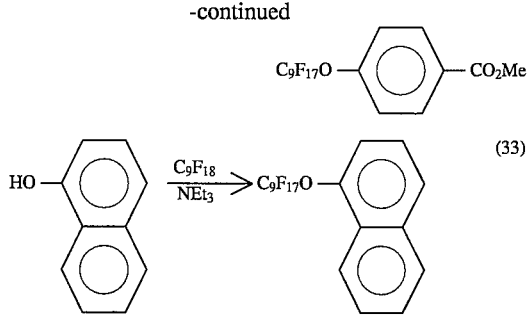

(33)

Journal of Fluorine Chemistry 54, 162 (1991) discloses addition reactions between a perfluorovinyl ether and a phenol, as represented by formulae (34') and (34'):

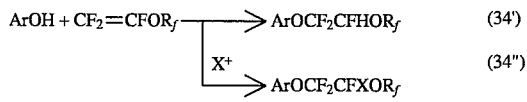

(34')

(34")

wherein $R_f$ represents —$C_3F_7$, —$CF_2CF(CF_3)OC_3F_7$ or —$CF_2CF(CF_3)OCF_2CF_2CO_2CH_3$, and X represents a chlorine atom or a bromine atom. Izvest. Akad. Nauk S.S.S.R., Otdel. Khim. Nauk 1952, 261–7 discloses addition reactions between a thiophenol and a chlorotrifluoroethylene or a tetrafluoroethylene, as represented by formula (34''')

(34''')

wherein X represents a chlorine atom or a fluorine atom.

Bull. Soc. Chim. Fr., 1972, (8), 3202–5 discloses an addition reaction between a thiophenol and a chlorotrifluoroethylene as represented by formula (34'''').

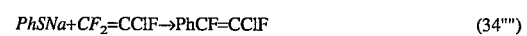

(34'''')

(2) Reactions between phenols or thiophenols and saturated fluorocarbons:

A number of reaction schemes are possible in the reaction of phenols or thiophenols with saturated fluorocarbons for producing fluorine-containing aromatic compounds. Representive examples of such reaction schemes include the following reactions:

(34)

(35)

wherein X represents an oxygen atom or a sulfur atom, $X^5$ and $X^6$ each independently represent a halogen atom, $-OSO_2Me$, $-OCOCF_3$,

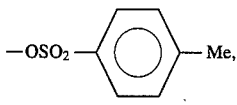

$-OSO_2CF_3$, $-OSO_2CCl_3$ or $-OSO_2Cl$, which are substituents readily liberated in the form of an anion, Ar' represents a monovalent aromatic group, and $R_f'$ has the same meaning as defined for $R_f$ of formula (A), which represents a group capable of assuming an anion structure of the formula $R_f'X'$.

Actual, Chem., 1987,151 discloses the reactions:

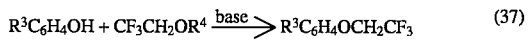

wherein $R^3$ represents a hydrogen atom, 4-Cl, 4-Br, 2-MeO$_2$C, 4-O$_2$N, 2-O$_2$N or 4-CF$_3$, $X_7$ represents a fluorine atom, a chlorine atom or a bromine atom, and $R_4$ represents $-SO_2Me$, $-COCF_3$, $-SO_2CCl_3$, $-SO_2C_6H_4Me-P$ or $-SO_2Cl$.

"Chemistry of Organic Fluorine Compounds" Halsted Press, 2nd Edition, P279 discloses a number of methods for synthesizing a fluorine-containing ether compound and a fluorine-containing thioether compound, in which an alcohol, a phenol or a thiol is alkylated at oxygen atom or sulfur atom portions thereof.

Journal of Organic Chemistry, 50, 4047 (1985) discloses the reaction:

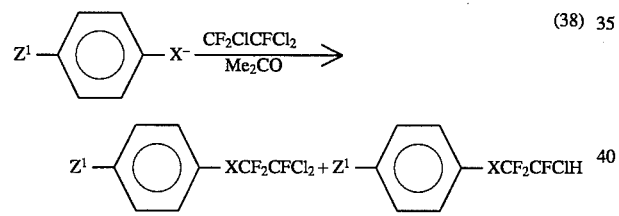

wherein $Z^1$ represents a hydrogen atom, a methyl group, a methoxy group or a chlorine atom, and X represents an oxygen atom or a sulfur atom.

Industrial and Engineering Chemistry, 39, 412 (1947) discloses the reactions:

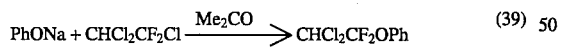

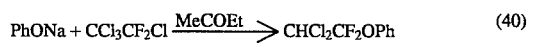

Tetrahedron Letters, 22, 323 (1981) discloses the reaction:

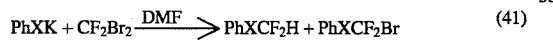

wherein X represents an oxygen atom or a sulfur atom.

Pure and Applied Chemistry, 59, 1015 (1987) discloses a number of reactions of various fluorine-containing halide compounds represented by formula (42) below with phenoxides.

wherein $Z^2$ represents a chlorine atom, a bromine atom or an iodine atom, and, $Z^3$ and $Z^4$ each represent a fluorine atom, a chlorine atom, a bromine atom, a CF$_3$ group or a hydrogen atom.

Examples of such reactions include the following reactions:

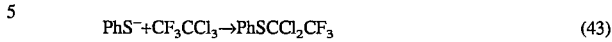

Journal of Organic Chemistry, 25, 2009 (1960) discloses the reaction:

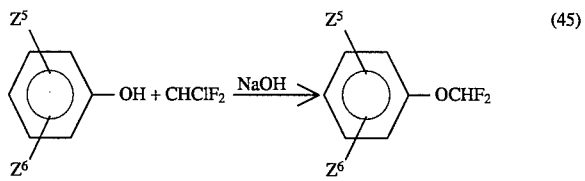

wherein $Z^5$ and $Z^6$ each represent a hydrogen atom, a methyl group, a methoxy group, a nitro group, a methyl group or a chlorine atom.

In addition, fluorine-containing aromatic compounds represented by formula (A) can be synthesized by the use of methods for forming various types of ether linkages and thioether linkages.

For example, an ether formation reaction comprising reacting a hydroxyl group with an epoxy group as indicated below, can be utilized:

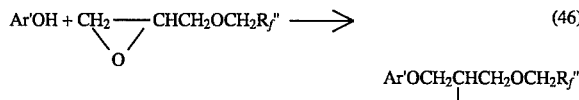

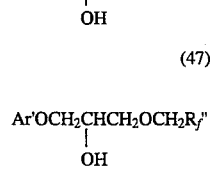

wherein Ar' represents a monovalent aromatic group, and $R_f''$ represents a fluorocarbon residue having from 1 to 16 carbon atoms.

Further, a method in which fluorine atom or atoms are introduced into a precursor of the compound represented by formula (A) by various methods, may be available, or a method in which reaction products obtained by the various methods described above are converted into a desired compound represented by formula (A) using various reactions, may be available.

For example, the following method can be mentioned, as disclosed in Actual. Chem., 1987, 151:

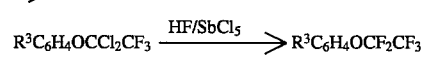

wherein $R^3$ has the same meaning as defined for R3 in formulae (36) and (37).

The fluorine-containing olefin and the fluorine-containing compound, such as a saturated fluorocarbon, each of which is to be used in the above-mentioned reactions, can be synthesized by various known methods.

For example, such methods include a synthetic method by halogen exchange disclosed in "Advances in Fluorine Chemistry" Butterworth, vol. 3, p181, a method disclosed in "Chemistry of Organic Fluorine Compounds" Halsted Press, and methods for producing fluoroolefin oligomers disclosed in Japanese Patent Application Laid-Open Specification No. 50-117705 and Japanese Patent Application Publication Specification Nos. 43- 11885 and 47-22563. The methods set out above are not limiting, and various other methods can be employed.

Preferred examples of compounds usable as the fluorine-containing aromatic compound (A) which exhibit excellent miscibility with an alkyl- or alkyl derivative-substituted aromatic hydrocarbon (B) are those in which the ratio of fluorine atoms to the sum of fluorine atoms and hydrogen atoms is from 0.03 to 0.85, preferably from 0.05 to 0.6, more preferably from 0.1 to 0.5. The above-mentioned fluorine-containing aromatic compounds (A) can be used individually or in combination.

With respect to various fluorine-containing aromatic compounds (A) usable in the present invention, especially preferred forms of compounds (A) are described below.

In formula (A-1), it is preferred that p and p' be 0 and 1, respectively, so that n-valent aromatic group represented by R of formula (A) is represented by the formula:

(A-1a)

wherein $Ar_1$, $Ar_4$, Y', l' and m' are as defined for formula (A-1).

In formula (A-1a), it is more preferred that each of l' and m' be 1, so that the n-valent aromatic group represented by R of formula (A) is represented by the formula:

$$Ar_1-Y'-Ar_4 \qquad (A-1b)$$

wherein $Ar_1$, $Ar_4$ and Y' are as defined for formula (A- 1).

In formula (A-1b), it is preferred that the linkage group Y' be a single bond, or a bivalent group selected from the group consisting of an oxygen atom (—O—), a sulfonyl group, a carbonyl group and an alkylene group having from 1 to 20 carbon atoms.

With respect to X of formula (A), an oxygen atom is most preferred.

Thus, a preferred illustrative example of the fluorine-containing aromatic compound (A) is represented by the formula:

(C-1)

wherein each of $R^1$ and $R^2$ independently represents a hydrogen atom or an alkyl group having from 1 to 19 carbon atoms, wherein the total number of carbon atoms in $R^1$ and $R^2$ is from 4 to 19, and each $R_f$ is as defined for formula (A), wherein the $R_f$ groups are the same or different.

In another preferred form of the n-valent R group of formula (A-1), p' be 0, so that the n-valent aromatic group represented by R of formula (A) is $Ar_1$ of formula (A-1), wherein $Ar_1$ is an aromatic nucleus substituted with at least one alkyl group having from 1 to 30 carbon atoms.

Thus, another preferred illustrative example of the fluorine-containing aromatic compound (A) is represented by the formula:

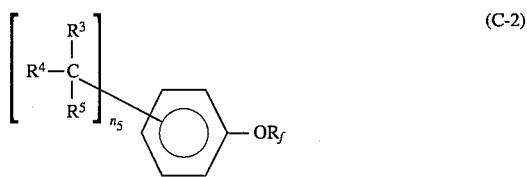

(C-2)

wherein each of $R^3$, $R^4$ and $R^5$ independently represents an alkyl group having from 1 to 20 carbon atoms, $n_5$ is an integer of from 1 to 3, the $R_f$ group is as defined for formula (A), wherein when $n_5$ is an integer of 2 or 3, the $R^3R^4R^5C$- groups are the same or different, and wherein the total number of carbon atoms of all $R^3R^4R^5C$- groups is from 4 to 25.

Among the fluorine-containing compounds (A) represented by formula (C-2), it is preferred to employ a fluorine-containing aromatic compound (A) represented by the formula:

(C-3)

wherein each of $R^6$, $R^7$ and $R^8$ independently represents an alkyl group having from 1 to 20 carbon atoms, and the $R_f$ group is as defined for formula (A), wherein the total number of carbon atoms of the $R^6R^7R^8C$- group is from 5 to 25.

With respect to the $R_f$ of formula (A), it is preferebly selected from the group consisting of a fluoroalkyl and a fluoroalkenyl group, each having from 1 to 10 carbon atoms. It is more preferred that the $R_f$ of formula (A) be a fluoroalkyl group having from 2 to 25 carbon atoms and having in a main chain thereof 1 to 7 ether linkages. It is also preferred that the $R_f$ of formula (A) represented by formula (A-2) is substituted with from 1 to 4 chlorine atoms. Preferred illustrative examples of the $R_f$ group of formula (A) include an unsubstituted fluoroalkyl group having from 1 to 3 carbon atoms, —CF=CFCF$_3$, —CF$_2$CFClH, —CF=CFCl, and —CF$_2$CHFO—(C$_3$F$_6$O—)$_n$CF$_2$CF$_2$CF$_3$, wherein n is an integer of from 0 to 6.

The above-mentioned fluorine-containing aromatic compounds represented by formulae (C-1), (C-2) and (C- 3) are extremely miscible with the alkyl- or alkyl derivative-substituted aromatic compound (B). Further, it should be noted that the miscibility of the fluorine-containing aromatic compounds (C-1), (C-2) and (C-3) with HFC and HFE refrigerants are not adversely affected even by mixing thereof with a large amount of the alkyl- or alkyl derivative-substituted aromatic compound (B). Therefore, the lubricant oil composition comprising the fluorine-containing aromatic compound of the formula selected from formulae (C-1), (C-2) and (C-3) and the alkyl- or alkyl derivative-substituted aromatic compound (B) has especially excellent properties, such as low temperature fluidity, low moisture absorption properties and high electrical insulation.

Furthermore, since the fluorine-containing aromatic compounds represented by formulae (C-1), (C-2) and (C-3) exhibit an extremely excellent miscibility with hydrocarbons, such compounds can be advantageously used as an additive in a refrigerant system using in combination an HFC refrigerant and a hydrocarbon lubricant, such as alkylbenzene or mineral oil (which is well-known to be unsatisfactory in miscibility with the HFC refrigerant), so that the oil return properties can be remarkably improved.

Another notable feature of the fluorine-containing compounds represented formulae (C-1), (C-2) and (C-3) resides in that the compounds exhibit low bioaccumulation (or low bioconcentration), so that these compounds can be safely used.

By virtue of the above-mentioned excellent properties of fluorine-containing compounds represented by formulae (C-1), (C-2) and (C-3), these compounds (even if used alone) are also advantageously useful not only as lubricant oils for refrigeration equipment using HFC refrigerants but also as lubricants for general purpose, or additives or modifiers for various types of oily substances and polymeric materials.

With respect to the alkyl- or alkyl derivative-substituted aromatic compound (B) which can be used in the present invention, there is no particular limitation as long as it is an oily material which satisfies the above-mentioned requirements. However, from the viewpoint of ease in handling, it is preferred that the compound (B) have a kinetic viscosity of from 0.1 to 500 cSt, preferably from 1 to 300 cSt, more preferably from 3 to 100 cSt as measured at 40° C.

The number of the at least one substituted aromatic nucleus in the compound (B) is preferably in the range from 1 to 4, more preferably 1 or 2, most preferably 1. When the number of the substituted aromatic nucleus in the compound (B) is 5 or more, the viscosity of the compound (B) tends to become too With respect to the proportion of the aromatic nucleus in the compound (B), it is preferred that the ratio of carbon atoms in the aromatic nucleus of the compound (B) to all carbon atoms in the compound (B) be in the range from 0.10 to 0.95. This ratio is more preferably in the range from 0.15 to 0.9, still more preferably from 0.20 to 0.8. When the ratio of carbon atoms in the aromatic nucleus of the compound (B) to carbon atoms in the compound (B) is less than 0.10, the miscibility of the compound (B) with the fluorine-containing aromatic compound (A) tends to be lowered, or the miscibility of the lubricant oil composition comprising the compound (A) and the compound (B) with a hydrofluorocarbon refrigerant or a hydrofluoroether refrigerant tends to be lowered. On the other hand, when the ratio of carbon atoms in the aromatic nucleus of the compound (B) to carbon atoms in the compound (B) is more than 0.95, the compound (B) tends to be likely to crystallize even around room temperature.

It is preferred that the unsubstituted or substituted alkyl group as the substituent of the compound (B) have from 1 to 30, preferably from 4 to 25 carbon atoms.

Examples of derivatives of the at least one substituted aromatic nucleus of the compound (B) include one in which at least two substituted aromatic nuclei selected from the group consisting of a substituted benzene nucleus and a substituted naphthalene nucleus are linked through a linkage group to form a multinuclear structure. The linkage group can be selected from the group consisting of a single bond and a bivalent group, such as an alkylene group, an ether group, an ester group, a carbonate group, a carbonyl group or a sulfonyl group. The derivative of the at least one aromatic nucleus of the compound (B) may be further substituted.

A preferred form of the alkyl- or alkyl derivative-substituted aromatic compound (B) is described below.

The preferred form of the alkyl- or alkyl derivative-substituted aromatic compound (B) is represented by the formula:

(B-1)

wherein:
each of $Ar_a$ and $Ar_b$ independently represents a benzene nucleus or a naphthalene nucleus,
$n_1$ is an integer of from 0 to 4, preferably from 1 to 3,
$n_2$ is an integer of from 0 to 3, preferably 1 or 2,
$n_3$ is an integer of from 1 to 3, preferably 1 or 2, most preferably 1,
$n_4$ is an integer of from 0 to 2, with the proviso that when $n_4$ is zero, $n_1$ is not zero and that when $n_4$ is not zero, $(n_1+n_2)$ is not zero,
K is a linkage group selected from the group consisting of:
  1) a single bond,
  2) a bivalent group selected from the group consisting of an oxygen atom (—O—), a sulfonyl group and a carbonyl group, which is preferably —O—, and
  3) an unsubstituted or substituted saturated hydrocarbon group having from 1 to 12 carbon atoms, preferably from 1 to 4 carbon atoms, most preferably 1 carbon atom and having a valence of from 2 to 4, preferably a valence of 2, and each of $R_1$ and $R_2$ independently represents an unsubstituted or fluorine-substituted alkyl group having from 1 to 30 carbon atoms, preferably from 4 to 25 carbon atoms, wherein a main chain of the unsubstituted or fluorine-substituted alkyl group optionally has at least one ether linkage introduced therein or to a terminal thereof, with the proviso that the ratio of the at least one ether linkage to all carbon atoms of the alkyl- or alkyl derivative-substituted aromatic compound of formula (B-1) is not more than ⅓, preferably not more than ⅕, wherein when $n_1$ is an integer of 2 to 4, the $R_1$ groups are the same or different; when $n_2$ is an integer of 2 or 3, the $R_2$ groups are the same or different; when $n_3$ is an integer of 2 or 3, the $R_2$ groups are the same or different and the $Ar_b$ groups are the same or different; and when $n_4$ is 2, the K groups are the same or different, the $R_2$ groups are the same or different and the $Ar_b$ groups are the same or different, wherein the alkyl- or alkyl derivative-substituted aromatic compound of formula (B-1) optionally has at least one hydrogen atom replaced with a polar group at a ratio of not more than ⅓, preferably not more than ⅕ relative to all hydrogen atoms of said alkyl- or alkyl derivative-substituted aromatic compound of formula (B-1), the polar group being selected from the group consisting of a chlorine atom, an unsubstituted or substituted amino group, an acyl group, an acyloxy group, a carboalkoxy group and a nitrile group.

The alkyl- or alkyl derivative-substituted aromatic compound (B) optionally has at least one hydrogen atom replaced with a fluorine atom at a ratio of not more than ½ relative to all hydrogen atoms of the alkyl- or alkyl derivative-substituted aromatic compound (B). Examples of such fluorine-substituted compound (B) include 2,2,2-trifluoroethyl-substituted aromatic compounds, 3,3,3-trifluoropropyl-substituted aromatic compounds, and various fluorine-substituted alkyl benzenes, such as $CF_3CHFCF_2$-substituted alkyl benzenes.

When the compound (B) has an alkoxy group substituted with a fluorine atom, it is preferred that the ratio of fluorine atom in the fluoroalkoxy group to carbon atom in the fluoroalkoxy group be less than 0.6.

In the compound (B) represented by formula (B-1), at least two carbon atoms which are not a part of the aromatic nucleus may be linked through a single or double bond to form a ring structure.

In the lubricant oil composition of the present invention, two or more types of the compound (B) may be employed in combination.

The compound (B) may be employed in a mixed form with a non-aromatic hydrocarbon compound. When the compound (B) is employed in a mixed form with a non-aromatic hydrocarbon compound, the weight ratio of the compound (B) to the non-aromatic hydrocarbon compound is preferably 0.5 or more, more preferably 1.0 or more.

Illustrative examples of the alkyl- or alkyl derivative-substituted aromatic compound (B) are described below. Representative examples of substituted aromatic compounds usable as the compound (B) include alkylbenzenes, alkylnaphthalenes, derivatives of alkylbenzenes, such as an alkylated biphenyl, a polyphenyl-substituted hydrocarbon and styrene oligomer, and derivatives of alkylnaphthalenes. From the viewpoint of economy, preferred is an alkylbenzene, which can be obtained at a low price. Examples of alkylbenzenes include a monoalkylbenzene, a dialkylbenzene, and a polyalkylbenzene having at least 3 alkyl groups as substituents. Of alkylbenzenes, a monoalkylbenzene and a dialkylbenzene, which are easily available, are preferred from the commercial viewpoint. As an alkylbenzene, any of a (branched) alkylbenzene and a (linear) alkylbenzene can be employed. A (branched) alkylbenzene is preferred to a (linear) alkylbenzene since the (branched) alkylbenzene exhibits a particularly good miscibility with a hydrofluorocarbon as a refrigerant. Of (branched) alkylbenzenes, those having at least one branched alkyl group having from 3 to 30 carbon atoms are preferred.

More specific examples of the alkyl- or alkyl derivative-substituted aromatic compound (B) are described below.

Such specific examples of the compound (B) include:
a (branched) alkylbenzene represented by the formula:

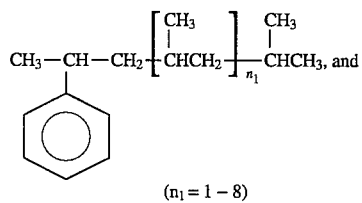

$(n_1 = 1 - 8)$ (linear) alkylbenzenes respectively represented by the following formulae:

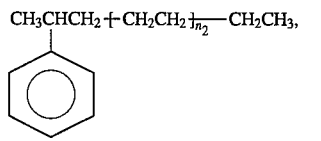

$(n_2 = 3 - 10)$

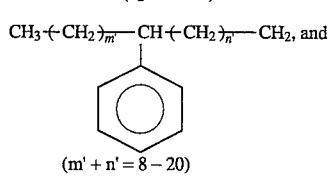

$(m' + n' = 8 - 20)$

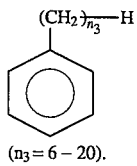

$(n_3 = 6 - 20)$.

More specific examples of the compound (B) also include those respectively represented by the following formulae:

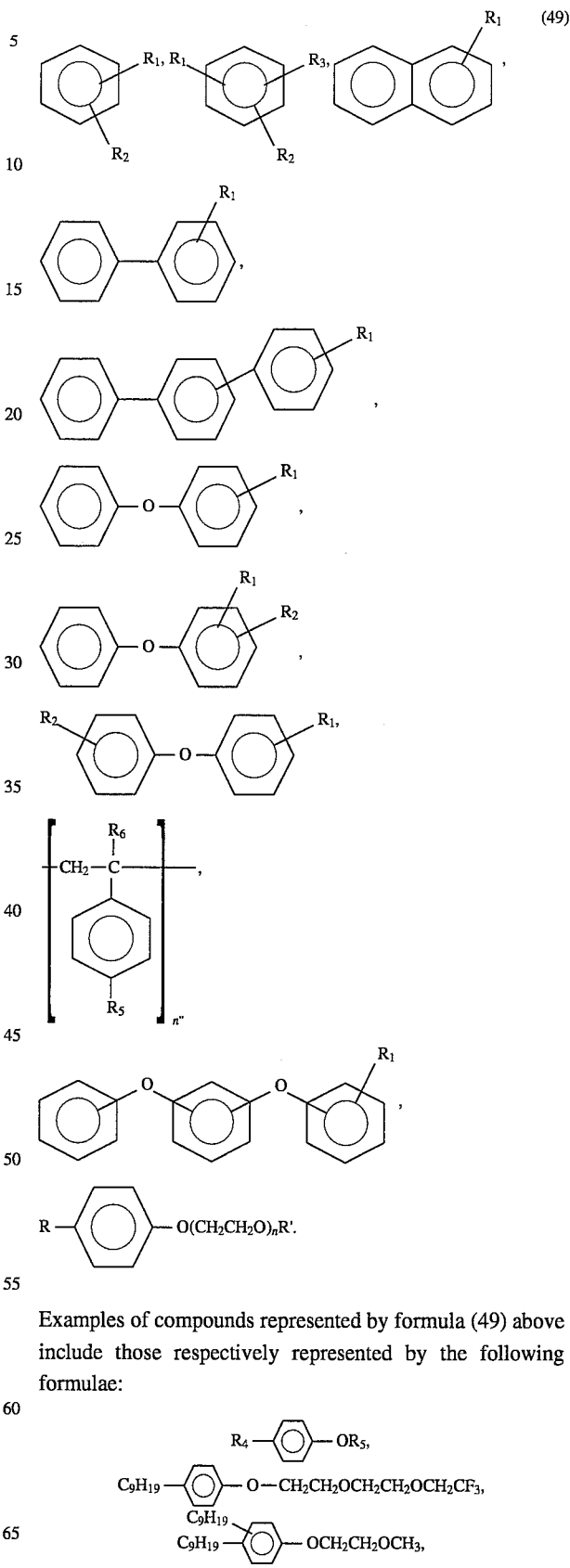

Examples of compounds represented by formula (49) above include those respectively represented by the following formulae:

-continued

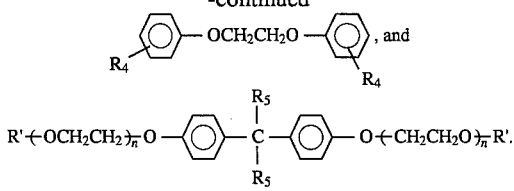

More illustrative examples of the compound (B) also include those respectively represented by the following formulae:

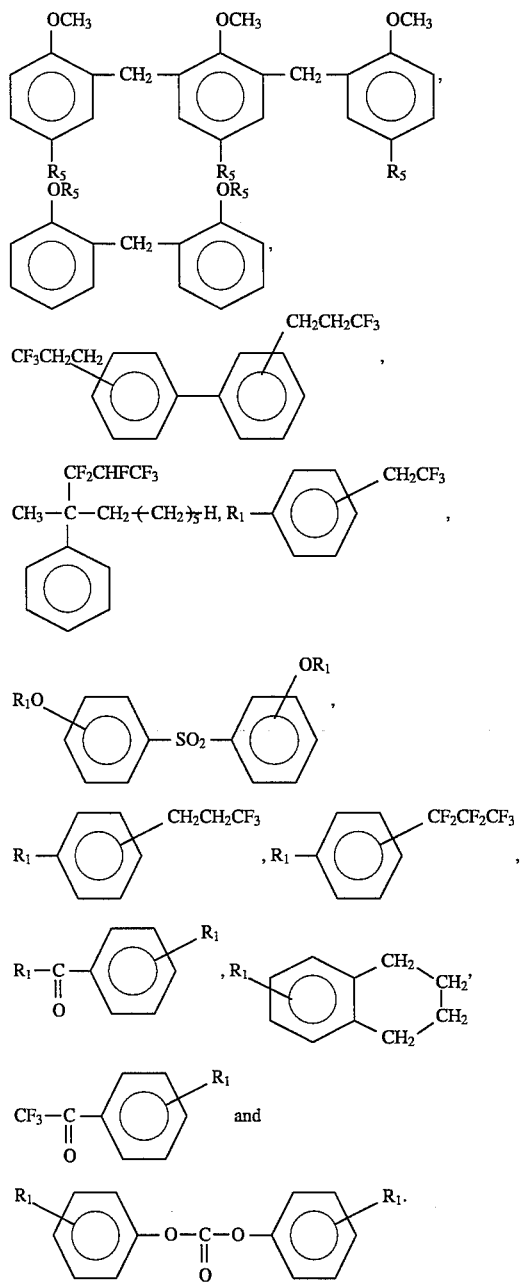

In the above-mentioned formulae representing more illustrative examples of the compound (B):

R represents a hydrogen atom or an alkyl group having 1 to 30, preferably 4 to 25 carbon atoms, R' represents a hydrogen atom, an alkyl group having 1 to 10, preferably 1 to 5 carbon atoms, an aralkyl group having 7 to 20, preferably 7 to 10 carbon atoms, an aryl group having 6 to 20, preferably 6 to 14 carbon atoms or a halogen-substitution product thereof, each of $R_1$, $R_2$ and $R_3$ represents an alkyl group having 6 to 30, preferably 8 to 25 carbon atoms, $R_4$ represents an alkyl group having 4 to 20 carbon atoms, $R_5$ represents an alkyl group having 1 to 10 carbon atoms, $R_6$ represents a hydrogen atom or —$CH_3$, n represents an integer of from 0 to 10, preferably 1 to 6, more preferably 1 to 3, m' represents an integer of from 1 to 19, n' represents an integer of from 1 to 19, m' +n' is an integer of from 8 to 20, $n_1$ represents an integer of from 1 to 8, $n_2$ represents an integer of from 3 to 10, $n_3$ represents an integer of from 6 to 20, and n" represents an integer of from 2 to 4.

Each of commercially available alkylbenzene products usable as the compound (B) is usually a mixture of a plurality of types of alkylbenzenes.

In the lubricant oil composition of the present invention comprising the fluorine-containing aromatic compound (A) and the alkyl- or alkyl derivative-substituted aromatic compound (B), the fluorine-containing aromatic compound (A) is present in an amount of from 0.1 to 99.9% by weight, preferably from 1 to 99% by weight, more preferably from 5 to 95% by weight, most preferably from 10 to 90% by weight, based on the total weight of the fluorine-containing aromatic compound (A) and the alkyl- or alkyl derivative-substituted aromatic compound (B). When the ratio of the compound (A) is less than 0.1% by weight as the lower limit, the miscibility of the lubricant oil composition with a hydrofluorocarbon refrigerant or a hydrofluoroether refrigerant cannot be satisfactorily improved, and the lubricating properties of the lubricant oil composition for these refrigerants cannot also be satisfactorily improved. On the other hand, when the ratio of the compound (A) is more than 99.9% by weight as the upper limit, the low temperature flowability, the low moisture absorption properties, electrical insulation properties and the like cannot be satisfactorily improved.

In the lubricant oil composition of the present invention comprising the fluorine-containing aromatic compound (A) and the alkyl- or alkyl derivative-substituted aromatic compound (B), when the compound (A) is present in a relatively high amount, for example, from 40 to 99.9% by weight, preferably 60 to 99.9% by weight, even when it is employed in combination with a hydrofluorocarbon refrigerant or a hydrofluoroether refrigerant, a homogeneous refrigerant composition can be obtained over a wide temperature range.

On the other hand, when the compound (B) is present in a relatively high amount in the lubricant oil composition of the present invention comprising the compound (A) and the compound (B), and the lubricant oil composition is employed in combination with a hydrofluorocarbon refrigerant or a hydrofluoroether refrigerant, it is possible that a part of the refrigerant composition, which part is composed mainly of the compound (B), undergoes a phase separation depending on use conditions. However, since the compound (A) exhibits excellent affinity to any of the compound (B) and a refrigerant, such as a hydrofluorocarbon refrigerant and a hydrofluoroether refrigerant, even when a lubricant oil composition of the present invention having a relatively high ratio of the compound (B) is used, the compound (A) effectively serves as an agent for facilitating oil return to the compressor. Therefore, such a lubricant oil composition having a relatively high ratio of the component (B) can be advantageously used. For improving oil return to the compressor, the amount of the compound (A) in the lubricant oil composition comprising the compound (A) and the compound (B) is preferably 5% by weight or more, more preferably 10% by weight or more, still more preferably 40% by weight or more, based on the total weight of the compound (A) and the compound (B). The larger the amount of the compound (A), the more the improvement in oil return to the compressor can be achieved. Therefore, a preferred upper limit of the amount of the compound (A) for improving oil return to the compressor is not particularly limited as long as the amount of the compound (A) is not larger than 99.9% by weight, based on the total weight of the compound (A) and the compound (B). For improving the lubricating properties of the lubricant oil composition of the present invention, the amount of the compound (A) is from 0.1 to 99.9%, preferably from 1 to 99% by weight, more preferably from 10 to 90% by weight, based on the total weight of the compound (A) and the compound (B).

The compound (B) has a kinetic viscosity of from 0.1 to 500 cSt, preferably from 1 to 300 cSt, more preferably from 3 to 100 cSt as measured at 40° C. With respect to the kinetic viscosity of the compound (A), there is no particular restriction. The lubricant oil composition of the present invention comprising the compound (A) and the compound (B) has a kinetic viscosity as measured at 40° C. of from 2 to 500 cSt, preferably from 3 to 300 cSt, more preferably from 5 to 150 cSt. When the kinetic viscosity of the lubricant oil composition is too low, satisfactory lubricating properties in the compressor cannot be achieved. When the kinetic viscosity of the lubricant oil composition is too high, the revolution torque in the compressor becomes disadvantageously high.

The compound (A) may be in a solid form as long as the kinetic viscosity of the lubricant oil composition comprising compound (A) and compound (B) is within the range from 2 to 500 cSt as measured at 40° C. A conventional lubricant oil may optionally be added to the lubricant oil composition of the present invention, and in such a case, there is no particular limitation on the kinetic viscosity of the conventional lubricant oil to be added, as long as the kinetic viscosity of the composition of the present invention having the conventional lubricant oil added thereto is within the above-mentioned range from 2 to 500 cSt as measured at 40° C.

In another aspect of the present invention, there is provided a refrigerant composition comprising the lubricant oil composition of the present invention, and at least one refrigerant selected from the group consisting of a hydrofluorocarbon and a hydrofluoroether, wherein the weight ratio of the lubricant oil composition to the at least one refrigerant is 99/1 to 1/99, preferably 95/5 to 5/95, more preferably 90/10 to 10/90.

Examples of hydrofluorocarbon refrigerants usable with the lubricant oil composition of the present invention to provide the refrigerant composition of the present invention include a hydrofluorocarbon having from 1 to 5 carbon atoms, preferably from 1 to 4 carbon atoms. Representative examples of such hydrofluorocarbons include fluoromethanes, such as HFC-32 ($CH_2F_2$), fluoroethanes, such as HFC-134a ($CF_3CH_2F$), HFC-134 ($CHF_2CHF_2$), HFC-143a ($CF_3CH_3$), HFC-152a ($CH_3CHF_2$), and HFC-125 ($CF_3CHF_2$), fluoropropanes, such as $CF_3CH_2CHF_2$, $CF_3CHFCF_3$, $CHF_2CF_2CHF_2$, $CF_3CF_2CF_3$, $CF_3CF_2CH_3$, and $CHF_2CF_2CH_2F$, fluorobutanes, such as $CF_3CF_2CF_2CH_3$ and $CF_3CHFCHFCF_3$, fluoropentanes, such as $CF_3CHFCHFCF_2CF_3$. These hydrofluorocarbons can be used individually or in combination.

When the above-mentioned hydrofluorocarbon refrigerants are used in combination, preferred examples of mixed hydrofluorocarbon refrigerants include HFC-32/HFC-125, HFC-32/HFC-134a, HFC-32/HFC-125/HFC-134a, HFC-32/HFC-125/HFC-290(propane)/HFC-134a, HFC-125/HFC-134a, HFC-125/HFC-143a, HFC-125/HFC-143a/HFC-134a and HFC-32/HFC-125/HFC-143a. The above mixed refrigerants are promising as substitute refrigerants for replacing HCFC-22.

Furthermore, a mixed refrigerant containing a chlorine-containing fluorocarbon, such as HCFC-22 ($CHClF_2$) or CFC-12 ($CCl_2F_2$), in addition to a hydrofluorocarbon, can also be used in the refrigerant composition of the present invention. In the mixed refrigerant comprised of a chlorine-containing fluorocarbon and a hydrofluorocarbon, the chlorine-containing fluorocarbon is used in an amount of from 0.01 to 80% by weight, preferably from 0.01 to 60% by weight, more preferably from 0.01 to 40% by weight.

When a conventional lubricant oil, such as polyalkyleneglycol or an ester oil, is contacted with a chlorine-containing refrigerant, even if the amount of the chlorine-containing refrigerant is small, the decomposition of the lubricant oil is accelerated, so that the lubricant oil cannot be practically used in the presence of a chlorine-containing refrigerant. By contrast, the lubricant oil composition of the present invention is stable even in the presence of a chlorine-containing refrigerant. Therefore, for example, the lubricant oil composition of the present invention is promising for use in retrofitting a conventional compressor employing a chlorine-containing refrigerant. (The term "retrofitting" used herein means to renew a compressor simply by replacing the refrigerant and the lubricant oil employed therein with new ones.)

It has been found that the lubricant oil composition of the present invention exhibits excellent miscibility not only with a hydrofluorocarbon refrigerant, but also with a hydrofluoroether refrigerant which is attracting attention because a hydrofluoroether has a global warming potential advantageously lower than that of a hydrofluorocarbon.

As a hydrofluoroether refrigerant, various hydrofluoroethers can be used. However, from the viewpoint of lowering the global warming potential, it is preferred that the sum of the number of carbon atoms and the number of oxygen atoms of the hydrofluoroether be from 3 to 6. From this viewpoint, it is also preferred that the hydrofluoroether have at least one hydrogen atom in the molecule thereof. Examples of hydrofluoroether refrigerants usable in the refrigerant composition of the present invention include the following compounds:

$CF_3$—O—$CHF_2$, $CF_3$—O—$CH_2F$, $CF_3$—O—$CH_3$, $CHF_2$—O—$CHF_2$, and $CHF_2$—O—$CH_2F$;

$CF_3$—O—$CF_2$—$CHF_2$, $CF_3$—O—$CF_2$'$CH_2F$, $CF_3$—O—$CF_2$—$CH_3$, $CF_3$—O—$CHF$—$CF_3$, $CF_3$—O—$CHF$—$CHF_2$, $CF_3$—O—$CHF$—$CH_2F$, $CF_3$—O—$CHF$—$CH_3$, $CF_3$—O—$CH_2$—$CF_3$, $CF_3$—O—$CH_2$—$CHF_2$, $CF_3$—O—$CH_2$—$CH_2F$, and $CF_3$—O—$CH_2$—$CH_3$;

$CHF_2$—O—$CF_2$—$CF_3$, $CHF_2$—O—$CF_2$—$CHF_2$, $CHF_2$—O—$CF_2$—$CH_2F$, $CHF_2$—O—$CF_2$—$CH_3$, $CHF_2$—O—$CHF$—$CF_3$, $CHF_2$—O—$CHF$—$CHF_2$, $CHF_2$—O—$CHF$—$CH_2F$, $CHF_2$—O—$CHF$—$CH_3$, $CHF_2$—O—$CH_2$—$CF_3$, $CHF_2$—O—$CH_2$—$CHF_2$, and $CHF_2$—O—$CH_2$—$CH_2F$;

$CH_2F$—O—$CF_2CF_3$, $CH_2F$—O—$CF_2$—$CHF_2$, $CH_2F$—O—$CF_2$—$CH_2F$, $CH_2F$—O—$CF_2$—$CH_3$ $CH_2F$—O—$CHF$—$CF_3$, $CH_2F$—O—$CHF$—$CHF_2$, $CH_2F$—O—$CHF$—$CH_2F$, $CH_2F$—O—$CH_2$—$CF_3$, and $CH_2F$—O—$CH_2$—$CHF_2$;

$CH_3$—O—$CF_2$—$CF_3$, $CH_3$—O—$CF_2$—$CHF_2$, $CH_3$—O—$CF_2$—$CH_2F$, $CH_3$—O—CHF—$CF_3$, $CH_3$—O—CHF—$CHF_2$, and $CH_3$—O—$CH_2$—$CF_3$;
$CH_3$—O—$CH_2CF_2CF_3$, $CH_3$—O—$CF_2CHFCF_3$, $CH_3CH_2$—O—$CF_2$—$CHF_2$, $CF_3CH_2$—O—$CH_2$—$CF_3$, $CF_3CF_2$—O—$CF_2CF_3$, $CF_3CF_2CF_2$—O—$CHFCF_3$, $(CF_3)_2CHCF_2$—O—$CH_3$, and $CF_3CF_2CH_2$—O—$CF_2CHF_2$; and
$CF_3$—O—$CF_2CF_2$—O—$CH_3$.

In the lubricant oil composition to be employed in the refrigerant composition of the present invention, as mentioned above, it is especially preferred to employ the fluorine-containing aromatic compound (A) represented by the formula:

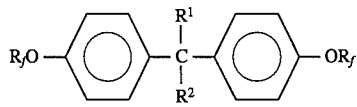
(C-1)

wherein each of $R^1$ and $R^2$ independently represents a hydrogen atom or an alkyl group having from 1 to 19 carbon atoms, wherein the total number of carbon atoms in $R^1$ and $R^2$ is from 4 to 19, preferably from 5 to 16, more preferably from 5 to 12, and each $R_f$ is as defined for formula (A), wherein the $R_f$ groups are the same or different.

In the lubricant oil composition to be employed in the refrigerant composition of the present invention, it is also preferred to employ the fluorine-containing aromatic compound (A) represented by the formula:

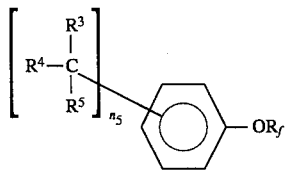
(C-2)

wherein each of $R^3$, $R^4$ and $R^5$ independently represents an alkyl group having from 1 to 20 carbon atoms, $n_5$ is an integer of from 1 to 3, the $R_f$ group is as defined for formula (A), wherein when $n_5$ is an integer of 2 or 3, the $R^3R^4R^5C$- groups are the same or different, and wherein the total number of carbon atoms of all $R^3R^4R^5C$- groups is from 4 to 25.

With respect to the formula (C-1), when the total number of carbon atoms in $R^1$ and $R^2$ is 3 or less, the bioaccumulation of the compound (A) represented by the formula (C-1) is disadvantageously high. On the other hand, when the total number of carbon atoms in $R^1$ and $R^2$ is 20 or more, the miscibility of the compound (A) represented by the formula (C-1) with a hydrofluorocarbon refrigerant, such as HFC-134a, or a hydrofluoroether refrigerant is low, and also the availability of the material to be used for producing the compound (A) represented by the formula (C-1) is very low. From the viewpoint of increasing stability, it is preferred that each of $R^1$ and $R^2$ in the formula (C-1) be an alkyl group, but not a hydrogen atom.

With respect to the formula (C-2), when the total number of carbon atoms of all $R^3R^4R^5C$— group is 3 or less, the bioaccumulation of the compound (A) represented by the formula (C-2) is disadvantageously high. On the other hand, when the total number of carbon atoms of all $R^3R^4R^5C$— groups is 26 or more, the miscibility of the compound (A) represented by the formula (C-2) with a hydrofluorocarbon refrigerant, such as HFC-134a, or a hydrofluoroether refrigerant is low, and also the availability of the material to be used for producing the compound (A) represented by the formula (C-2) is very low.

With respect to $R^1$ and $R^2$ of the formula (C-1) and $R^3$, $R^4$ and $R^5$ of the formula (C-2), each may independently have a substituent group and/or a linkage group. Examples of these substituent and linkage groups include unsaturated hydrocarbon groups; halogen atoms, such as a chlorine atom and a fluorine atom; and various polar groups containing oxygen, nitrogen, phosphorus or sulfur, such as a hydroxyl group, a thiol group, an alkoxy group, a nitrile group, a nitro group, an ether group, a thioether group, an ester group, a carbonyl group, a sulfonyl group, a sulfinyl group, a carboxyl group, a carboxylate group, an amino group, a thiocarbamate group, an amido group, an imido group, a pyridine group, a pyrimidine group, a piperidine group, a triazine group, a phosphine group, a benzoimidazole group, a phosphorous ester group, a triazole group, a tetrazole group, a thiazole group, and a thiadiazole group. Of them, a fluorine atom and an ether group are preferred from the viewpoint of improving stability. The number of such substituent group and/or linkage group in each of $R^1$, $R^2$, $R^3$, $R^4$ and $R^5$ is preferably 5 or less, more preferably 3 or less, still more preferably 1 or less.

Examples of the compounds (A), particularly represented by formula (C-1), include the following compounds:

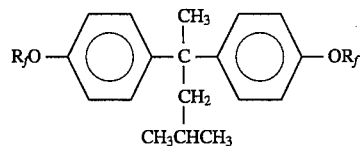

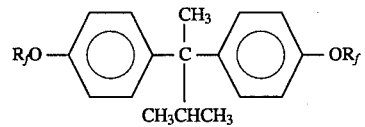

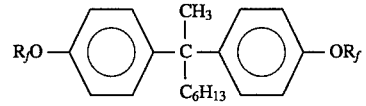

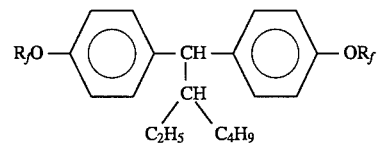

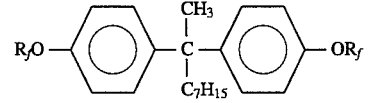

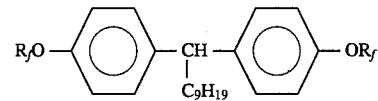

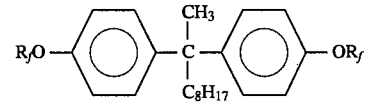

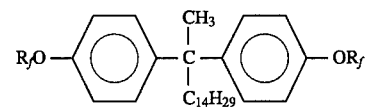

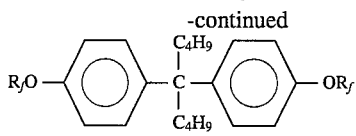

Examples of the compounds (A), particularly represented by formula (C-2), include the following compounds:

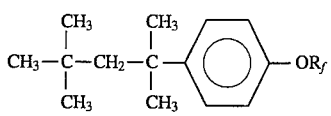
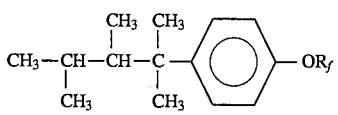
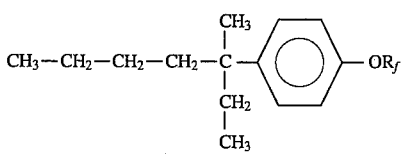
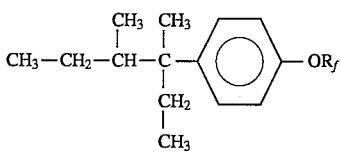
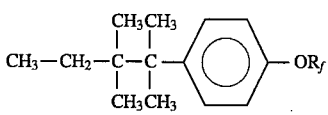
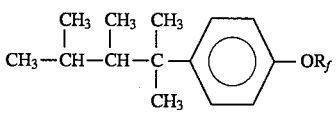
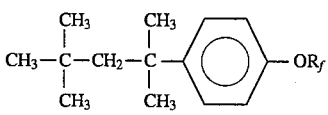
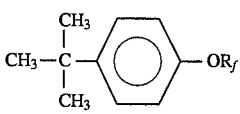
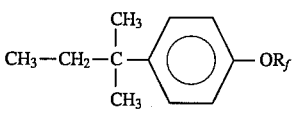
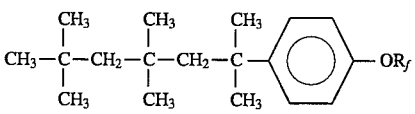
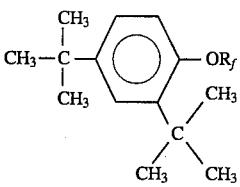

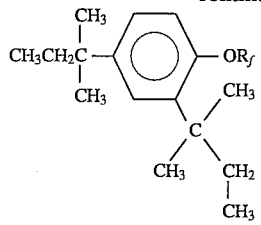
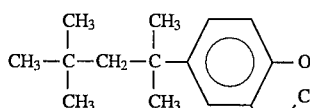
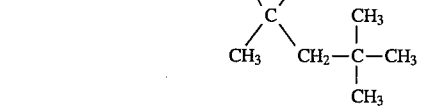

$R_f$ of the formulae (C-1) and (C-2) represents an unsubstituted or partially substituted fluorocarbon group, which is as defined for formula (A). The term "fluorocarbon group" means a hydrocarbon group which is partially or entirely substituted with at least one fluorine atom.

The ratio of fluorine atom or atoms to carbon atom or atoms in $R_f$ is from 0.6 to 3, preferably from 1 to 3, and more preferably from 1.5 to 3.

When the atomic ratio of fluorine to carbon in $R_f$ is lower than 0.6, the miscibility of the compound (A) represented by the formula (C-1) or (C-2) with a hydrofluorocarbon refrigerant is likely to become poor. In addition, the stability of the compound (A) is likely to become poor.

The number of carbon atoms contained in $R_f$ is from 1 to 25, preferably from 1 to 10, more preferably from 1 to 3.

$R_f$ may be a fluoroalkyl group having from 1 to 10 carbon atoms or a fluoroalkenyl group having from 1 to 10 carbon atoms. Examples of these fluoroalkyl groups and fluoroalkenyl groups include —$C_6F_{11}$, —$C_6F_{12}H$, —$C_9F_{17}$, and —$C_9F_{18}H$. Examples of fluoroalkyl groups having from 1 to 3 carbon atoms include —$CF_2H$, —$CF_3$, —$CF_2CF_2H$, —$CF_2CF_3$, —$CH_2CF_3$, —$CF_2CHFCF_3$, and —$CF_2CF_2CF_3$. Further, $R_f$ may be a fluoroalkyl group having from 2 to 25 carbon atoms and having from 1 to 7 ether linkages in a main chain thereof. Furthermore, $R_f$ may be a fluorocarbon group of the formula (A-2) which is substituted with 1 to 4 chlorine atoms. Especially preferred examples of $R_f$ include an unsubstituted fluoroalkyl group having from 1 to 3 carbon atoms, —$CF$=$CFCF_3$, —$CF_2CFClH$, —$CF$=$CFCl$, and —$CF_2CHFO$—$(C_3F_6O)_nCF_2CF_2CF_3$, wherein n is an integer of from 0 to 6.

When $R_f$ has more than 25 carbon atoms, it becomes difficult to procure or synthesize the raw material for producing the compound (A), and also the synthesis and purification of the compound (A) become cumbersome.

With respect to each of the compounds (A) of formulae (C-1) and (C-2), for improving the miscibility with the compound (B), the ratio of fluorine atoms to the total number of fluorine and hydrogen atoms in each of the compounds (A) of formulae (C-1) and (C-2), is preferably in the range from 0.03 to 0.85, more preferably from 0.05 to 0.6, still more preferably from 0.1 to 0.5.

With respect to each of fluorine-containing aromatic compounds (A) of formulae (C-1) and (C-2), a plurality of types can be used in the form of a mixture as the compound (A) to be mixed with the compound (B) to provide the lubricant oil composition of the present invention.

Among the compounds falling in the definition of the compound (A), especially the compounds (C-1) and (C-2) have a good miscibility with hydrocarbons. Examples of hydrocarbons include (1) mineral oils, such as paraffin mineral oil and naphthene mineral oil; (2) olefin (co)polymers; and (3) aromatic hydrocarbons, such as alkylbenzene, alkylnaphthalene, alkylated biphenyl, polyphenyl-substituted hydrocarbon, and stylene oligomer (the aromatic hydrocarbons including the alkyl- or alkyl derivative-substituted aromatic compound (B)). Therefore, the compounds (C-1) and (C- 2) can be advantageously used in a mixed form with above-mentioned hydrocarbon oils.

Since the compounds (A) of formulae (C-1) and (C- 2) exhibit an especially good miscibility with the alkyl- or alkyl derivative-substituted aromatic compound (B), such as alkylbenzene, even when the compounds (A) of formula (C-1) and (C-2) are mixed, individually or in mixture thereof, with a large amount of the compound (B) to provide the lubricant oil composition of the present invention, the good miscibility of the compound (A) with a hydrofluorocarbon refrigerant is not sacrificed, and the resultant lubricant oil composition is effectively improved in physical properties, such as low temperature fluidity, low moisture absorption properties, and electrical insulation properties.

Further, the compounds (A) of formulae (C-1) and (C-2) exhibit good miscibility with any of a hydrocarbon and a hydrofluorocarbon, so that they can be used as an effective additive for facilitating oil return to the compressor in a refrigeration system employing a lubricant oil composed of a hydrocarbon, such as mineral oil or an aromatic hydrocarbon, such as alkylbenzene or its derivatives.

A lubricant oil composition of the present invention obtained by mixing the compounds (A) of formulae (C-1) and/or (C-2) with the compound (B) is a very excellent lubricant oil as evaluated from the practical viewpoint since it is extremely improved in all of the properties required for a lubricant oil, such as miscibility with HFC refrigerants, low temperature fluidity, low moisture absorption properties, electrical insulating properties and lubricating properties.

The fluorine-containing aromatic compounds (A) of formulae (C-1) and (C-2) have an especially excellent stability. As disclosed in Japanese Patent Application Laid-Open Specification No. 5-86382, a conventional lubricant oil composed of nonylphenol or dodecylphenol which are represented by the below-indicated formulae, undergoes oxidation and heat decomposition when heated in the air.

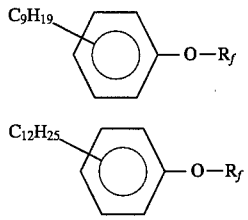

By contrast, the compounds (A) of formulae (C-1) and (C-2) are not decomposed even when heated at 175 ° C. in the air for a long period of time.

When the compounds (A) of formulae (C-1) and (C-2) are subjected to testing for stability in which the compounds (A) of formulae (C-1) and (C-2) are heated, individually or in mixture thereof, in the presence of a metal, such as copper, brass, aluminum or carbon steel and in the presence of an HFC refrigerant, such as HFC-134a, excellent results are obtained such that all of the compounds (A) of formulae (C-1) and/or (C-2) and the HFC refrigerant are stable even at 175° C. and that the surface of the metal does not show any appreciable change.

Further, when a lubricant oil composition prepared by mixing the compounds (A) of formulae (C-1) and/or (C-2) with the compound (B) is subjected to the same stability testing as mentioned above, excellent results are also obtained such that all of the compound (A), the compound (B) and the HFC refrigerant are stable, and that the surface of the metal does not show any appreciable change.

The compounds (A), especially represented by formulae (C-1) and (C-2), exhibit low moisture absorption properties. Further, it should be noted that when the compounds (A) of formulae (C-1) and (C-2) are mixed, individually or in mixture thereof, with the compound (B), a moisture absorption of the resultant lubricant oil composition is further remarkably lowered, so that the composition is free from problems, which have hitherto been caused by the presence of water in the refrigeration system, such as water freezing, metal corrosion and accelerated hydrolysis of an HFC refrigerant, such as HFC-134a.

Furthermore, it should be noted that when the compounds (A) of formulae (C-1) and (C-2) are mixed, individually or in mixture thereof, with the compound (B), a lowering of volume resistivity, which has been frequently caused due to moisture absorption, can be markedly prevented.

When a chemical substance is released in the natural environment (hydrosphere, pedosphere and atmosphere), the more stable the substance, the greater the probability that the substance will be in contact with living organisms. Accordingly, a relatively stable substance is likely to be taken and accumulated in living organisms, thereby polluting the organisms. From the standpoint of environmental toxicology, the present inventors have made studies. As a result, it has been found that the degree of bioaccumulation, i.e., bioconcentration, is low with respect to the compounds (A), particularly represented by formulae (C-1) and (C-2) including (C-3).

Further, the lubricating properties of each of the fluorine-containing compounds (A) of formulae (C-1) and (C-2) have been evaluated in the presence or absence of a hydrofluorocarbon. As a result, it has been found that, irrespective of the presence or absence of a hydrofluorocarbon, both of the compounds (A) of formulae (C-1) and (C-2) exhibit markedly excellent extreme pressure property (load at failure), abrasion resistance and coefficient of abrasion.

For example, most of the fluorine-containing aromatic compounds (A) of formulae (C-1) and (C-2) exhibit much more excellent lubricating properties than conventional lubricant oils for use in refrigeration equipment, such as a mineral oil and alkylbenzene, and candidate lubricant oils for refrigeration equipment oil for HFC-134a, such as polyalkylene glycols and polyol ester oils.

Further, it has unexpectedly been found that as shown in Example 73, the lubricant oil composition comprised of the fluorine-containing aromatic compound (A) of formula (C-1) and the alkyl- or alkyl derivative-substituted aromatic compound (B) has excellent anti-wear properties, as compared to the alkyl- or alkyl derivative-substituted aromatic compound (B) alone as well as the fluorine-containing aromatic compound (A) alone.

The above-mentioned lubricating properties can be measured by means of various testers. For example, extreme pressure resistance and anti-wear properties can be measured by Falex tester.

For further improving the anti-wear properties and extreme pressure resistance properties of the lubricant oil composition of the present invention, comprising a fluorine-containing aromatic compound (A) and an alkyl or alkyl derivative-substituted aromatic compound (B), load carrying additives, such as oiliness agents, anti-wear agents and extreme pressure agents, can be added to the lubricant oil composition. From the above viewpoint, fluorine-containing compounds (A) of formulae (C-1) and (C-2) are especially preferred because they exhibit excellent miscibility with various types of conventional additives.

With respect to the usefulness of the above-mentioned additives, reference can be made to, for example, "Additives for Petroleum Products" (published by Saiwai Syobou, Japan, 1979), in which oiliness agents are defined as additives capable of lowering a coefficient of abrasion by adsorption thereof onto a metal surface; anti-wear agents are defined as additives capable of effectively preventing wear under relatively low load; and extreme pressure agents are defined as additives capable of preventing seizing and wear by a reaction thereof with a metal surface under high temperature and high pressure conditions. In the above reference, it is also described that some additives not only serve as a monofunctional agent functioning only as oiliness agent, anti-wear agent, or extreme pressure agent, but also as a multifunctional agent for common purpose of the above-mentioned agents. For example, there can be mentioned an additive which can function not only as an oiliness agent, but also as an anti-wear agent and an extreme pressure agent.

Examples of oiliness agents include carboxylic acids, alcohols, phenols, esters, amides and carboxylic salts.

Examples of carboxylic acids include higher fatty acids, hydroxyaryl fatty acids, caboxylic acid-containing polyhydric alcohol esters and aromatic carboxylic acids. Specific examples of the above-mentioned carboxylic acids include linear saturated fatty acids, such as caproic acid, caprylic acid, capric acid, undecylic acid, lauric acid, myristic acid, palmitic acid, pelargonic acid, stearic acid, arachic acid, cerotic acid and lacceric acid; branched saturated fatty acids, such as isotridecanoic acid, isomyristic acid, isostearic acid and isoarachic acid; and unsaturated fatty acids, such as oleic acid and linoleic acid.

Examples of alcohols include higher alcohols and unesterified hydroxyl group-containing polyhydric alcohol esters. Specific examples of the above-mentioned such higher alcohols and such polyhydric esters include lauryl alcohol, cetyl alcohol, stearyl alcohol, oleyl alcohol, glycerol monooleic ester, glycerol monostearate and glycerol dilaurate.

Examples phenols include alkylphenols and polyhydric phenols. Specific examples of the above-mentioned phenols include 3-pentadecylphenol, 4-heptylphenol, octylphenol, nonylphenol, dodecylphenol and an alkylcatechol.

Examples of esters include higher fatty esters (such as methyl laurate and methyl oleate), polyhydric alcohol esters, and acrylates.

Examples of amides include higher fatty amides (such as lauric amide and oleic amide).

Examples of carboxylates include salts of alkaline metals (e.g., sodium, potassium and the like), salts of alkaline earth metals, (e.g., magnesium, calcium and the like), and carboxylates of other metals, such as aluminum.

Examples of other types of the load carrying additives include sulfur compounds, nitrogen compounds, halogenated compounds, phosphorus compounds, silicone compounds, and metal-containing compounds.

Examples of sulfur compounds include thiophene and derivatives thereof, such as benzothiophene; monosulfides, such as di-n-dodecyl sulfide and dibenzil sulfide; disulfides, such as diphenyl disulfide; polysulfides; sulfones; thiosulfinates; sulfurized oils and fats; thiocarbonates; thiazoles; methanesulfonates; thioacetic acids, such as n-dodecylthioacetic acid; and alkylmercaptans, such as n-octadecylmercaptan.

Examples of nitrogen compounds include benzotriazole derivatives, such as an alkyl-substituted benzotriazole.

Examples of halogenated compounds include paraffin chrolide; chlorinated hydrocarbons, such as a chlorofluorocarbon fluorocarbon (e.g., chlorotrifluoroethylene oligomer); chlorinated compounds, such as chlorinated carboxylic acid derivatives; polar group-containing fluorine compounds, such as fluorinated aliphatic alcohols, fluorinated aliphatic carboxylic acids, fluorinated aliphatic carboxylic esters, perfluoropolyethercaboxylic acids, perfluoropolyethercarboxylic esters, perfluoroalkyltriazines and perfluoropolyethertriazine; fluorinated compounds other than the above-mentioned polar group-containing fluorine compounds, such as graphite fluoride and ethylene fluoride oligomers; brominated compounds, such as alkane bromides, alkene bromides and alkyne bromides; and iodinated compounds, such as iodinated hydrocarbons.

Examples of phosphorus compounds include phosphoric esters, such as phosphoric monoesters, phosphoric diesters, phosphoric triesters and halogenophosphoric esters; phosphonic esters, such as phosphonic monoesters, phosphonic diesters, phosphonic triesters and halogenophosphonic esters; tertiary phosphines; tertiary phosphine oxides; tertiary phosphine sulfides; phosphonic esters; phosphonous acid esters; phosphinic esters; phosphinous acid esters; thiophosphoric esters, such as thiophosphoric triesters; thiophosphonic esters; thiophosponous acid esters; thiophosphinic esters; phosphoroamidates; amine salts of acid phosphoric esters; and phosphazenes.

Examples of silicone compounds include organosilicon compounds, such as silicone fluorides and carboxyl group-containing silicones.

Examples of metal-containing compounds include salts of naphthenic acid, such as zinc naphthenates and lead naphthenates; salts of fatty acids, such as fatty acid leads; thiophosphates, such as zinc dithiophosphates and antimony dithiophosphates; salts of thiocarbamic acid, such as zinc dithiocarbamate, antimony dithiocarbamate and lead dithiocarbamates; organomolybdenum compounds, such as molybdenum oxysulfide dithiocarbamate and oxymolybdenum sulfide phosphorothioate; organotin compounds; organogermanium compounds; organotitanium compounds; boric esters; organosilicates, such as diethylsilicate; and metal sulfides, such as iron sulfide; metal chlorides, such as iron chloride; and composites comprised of some of the above metal compounds.

Specific examples of the above-mentioned polar group-containing fluorine compounds include fluorinated aliphatic alcohols, such as 3,3,4,4,5,5,6,6,7,7,8,8,8-tridecafluorooctanol, 1H,1H,7H-dodecafluoro-1-heptanol, 1H,1H,11H-eicosafluoro-1-undecanol and 2,2,3,3,4,4-hexafluoro- 1,5-pentanediol; fluorinated aliphatic carboxylic esters, such as perfluoromethyl octanate and perfluoromethyl nonanoate; perfluoropolyethercarboxylic esters, such as hexafluoropropene oxide oligomer dicarboxylate and perfluoro-2,5-dimethyl-3,6-dioxanonanoate; fluorinated aliphatic carboxylic acids, such as perfluorononanoic acid; and perfluoropolyethercarboxylic acids, such as perfluoro-2,5-dimethyl-3,6-dioxanonanoic acid.

Specific examples of the above-mentioned phosphorus compounds include orthophosphoric acid esters, such as tricresylphosphate, triphenylphosphate, triisopropylphenylphosphate, tris(2-ethylhexyl)phosphate, di(2-ethylhexyl)tridecylphosphate, di(2-ethylhexyl) allylphosphate, trioctylphosphate, trilaurylphosphate, tristearylphosphate, trioleylphosphate, tris[poly(oxyethylene)tridecyl]phosphate, tris[poly(oxyethylene)-2-ethylhexyl]phosphate, tris [poly(oxyethylene)isooctyl]phosphate, tris[poly(oxyethylene)poly(oxypropylene)-n-octyl]phosphate, tris [poly(oxyethylene)carbonyl-1-ethylpentyl]phosphate, tris [poly(oxyethylene)poly(oxypropylene)carbonyl-1-ethylpentyl]phosphate, tris [poly(oxyethylene)propyleneoxycarbonyl- 1-methylvinyl] phosphate, tris[3-poly(oxyethylene)-methyl-2-methylpropionate]phosphate, tris[poly(oxyethylene)-2-hydroxyoctyl]phosphate, tris(p-octylphenoxyethylene)phosphate, tris[poly(oxyethylene)-poly(oxypropylene)-p-methylphenoxy]phosphate, tris[4-poly(oxyethylene)ethylphenylacetate]phosphate, tris [poly(oxyethylene)poly(oxypropylene)-p-butoxyphenyl] phosphate, 2-ethylhexyl[poly(oxyethylene)- 2-ethylhexyl] phosphate and polyoxyalkylene bis(diaryl)phosphate; acid phosphoric esters, such as ditetradecyl acid phosphate, dipentadecyl acid phosphate, dihexadecyl acid phosphate, diheptadecyl acid phosphate, dioctadecyl acid phosphate, di(polyoxyethlenenonylphenylether)phosphate; amine salts of acid phosphoric esters, such as salts of the above-mentioned acid phosphoric esters, formed with amines, including methylamine, ethylamine, propylamine, butylamine, pentylamine, hexylamine, heptylamine, octylamine, dimethylamine, diethylamine, dipropylamine, dibutylamine, dipentylamine, dihexylamine, diheptylamine, dioctylamine, trimethylamine, triethylamine, tripropylamine, tributylamine, tripentylamine, trihexylamine, triheptylamine and trioctylamine; chlorinated phosphoric esters, such as tris-(dichloropropyl)phosphate, tris(chloroethyl)phosphate, polyoxyalkylene.bis[di(chloroalkyl)]phosphate and tris(chlorophenyl)phosphate; brominated phosphoric esters, such as tris(tribromophenyl)phosphate, tris(dibromophenyl)phosphate and tris(2,4-di-tertbutylphenyl)phosphate; fluorinated phosphoric esters, such as tris(polyfluoroalkyl)phosphate and tris(polyfluorophenyl)phosphate; phosphites, such as dibutylphosphite, tributylphosphite, dipentylphosphite, tripentylphosphite, dihexylphosphite, trihexylphosphite, diheptylphosphite, triheptylphosphite, dioctylphosphite, trioctylphosphite, dinonylphosphite, didecylphosphite, diundecylphosphite, triundecylphosphite, didodecylphosphite, tridodecylphosphite, diphenylphosphite, triphenylphosphite, dicresilphosphite, tricresilphosphite, triisodecylphosphite, diphenyloctylphosphite, diphenyldecylphosphite, dilaurylhydrogenphosphite, dioleylhydrogenphosphite, tris(2,4-di-tertbutylphenyl)phosphite, trinonylphenylphosphite, polyoxyalkylene.bis(diaryl)phosphite, 1,1,3-tris(2-methyl-4-ditridecylphosphite-5-tert-butylphenyl)butane, tetraphenyldipropyleneglycoldiphosphite and tetradecyldiethyleneglycoldiphosphite; phosphonic esters, such as O,O-dimethyldodecylphosphonate, O,O-diethyldodecylphosphonate, O,O-di-n-butyldecylphosphonate, O,O-di-2-ethylhexyldodecylphosphonate, O,O-di-2-ethylhexyl- 2-ethylhexylphosphonate, O,O-di-2-ethylhexy-lisooctylphosphonate, O,O-di-2-ethylhexylphenylphosphonate, O,O-dimethylphosphonomethylene-(dimethyl)succinate, O,O-di-2-ethylhexyl-3-phosphnomethylpropionate, O,O-di-2-ethylhexyltris(ethyleneglycol)methylenephosphonate, O,O-di(decylpolyoxyethylene)phosphonate, O,O-di-2-ethylhexylhydroxymethylenephosphonate and O,O-di-2-ethylhexylphosphonomethylenepolyethyleneglycol; and phosphinic esters, such as O-alkyldialkylphosphinate.

Each of the above-mentioned load carrying additives can be used individually or in combination thereof, or in combination with other additives. When the additive is incorporated in the lubricant oil composition of the present invention, which comprises a fluorine-containing aromatic compound (A) and an alkyl- or alkyl derivative-substituted aromatic compound (B), the amount of the additive is preferably in the range of from 0.01 to 25% by weight, more preferably from 0.05 to 5.0% by weight, still more preferably from 0.1 to 2.0% by weight, based on the weight of the lubricant oil composition. When the amount of the additive contained in the lubricant oil composition is smaller than 0.01% by weight, anti-wear properties and extreme pressure properties thereof cannot be satisfactorily improved. On the other hand, when the amount of the additive is greater than 25% by weight, the properties of the lubricant oil composition for use thereof as a lubricant in refrigeration equipment (such as electrical insulation properties) are adversely affected and, therefore, the composition cannot be practically used.

When the lubricant oil composition of the present invention is used as a refrigerant oil, an anti-corrosive can also be added thereto for improving abrasion resistance of a metal surface of a refrigeration system.

Examples of anti-corrosives include carboxylic acids, carboxylates, sulfonates, esters, amines, phosphoric esters, epoxy compounds and nitrogen-containing heterocyclic compounds.

Examples of carboxylic acids include oleic acid and stearic acid.

Examples of carboxylates include salts of fatty acids, such as lanolin fatty acids, which salts are formed with metals, such as Mg, Ca and Ba.

Examples of sulfonates include salts of petroleum sulfonic acids, dinonylnaphthalenesulfonic acids, and alkylbenzenesulfonic acids, which salts are formed with metals, such as Na, Mg, Ca and Ba.

Examples of esters include sorbitan monofatty acid esters (such as sorbitanmonooleate and sorbitanmonolaurate) and pentaerythritol monofatty acid esters.

Examples of amines include aromatic amines (such as N-phenyl-α-naphthylamine), aliphatic amines and rosin amines.

Examples of phosphoric esters include phosphoric monoesters and salts thereof, phosphoric diesters and salts thereof, phosphoric triesters (such as triphenylphosphate) and phosphites (such as triphenylphosphite).

Examples of epoxy compounds include glycidyl ethers (e.g., arylglycidyl ethers, such as phenylglycidyl ether; and alkylglycidyl ethers, such as 2-ethylhexylglycidyl ether); glycidyl esters (e.g., aromatic carboxylic acid glycidyl esters, such as phthalic acid diglycidyl ester), saturated aliphatic carboxylic acid glycidyl esters (such as 2-ethyl hexanoic acid glycidyl ester and decanoic acid glycidyl ester), unsaturated aliphatic carboxylic acid glycidyl esters, epoxidated fatty acid monoester (e.g., epoxystearic acid ester with butyl, hexyl, benzyl, cyclohexyl, methoxyethyl, octyl, phenyl or butylphenyl).

Examples of nitrogen-containing heterocyclic compounds, such as benzotriazole and derivatives thereof (such as alkyl group-substituted benzotriazoles, e.g., 5-methyl-1H-benzotriazole); imidazole and derivatives thereof; benzoimidazole and derivatives thereof, e.g., 2-(alkyldithio)benzoimidazole; and 1,3,4-thiadiazole polysulfide.

As an example of the other compound than the above-mentioned compounds, which can be used as anti-corrosives, there can be mentioned zinc dialkyldithiophosphate.

Each of the above-mentioned anti-corrosives can be used individually or in combination thereof, or in combination with other types of additives. When the anti-corrosive is incorporated in the lubricant oil composition of the present invention, which comprises a fluorine-containing aromatic compound (A) and an alkyl or alkyl derivative-substituted aromatic compound (B), the amount of the anti-corrosive is preferably in the range of from 000001 to 25% by weight, more preferably from 0.001 to 5.0% by weight, still more preferably from 0.1 to 2.0% by weight, based on the weight of the lubricant oil composition. When the amount of the anti-corrosive contained in the lubricant oil composition is smaller than 0.0001% by weight, anti-corrosive properties cannot be satisfactorily improved. On the other hand, when the amount of the anti-corrosive is greater than 25% by weight, the properties of the lubricant oil composition for use thereof as a lubricant in refrigeration equipment (such as electrical insulation properties) are adversely affected and, therefore, the composition cannot be practically used.

The lubricant oil composition of the present invention can also be used in combination with still other types of additives, such as antioxidants, antifoaming agents, detergent-dispersants, viscosity index improvers, pour point improvers, metal deactivating agents and the like.

Examples of antioxidants include phenols (e.g., 2,6-di-tert-butyl-p-cresol) and aromatic amines (e.g., α-naphtylamine).

Examples of antiforming agents include silicon oils (e.g., dimethylsiloxane) and organosilicates.

Examples of detergent-dispersants include sulfonates, phenates and succinimide.

Examples of viscosity index improvers formed of various types of polymers, such as polymethacrylates.

Examples of pour point improvers include diesters, polyalkylene glycols and triglyceride.

Examples of metal deactivating agents include N,N'-disalicylidene-1,2-diaminoethane and acetylacetone.

When at least one additive selected from the group consisting of the above-mentioned additives is added, the lubricant oil composition of the present invention can be more advantageously used for various refrigeration systems, such as refrigerators, freezers, car air conditioners and room air conditioners, in which, from the viewpoint of the environmental protection, substitute refrigerants (e.g., HFC-134a) are used for conventional chlorine-containing refrigerants, such as CFC-12 and HCFC-22.

In still another aspect of the present invention, there is provided a fluorine-containing aromatic compound represented by the formula:

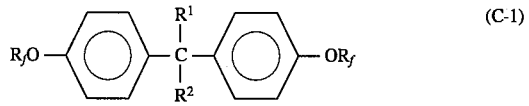
(C-1)

wherein each of $R^1$ and $R^2$ independently represents a hydrogen atom or an alkyl group having from 1 to 19 carbon atoms, wherein the total number of carbon atoms in $R^1$ and $R^2$ is from 4 to 19, preferably from 5 to 16, more preferably from 5 to 12, and each $R_f$ is as defined for formula (A), wherein the $R_f$ groups are the same or different.

In a further aspect of the present invention, there is provided a fluorine-containing aromatic compound represented by the formula:

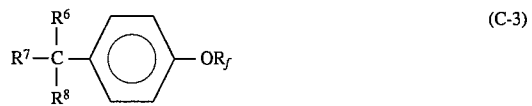
(C-3)

wherein each of $R^6$, $R^7$ and $R^8$ independently represents an alkyl group having from 1 to 20 carbon atoms, the $R_f$ group is as defined for formula (A), wherein the total number of carbon atoms of the $R^6R^7R^8C$— group is from 5 to 25.

With respect to the formula (C-1), when the total number of carbon atoms in $R^1$ and $R^2$ is 3 or less, the bioaccumulation of the compound (C-1) is disadvantageously high. On the other hand, when the total number of carbon atoms in $R^1$ and $R^2$ is 20 or more, the miscibility of the compound (C-1) with a hydrofluorocarbon refrigerant, such as HFC-134a, or a hydrofluoroether refrigerant is low, and also the availability of the material to be used for producing the compound (C-1) is very low. From the viewpoint of increasing stability, it is preferred that each of $R^1$ and $R^2$ in the formula (C-1) be an alkyl group, but not a hydrogen atom.

With respect to the formula (C-3), when the total number of the carbon atoms of the $R^6R^7R^8C$- group of the compound (C-3) is 5 or more, the compound (C-3) exhibits not only an appropriate viscosity and excellent lubricating properties, but also a low bioaccumulation. On the other hand, when the total number of carbon atoms of the $R^6R^7R^8C$- group is 26 or more, the miscibility of the compound (C-3) with a hydrofluorocarbon refrigerant, such as HFC-134a, or a hydrofluoroether refrigerant is low, and also the availability of the material to be used for producing the compound (C-3) is very low.

With respect to $R^1$ and $R^2$ of the formula (C-1) and $R^6$, $R^7$ and $R^8$ of the formula (C-3), each may independently have a substituent group and/or a linkage group. Examples of these substituent and linkage groups include unsaturated hydrocarbon groups; halogen atoms, such as a chlorine atom and a fluorine atom; and various polar groups containing oxygen, nitrogen, phosphorus or sulfur, such as a hydroxyl group, a thiol group, an alkoxy group, a nitrile group, a nitro group, an ether group, a thioether group, an ester group, a carbonyl group, a sulfonyl group, a sulfinyl group, a carboxyl group, a carboxylate group, an amino group, a thiocarbamate group, an amido group, an imido group, a pyridine group, a pyrimidine group, a piperidine group, a triazine group, a phosphine group, a benzoimidazole group, a phosphorous ester group, a triazole group, a tetrazole group, a thiazole group, and a thiadiazole group. Of them, a fluorine atom and an ether group are preferred from the viewpoint of improving stability. The number of such substituent group and/or linkage group in each of $R^1$, $R^2$, $R^6$, $R^7$ and $R^8$ is preferably 5 or less, more preferably 3 or less, still more preferably 1 or less.

Specific examples of compounds (C-1) and (C-3) are as shown above.

The compounds (C-1) and (C-3) can be advantageously used, individually or in mixture thereof, as a lubricant oil in the refrigeration system employing HFC refrigerants or HFE refrigerants. Further, the compound (C-1) and/or the compound (C-3) can also be used in combination with other compounds (A).

Each of the compounds (C-1) and (C-3) has a hybrid structure formed of at least one fluorocarbon group and at least one hydrocarbon group and, hence, it exhibits excellent miscibility with a variety of oils, e.g., hydrocarbons [which hydrocarbons include the compound (B)]. Accordingly, each of the compounds (C-1) and (C-3) can be advantageously used as an additive in a refrigerant system using in combination an HFC refrigerant and a hydrocarbon lubricant, such as an ester oils, a polyalkylene glicol oil, an alkylbenzene or mineral oil (which is well-known to be unsatisfactory in miscibility with the HFC refrigerant), so that the oil return properties can be remarkably improved.

The lubricant oils, which can be used with the compounds (C-1) and (C-3) are, for example, hydrocarbons, such as naphthene mineral oil, paraffin mineral oil, alkylbenzene, alkylnaphthalene and poly-α-olefin; ether compounds, such as polyalkylene glycol and polyphenyl ether; fluorine-containing compounds, such as perfluoropolyether, perfluoropolyether substituted with polar substituents (e.g., a carbonyl-containing group, such as a carboxyl group, a carboxylate group, an amide group, a ketone group and an ester group; a hydroxyl group, an amino group, an imide group, an ether group, a benzoimidazol group, a phosphite group, a phosphine group, a nitril group, a phosphotriazine group and a triazine group), polychlorotrifluoroethylene and chlorofluorocarbon; ester compounds, such as polyol ester, and mixed ester; carbonates, such as polycarbonate; silicon-containing compounds, such as silicate, silicone, and fluorosilicone; phosphorus-containing oils, such as aryl phosphate, alkylaryl phosphate, and alkyl phosphate.

From the above-mentioned conventional oils, one or more appropriate oils can be selected and added, taking into consideration the viscosity and the lubricating properties of the resultant lubricant oil composition containing such oils.

When the compounds (C-1) and/or (C-3) is added to a polar oil, such as ester oil, polyalkylene glycol oil and carbonate oil, the polar oil can be improved with respect or properties, such as low moisture absorption properties, stability, and lubricating properties.

For further improving the abrasion resistance properties and extreme pressure resistance properties of the lubricant oil of the present invention, comprising a fluorine-containing aromatic compound (C-1) and/or (C-3), it is preferred that the same type of additives as mentioned above for the lubricant oil composition of the present invention be also added. The same amounts of the additives (% by weight, based on the total amount of the lubricant oil) as mentioned above for the lubricant oil composition of the present invention can be employed for the lubricant oil (C-1) and/or (C-3) of the present invention.

It has been found that the compounds (C-1) and (C-3) exhibit excellent miscibility not only with a hydrofluorocarbon refrigerant, but also with a hydrofluoroether refrigerant which is attracting attention because a hydrofluoroether has a global warming potential advantageously lower than that of a hydrofluoroarbon.

Further, the fluorine-containing aromatic compounds (C-1) and (C-3) exhibit various advantageous properties, such as excellent miscibility with various types of oils, low bioaccumulation, high stability and excellent lubricating properties. Therefore, the compounds (C-1) and (C-3), even if not mixed with compound (B), can be used, individually or in mixture thereof or in a mixed form with other oils, as a lubricant oil which is excellent not only as a lubricant oil for a refrigerant system, but also, for example, as a lubricant oil for a magnetic recording medium, a compressor oil, an operating oil, a rolling oil, a gear oil, a traction drive oil, an engine oil and a base oil for grease. Furthermore, the above-mentioned compounds (C-1) and (C-3) can also be used, for example, as an agent for improving the durability or lubricating properties of various types of oils, an agent for improving the surface characteristics of a polymer, a mold release agent, an agent for improving miscibility, and a base oil for an electroviscous fluid or a magnetic fluid. However, uses of the compounds (C-1) and (C-3) of the present invention are not limited to the above-mentioned examples.

When at least one additive selected from the group consisting of the above-mentioned additives is added, the lubricant oil (C-1) and/or (C-3) of the present invention can be more advantageously used for various refrigeration systems, such as refrigerators, freezers, car air conditioners and room air conditioners, in which, from the viewpoint of the environmental protection, substitute refrigerants (e.g., HFC-134a) are used for conventional chlorine-containing refrigerants, such as CFC-12 and HCFC-22.

BEST MODE FOR CARRYING OUT THE INVENTION

The present invention will now be described in greater detail with reference to the following Referential Examples, Examples and Comparative Examples, which should not be construed as limiting the scope of the present invention.

The kinetic viscosity of a lubricant oil can be determined by measuring the viscosity by means of various viscometers. As the viscometer to be used for determining the kinetic viscosity, there can be mentioned a capillary viscometer, such as a Ubbellohde viscometer, an Ostward viscometer or a Cannon-Fenske viscometer, a rotational viscometer, and a falling ball viscometer. In the present invention, an E-type rotational viscometer (manufactured and sold by Tokyo Keiki, Japan) is used.

Referential Example 1

In accordance with the method described in Example 54 of Unexamined Japanese Patent Application Laid-Open Specification No. 5-86382, oil [S1] is synthesized as follows.

68.7 g of 2,2-bis(4-hydroxyphenyl)propane (hereinafter referred to simply as "bisphenol A"), 6.2 g of potassium hydroxide, 120 ml of dimethylsulfoxide and 1 ml of water are charged into a microcylinder having a capacity of 500 ml as a reactor, thereby obtaining a mixture. The reactor is heated to 60° C. by means of an oil bath, and the mixture is stirred at 60° C. under atmospheric pressure for 5 hours, to thereby obtain a solution. The inside of the reactor is degassed and then, inert gas $N_2$ is charged to restore atmospheric pressure. The reactor is heated to 60° C. by means of the oil bath, followed by introduction of tetrafluoroethylene, thereby starting a reaction. While feeding tetrafluoroethylene so as to maintain the pressure in the reactor (gauge pressure) at 3 to 4 kg/cm$^2$, the reaction is carried out for about 5 hours to thereby obtain a reaction mixture.

After the reaction, the dimethylsulfoxide is distilled off from the reaction mixture at 150° C. under about 5 mmHG to obtain a reaction product. The obtained reaction product is washed with about 100 ml of purified water 5 times. Thus, 130 g of a colorless, transparent oil (containing 99% by weight of the oil [S1]) is obtained.

Simple distillation (the boiling point is about 150° C. under about 0.1 to 0.3 mmHg) and subsequently, separation treatment using a silica gel column are conducted to thereby isolate the oil [S1].

The thus isolated oil [S1] is analyzed by infra-red absorption spectrometry and mass spectrometry [m/e 428 (M$^+$), 413 (M$^+$–CH$_3$)] to thereby confirm that the oil [S1] is a compound having the following structural formula:

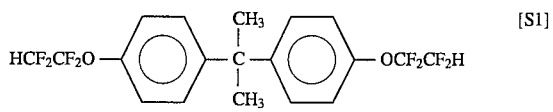

The kinetic viscosity of the oil [S1] at 40° C. is 26 cSt.

Referential Example 2

Substantially the same procedure as in Referential Example 1 is repeated except that chlorotrifluoroethylene is used in place of tetrafluoroethylene, and that the amount of water to be added is changed from 1 ml to 44 ml, to thereby obtain a colorless, transparent oil [S2] (yield: 99%).

The thus obtained oil [S2] is analyzed by gas chromatography. As a result, it is found that the obtained oil [S2] has a purity of 99.9% with respect to a desired product. The obtained oil [S2] is also analyzed by infrared absorption spectrometry and mass spectrometry [m/e 460, 462 ($M^+$), 445, 447 ($M^+$–$CH_3$)] to thereby confirm that the oil [S2] is a compound having the following structural formula:

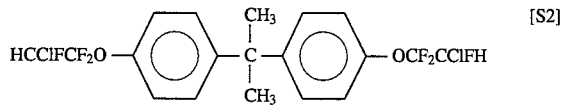

The kinetic viscosity of the oil [S2] at 40° C. is 57 cSt.

Referential Example 3

Oil [S3] is obtained in substantially the same manner as in Referential Example 1 except that compound [G1] shown below is used in place of bisphenol A (yield: 95%).

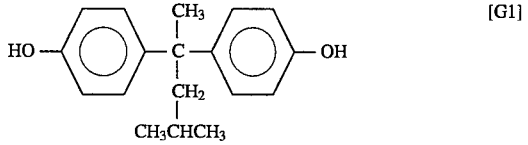

From the results of infrared absorption spectrometry shown in FIG. 1 and mass spectrometry [m/e 470 ($M^+$)], it is confirmed that the oil [S3] is a compound having the following structural formula:

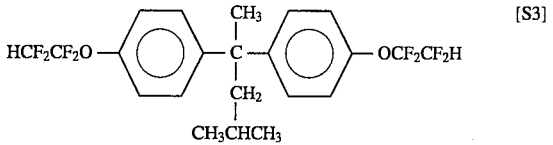

The kinetic viscosity of the oil [S3] at 40° C. is 109 cSt.

Referential Example 4

Figure 2:
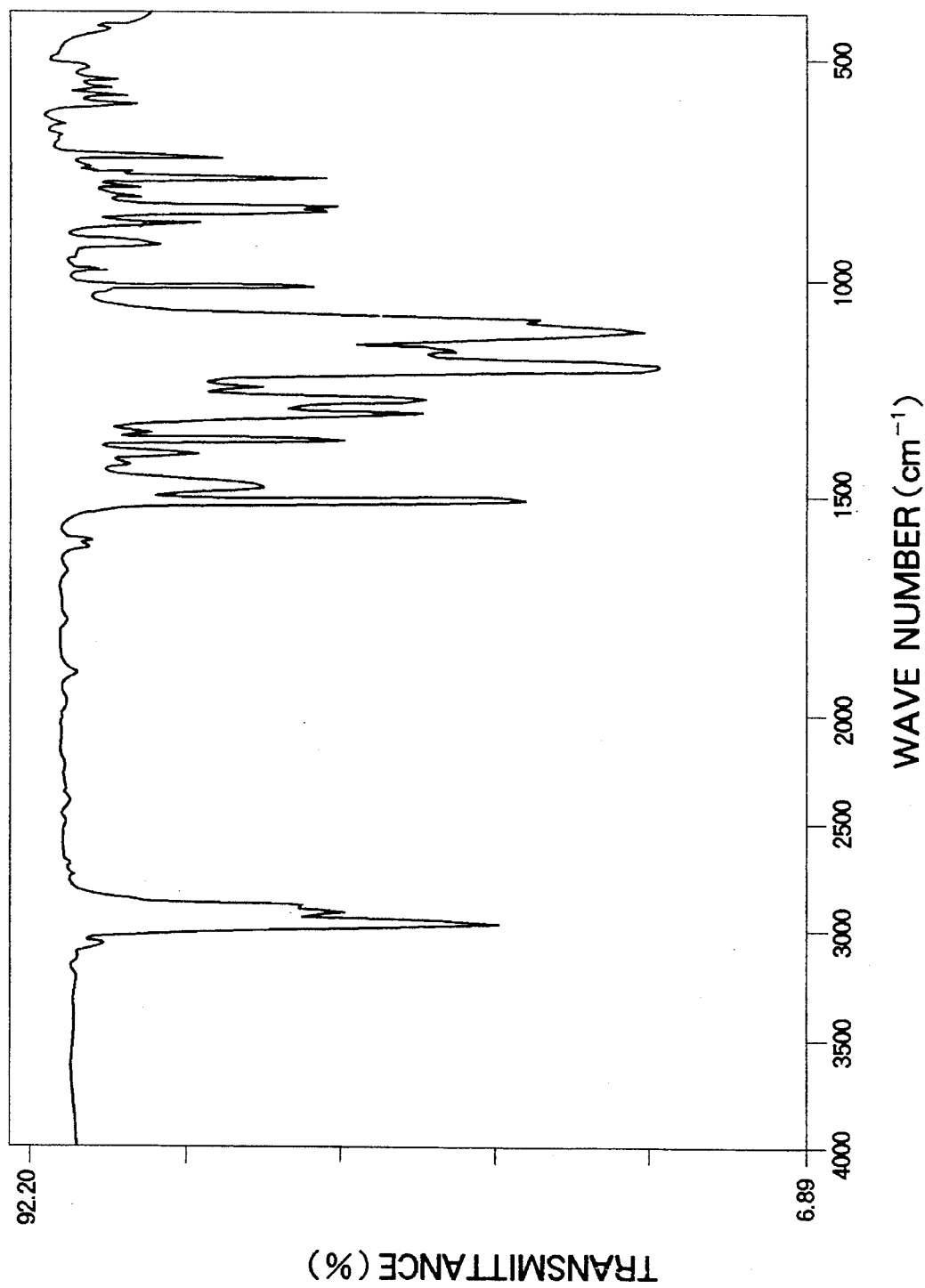
FIG. 2 is a chart showing the infrared spectrum of fluorine-containing compound [S4] [compound (A) prepared in Referential Example 4].

Oil [S4] is obtained in substantially the same manner as in Referential Example 1 except that p-t-octylphenol (manufactured and sold by Tokyo Kasei Kogyo Co., Ltd., Japan) is used in place of bisphenol A (yield: 94%). From the results of infrared absorption spectrometry shown in FIG. 2 and mass spectrometry [m/e 306 ($M^+$)], it is confirmed that the oil [S4] is a compound having the following structural formula:

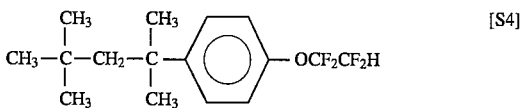

The kinetic viscosity of the oil [S4] at 40° C. is 6.1 cSt.

Referential Example 5

Oil [S5] is obtained in substantially the same manner as in Referential Example 1 except that compound [G2] shown below is used in place of bisphenol A (yield: 90%).

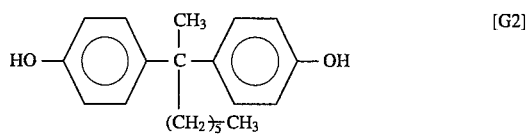

From the results of infrared absorption spectrometry and mass spectrometry [m/e 498 ($M^+$)], it is confirmed that the oil [S5] is a compound having the following structural formula:

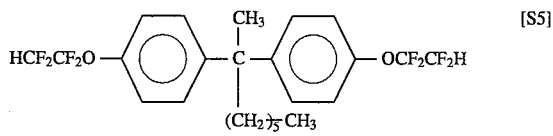

The kinetic viscosity of the oil [S5] at 40° C. is 112 cSt.

Referential Example 6

Oil [S6] is obtained in substantially the same manner as in Referential Example 1 except that compound [G3] shown below is used in place of bisphenol A (yield: 88%).

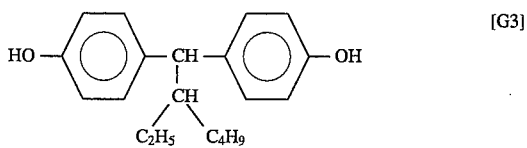

From the results of infrared absorption spectrometry and mass spectrometry [m/e 498 ($M^+$)], it is confirmed that the oil [S6] is a compound having the following structural formula:

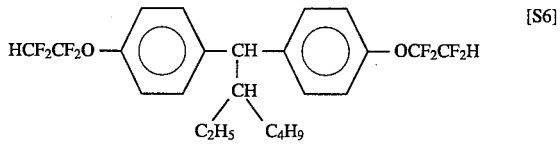

The kinetic viscosity of the oil [S6] at 40° C. is 250 cSt.

Referential Example 7

Oil [S7] is obtained in substantially the same manner as in Referential Example 1 except that compound [G1] shown in Referential Example 3 is used in place of bisphenol A, that chlorotrifluoroethylene is used in place of tetrafluoroethylene, and that the amount of water to be added is changed from 1 ml to 44 ml (yield: 95%). From the results of infrared absorption spectrometry and mass spectrometry [m/e 502, 504 ($M^+$)], it is confirmed that the oil [S7] is a compound having the following structural formula:

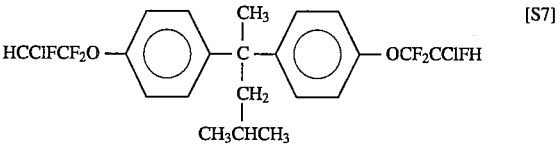

The kinetic viscosity of the oil [S7] at 40° C. is 230 cSt.

Referential Example 8

Oil [S8] is obtained in substantially the same manner as in Referential Example 1 except that 2,4-di-t-amylphenol is used in place of bisphenol A (yield: 90%). From the results of infrared absorption spectrometry and mass spectrometry [m/e 334 ($M^+$)], it is confirmed that the oil [S8] is a compound having the following structural formula:

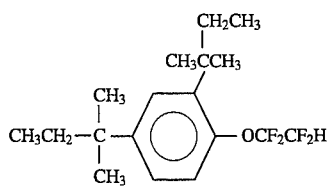 [S8]

The kinetic viscosity of the oil [S8] at 40° C. is 9.0 cSt.

Referential Example 9

Oil [S9] is obtained in substantially the same manner as in Referential Example 1 except that compound [G4] shown below is used in place of bisphenol A (yield: 94%).

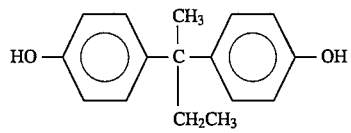 [G4]

From the results of infrared absorption spectrometry and mass spectrometry [m/e 442 ($M^+$)], it is confirmed that the oil [S9] is a compound having the following structural formula:

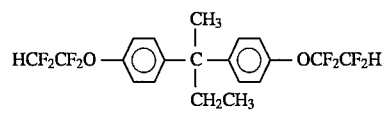 [S9]

The kinetic viscosity of the oil [S9] at 40° C. is 50 cSt.

Referential Example 10

Oil [S10] is obtained in substantially the same manner as in Referential Example 1 except that compound [G5] shown below is used in place of bisphenol A (yield: 91%].

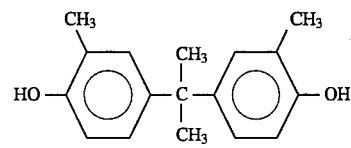 [G5]

From the results of infrared absorption spectrometry and mass spectrometry [m/e 456 ($M^+$)], it is confirmed that the oil [S10] is a compound having the following structural formula:

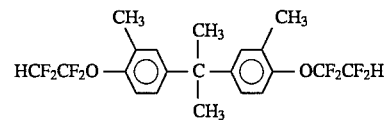 [S10]

The kinetic viscosity of the oil [S10] at 40° C. is 115 cSt.

Referential Example 11

Compound [S11] is obtained in substantially the same manner as in Referential Example 1 except that compound [G6] shown below is used in place of bisphenol A (yield: 96%).

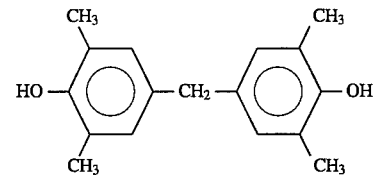 [G6]

The compound [S11] is solid at room temperature. From the results of infrared absorption spectrometry and mass spectrometry [m/e 456 ($M^+$)], it is confirmed that the compound [S11] is a compound having the following structural formula:

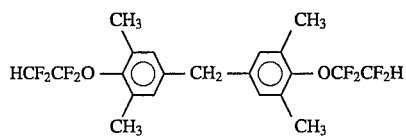 [S11]

Referential Example 12

Oil [S12] is obtained in substantially the same manner as in Referential Example 1 except that p-n-heptylphenol is used in place of bisphenol A (yield: 95%). From the results of infrared absorption spectrometry and mass spectrometry [m/e 292 ($M^+$)], it is confirmed that the oil [S12] is a compound having the following structural formula:

 [S12]

The kinetic viscosity of the oil [S12] at 40° C. is 3.1 cSt.

Referential Example 13

Oil [S13] is obtained in substantially the same manner as in Referential Example 1 except that nonylphenol is used in place of bisphenol A (yield: 92%). From the results of infrared absorption spectrometry and mass spectrometry [m/e 320 ($M^+$)], it is confirmed that the oil [S13] is a compound having the following structural formula:

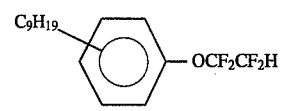 [S13]

The kinetic viscosity of the oil [S13] at 40° C. is 6.2 cSt.

Referential Example 14

Oil [S14] is obtained in substantially the same manner as in Referential Example 1 except that dodecylphenol is used in place of bisphenol A (yield: 93%). From the results of infrared absorption spectrometry and mass spectrometry [m/e 362 ($M^+$)], it is confirmed that the oil [S14] is a compound having the following structural formula:

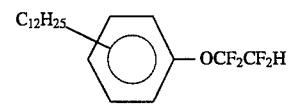 [S14]

The kinetic viscosity of the oil [S14] at 40° C. is 14 cSt.

Referential Example 15

Oil [S15] is obtained in substantially the same manner as in Referential Example 1 except that compound [G1] shown in Referential Example 3 is used in place of bisphenol A, that perfluoropropylvinyl ether ($CF_2=CFOCF_2CF_2CF_3$) is used in place of tetrafluoroethylene, and that the synthesis is conducted on a scale of 1/20 of that of Referential Example 1.

Oil [S15] is isolated from the crude reaction product by means of Kugel Rohr type micro-distillation apparatus. From the results of infrared absorption spectrometry and mass spectrometry [m/e 802 ($M^+$)], it is confirmed that the oil [S15] is a compound having the following structural formula:

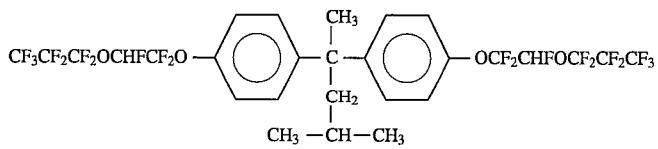

[S15]

Referential Example 16

Oil [S16] is obtained in substantially the same manner as in Referential Example 1 except that compound [G1] shown in Referential Example 3 is used in place of bisphenol A, that hexafluoropropene ($CF_2=CFCF_3$) is used in place of tetrafluoroethylene, and that the synthesis is conducted in a scale of 1/20 that of Referential Example 1.

Oil [S16] is isolated from the crude reaction product by means of Kugel Rohr type micro-distillation apparatus. From the results of infrared absorption spectrometry and mass spectrometry [m/e 530, 550, 570 ($M^+$)], it is confirmed that the oil [S16] is a mixture of substances represented by the following structural formula:

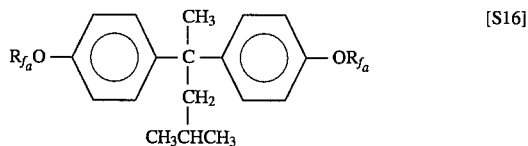

[S16]

wherein $R_{f_a}$ groups each independently represent $CF_3CF=CF-$ or $CF_3CHFCF_2-$.

Referential Example 17

Oil [S17] is obtained in substantially the same manner as in Referential Example 1 except that p-t-octylphenol (manufactured and sold by Tokyo Kasei Kogyo Co., Ltd., Japan) is used in place of bisphenol A, that perfluoropropylvinyl ether ($CF_2=CFOCF_2CF_2CF_3$) is used in place of tetrafluoroethylene, and that the synthesis is conducted on a scale of 1/20 of that of Referential Example 1.

Oil [S17] is isolated from the crude reaction product by means of Kugel Rohr type micro-distillation apparatus. From the results of infrared absorption spectrometry and mass spectrometry [m/e 472 ($M^+$)], it is confirmed that the oil [S17] is a compound having the following structural formula:

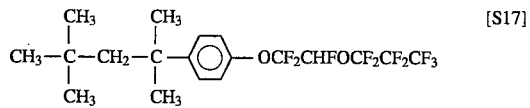

[S17]

Referential Example 18

Oil [S18] is obtained in substantially the same manner as in Referential Example 1 except that p-t-octylphenol (manufactured and sold by Tokyo Kasei Kogyo Co., Ltd., Japan) is used in place of bisphenol A, that hexafluoropropene ($CF_2=CFCF_3$) is used in place of tetrafluoroethylene, and that the synthesis is conducted on a scale of 1/20 of that of Referential Example 1.

Oil [S18] is isolated from the crude reaction product by means of Kugel Rohr type micro-distillation apparatus. From the results of infrared absorption spectrometry and mass spectrometry [m/e 336,356 ($M^+$)], it is confirmed that the oil [S18] is a mixture of substances represented by the following structural formula:

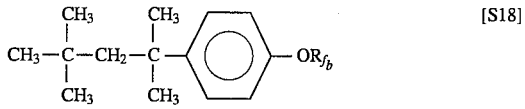

[S18]

wherein $R_{f_b}$ group represents $CF_3CF=CF-$ or $CF_3CHFCF_2-$.

Referential Example 19

Oil [S19] is obtained in substantially the same manner as in Referential Example 1 except that p-t-octylphenol (manufactured and sold by Tokyo Kasei Kogyo Co., Ltd., Japan) is used in place of bisphenol A, that chlorotrifluoroethylene ($CF_2=CFC_1$) is used in place of tetrafluoroethylene, and that the synthesis is conducted on a scale of 1/20 of that of Referential Example 1.

Oil [S19] is isolated from the crude reaction product by means of Kugel Rohr type micro-distillation apparatus. From the results of infrared absorption spectrometry and mass spectrometry [m/e 322,324 ($M^+$)], it is confirmed that the oil [S19] is a compound having the following structural formula:

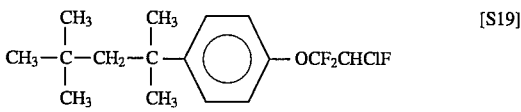

[S19]

In the following Examples and Comparative Examples, various properties of some fluorine-containing aromatic compounds which are conventional but usable as compound (A) in the present invention are also shown under Examples.

EXAMPLE 1

<Miscibility Test between the fluorine-containing aromatic compound (A) and various types of oils including the alkyl- or alkyl derivative-substituted aromatic compound (B)>

The miscibility of the compound [S1] [compound (A)] obtained in Referential Example 1 with Aromix 20T [compound (B)] (tradename of (branched)alkylbenzene having a kinetic viscosity at 40° C. of 14 cSt, manufactured and sold by Nippon Petroleum Detergent Co., Ltd., Japan) is evaluated at 25° C. by the following method. 100 parts by weight of the compound [S1] is placed in a beaker, and Aromix 20T is stepwise added thereto 1 part by 1 part by weight until the total amount of added Aromix 20T becomes 100 parts by weight, while visually evaluating the miscibility of the compound [S1] with the Aromix 20T. Separately, 100 parts by weight of Aromix 20T is placed in a beaker, and the compound [S1] is stepwise added thereto 1 part by 1 part by weight until the total amount of added compound [S1] becomes 100 parts by weight, while visually evaluating the miscibility of the compound [S1] with the Aromix 20T.

As a result, it is found that the compound [S1] is completely miscible with Aromix 20T over the entire weight ratio range. Results are shown in Table 1.

EXAMPLES 2 AND 3

Substantially the same procedure as in Example 1 is repeated except that Aromix 22 .[compound (B)] (tradename of (branched)alkylbenzene having a kinetic viscosity at 40° C. of 31.5 cSt, manufactured and sold by Nippon Petroleum Detergent Co., Ltd., Japan) and AB-SG [compound (B)] (tradename of (linear)alkylbenzene having a kinetic viscosity at 30° C. of 5.8 cSt, manufactured and sold by Mitsubishi Petrochemical Co., Ltd., Japan) are individually used (respectively in Examples 2 and 3) in place of Aromix 20T, thereby evaluating the miscibility at 25° C. of the compound [S1] with each of Aromix 22 and AB-SG. As a result, it is found that the compound [S1] is completely miscible with each of Aromix 22 and AB-SG over the entire weight ratio range. Results are shown in Table 1.

COMPARATIVE EXAMPLES 1 AND 2

Substantially the same procedure as in Example 1 is repeated except that SUNISO 3GS [compound (B)] (tradename of a naphthene mineral oil having a kinetic viscosity at 40° C. of 30 cSt, manufactured and sold by Japan Sun Oil Company, Ltd., Japan) and a liquid paraffin [compound (B)] (having a kinetic viscosity at 40° C. of 40 cSt and which is a first grade reagent manufactured and sold by Wako Pure Chemical Industries, Ltd., Japan) are individually used (respectively in Comparative Examples 1 and 2) in place of Aromix 20T, thereby evaluating the miscibility at 25° C. of the compound [S1] with each of SUNISO 3GS and the liquid paraffin. As a result, it is found that the compound [S1] is miscible with each of SUNISO 3GS and the liquid paraffin only in a limited weight ratio range. Results are also shown in Table 1.

In Tables 1 to 2, "Component I" and "Component II" are inserted in order to identify two components of each of the lubricant oil compositions used in Examples and Comparative Examples. That is, "Component I" is used to identify the fluorine-containing aromatic compound (A) for the lubricant oil composition of the present invention, and other fluoro compound, such as perfluoropolyether, which is similar to compound (A) but not usable in the present invention, while "Component II" is used in order to identify the alkyl- or alkyl derivative-substituted aromatic compound (B) for the lubricant oil composition of the present invention, and a non-aromatic compound, such as ester oil, which is similar to compound (B) but is not usable in the present invention.

TABLE 1

| | Component I: Compound (A) | Component II: Compound (B) or non-aromatic compound | Miscibility of I with II at 25° C. |
| --- | --- | --- | --- |
| Example 1 | [S1] | Aromix 20T*[1] | Miscible over the entire weight ratio range |
| Example 2 | [S1] | Aromix 22*[2] | Miscible over the entire weight ratio range |
| Example 3 | [S1] | AB-SG*[3] | Miscible over the entire weight ratio range |
| Comparative Example 1 | [S1] | SUNISO 3GS*[4] | Not miscible at a weight ratio ([S1]/SUNISO 3GS) in the range from 37/63 to 83/17 |
| Comparative Example 2 | [S1] | Liquid paraffin*[5] | Not miscible at a weight ratio ([S1]/liquid paraffin) in the range from 13/87 to 95/5 |

Note
*[1](Branched)alkylbenzene, manufactured by Nippon Petroleum Detergent Co., LTD., Japan (kinetic viscosity at 40° C.: 14 cSt)
*[2](Branched)alkylbenzene, manufactured by Nippon Petroleum Detergent Co., LTD., Japan (kinetic viscosity at 40° C.: 31.5 cSt)
*[3](Linear)alkylbenzene, manufactured by Mitsubishi Petrochemical Co., Japan (kinetic viscosity at 30° C.: 5.8 cSt)
*[4]Naphthene mineral oil, manufactured by Japan Sun Oil Company, Ltd., Japan (kinetic viscosity at 40° C.: 30 cSt)
*[5]First grade reagent, manufactured by Wako Pure Chemical Industries, Ltd., Japan (kinetic viscocity at 40° C.: 40 cSt)

As is apparent from Examples 1 to 3 and Comparative Examples 1 and 2, the compound [S1], which falls within the class of the fluorine-containing aromatic compound (A) is completely miscible with an aromatic hydrocarbon over the entire weight ratio range, and the compound [S1] is miscible with a non-aromatic compound only in a limited weight ratio range.

EXAMPLE 4

<Miscibility Test between the lubricant oil composition and HFC-134a>

The compound IS1] obtained in Referential Example 1 is mixed with Aromix 20T in a weight ratio ([S1]/Aromix 20T) of 80/20, to thereby obtain a lubricant oil composition. The miscibility of the obtained lubricant oil composition with 1,1,1,2-tetrafluoroethane (HFC-134a) as a refrigerant is evaluated by the following method.

First, 1.8 g of the lubricant oil composition is charged in a glass tube having an internal volume of 6 ml and then, the whole is cooled by liquid nitrogen. The interior of the glass tube is evacuated and then, about 0.2 g of HFC-134a is introduced into the glass tube. The glass tube is sealed, and the miscibility of the lubricant oil composition with HFC-134a at room temperature is visually evaluated. Then, a lower limit temperature of the lubricant oil composition for being miscible with HFC-134a is measured as follows. The glass tube is cooled with a cooling medium composed of methanol and, after the temperature is equilibrated, the miscibility is visually evaluated. The temperature at which a clear, homogeneous liquid mixture of the lubricant oil composition and HFC-134a begins to become a turbid suspension, is taken as the lower limit temperature. Results of the test are shown in Table 2.

EXAMPLES 5 AND 6

A lubricant oil composition is prepared in substantially the same manner as in Example 4 except that Alken L [compound (B)] (tradename of (linear)alkylbenzene having a kinetic viscosity at 40° C. of 4.3 cSt, manufactured and sold by Nippon Petroleum Detergent Co., Ltd., Japan) and AB-SG [compound (B)] (tradename of (linear)alkylbenzene having a kinetic viscosity at 40° C. of 5.8 cSt, manufactured

COMPARATIVE EXAMPLES 3 TO 5

Substantially the same procedure as in Example 4 is repeated except that each of the compound [S1] and the compound [S2] is individually mixed with each of various non-aromatic compounds indicated in Table 2, thereby evaluating the miscibility of the lubricant oil composition with HFC-134a. Results are shown in Table 2.

TABLE 2

|  | Component I: Compound (A) | Component II: Compound (B) or non-aromatic compound | Weight ratio of I/II | Lower limit temperature for lubricant oil composition to be miscible with HFC-134a (see Note*[1]) |
|---|---|---|---|---|
| Example 4 | [S1] | Aromix 20T | 80/20 | −50° C. |
| Example 5 | [S1] | Alken L*[2] | 80/20 | −55° C. |
| Example 6 | [S1] | AB-SG | 80/20 | −55° C. |
| Example 7 | [S2] | Aromix 20T | 80/20 | −40° C. |
| Example 8 | [S1] | Aromix 20T | 20/80 | −14° C. |
| Comparative Example 3 | [S1] | SUNISO 3GS | 80/20 | Homogeneous liquid mixture of [S1] and SUNISO 3GS can not be obtained at room temperature |
| Comparative Example 4 | [S1] | Liquid paraffin*[3] | 80/20 | Homogeneous liquid mixture of [S1] and liquid paraffin can not be obtained at room temperature |
| Comparative Example 5 | [S2] | SUNISO 3GS | 50/50 | Not miscible at room temperature |

Note
*[1]Weight ratio of lubricant oil composition/HFC-134a: 90/10
*[2](Linear)alkylbenzene, manufactured by Nipon Petroleum Detergent Co., Ltd., Japan (kinetic viscosity at 40° C.: 4.3 cSt)
*[3]First grade reagent, manufactured by Wako Pure Chemical Industries, Ltd., Japan (kinetic viscosity at 40° C.: 40 cSt)

and sold by Mitsubishi Petrochemical Co., Ltd., Japan) are individually used (in Examples 5 and 6) in place of Aromix 20T. Then, in substantially the same manner as in Example 4, the miscibility of the lubricant oil composition with HFC-134a is evaluated. Results are shown in Table 2.

EXAMPLE 7

Substantially the same procedure as in Example 4 is repeated except that the compound [S2] [compound (A)] obtained in Referential Example 2 is used in place of the compound [S1], thereby evaluating the miscibility of the lubricant oil composition with HFC-134a. Results are shown in Table 2.

EXAMPLE 8

Substantially the same procedure as in Example 4 is repeated except that the compound [S1] is mixed with Aromix 20T in a weight ratio ([S1]/Aromix 20T) of 20/80, thereby evaluating the miscibility of the lubricant oil composition with HFC-134a. Results are shown in Table 2.

As is apparent from Examples 4 to 8 and Comparative Examples 3 to 5, a lubricant oil composition comprising a fluorine-containing aromatic compound (A) and an alkyl- or alkyl derivative-substituted aromatic compound (B) exhibits a good miscibility with HFC-134a even at low temperatures, as compared to the lubricant oil composition comprising the fluorine-containing aromatic compound (A) and a non-aromatic compound.

EXAMPLES 9 TO 13

Substantially the same procedure as in Example 1 is repeated except that the compound [S3] [compound (A)] obtained in Referential Example 3 is mixed with individual alkyl- or alkyl derivative-substituted aromatic compounds (B) indicated in Table 3, thereby evaluating the miscibility at 25° C. of the compound [S3] with individual alkyl- or alkyl derivative-substituted aromatic compounds. Results are shown in Table 3.

COMPARATIVE EXAMPLE 6

Substantially the same procedure as in Example 1 is repeated except that the compound [S3] is used in place of the compound [S1] and a liquid paraffin (having a kinetic viscosity at 40° C. of 40 cSt and which is a first grade reagent manufactured and sold by Wako Pure Chemical Industries, Ltd., Japan) is used in place of Aromix 20T, thereby evaluating the miscibility at 25° C. of the compound [S3] with the liquid paraffin. Results are shown in Table 3.

SUNISO 3GS) of 80/20. Then, in substantially the same manner as in Example 4, the miscibility of the lubricant oil composition with HFC-134a is evaluated. Results are shown in Table 4.

TABLE 3

|  | Component I: Compound (A) | Component II: Compound (B) or non-aromatic compound | Miscibility of Component I with Component II at 25° C. |
|---|---|---|---|
| Example 9 | [S3] | Aromix 68*[1] | Miscible over the entire weight ratio range |
| Example 10 | [S3] | Aromix 22*[2] | Miscible over the entire weight ratio range |
| Example 11 | [S3] | Aromix 20T | Miscible over the entire weight ratio range |
| Example 12 | [S3] | Alken L | Miscible over the entire weight ratio range |
| Example 13 | [S3] | AB-SG | Miscible over the entire weight ratio range |
| Comparative Example 6 | [S3] | Liquid paraffin*[3] | Not miscible at a weight ratio ([S3]/liquid paraffin) in the range from 24/76 to 88/12 |

Note
*[1](Branched)alkylbenzene manufactured by Nippon Petroleum Detergent Co., Ltd., Japan (kinetic viscosity at 40° C.: 78.0 cSt)
*[2](Branched)alkylbenzene manufactured by Nippon Petroleum Detergent Co., Ltd., Japan (kinetic viscosity at 40° C.: 31.5 cSt)
*[3]First grade reagent, manufactured by Wako Pure Chemical Industries, Ltd., Japan (kinetic viscosity at 40° C.: 40 cSt)

As is apparent from Examples 9 to 13 and Comparative Example 6, the compound [S3], which falls within the class of the fluorine-containing aromatic compound (A), particularly represented by formula (C-1), is completely miscible with the alkyl- or alkyl derivative-substituted aromatic compound (B) over the entire weight ratio range, although the compound [S3] is miscible with a non-aromatic compound only in a limited weight ratio range.

EXAMPLES 14 TO 16

Lubricant oil compositions are individually prepared in accordance with the formulations indicated in Table 4, using the compound [S3] and each of various alkyl- or alkyl derivative-substituted aromatic compounds [compound (B)] indicated in Table 4. Then, in substantially the same manner as in Example 4, the miscibility of each of the lubricant oil compositions with HFC-134a is evaluated. Results are shown in Table 4.

COMPARATIVE EXAMPLE 7

A lubricant oil composition is prepared by mixing the compound [S3] and SUNISO 3GS in a weight ratio ([S3]/

TABLE 4

|  | Component I: Compound (A) | Component II: Compound (B) or non-aromatic compound | Weight ratio of I/II | Lower limit temperature for lubricant oil composition to be miscible with HFC-134a (see Note *) |
|---|---|---|---|---|
| Example 14 | [S3] | Aromix 68 | 80/20 | −30° C. |
| Example 15 | [S3] | AB-SG | 80/20 | −65° C. |
| Example 16 | [S3] | Aromix 20T | 20/80 | −40° C. |
| Comparative Example 7 | [S3] | SUNISO 3GS | 80/20 | 5° C. |

Note
*Weight ratio of lubricant oil composition/HFC-134a: 90/10

As is apparent from Examples 14 to 16 and Comparative Example 7, the lubricant oil composition comprising the fluorine-containing aromatic compound (A), particularly represented by formula (C-1), and the alkyl- or alkyl derivative-substituted aromatic compound (B) exhibits a good miscibility with HFC-134a even at low temperatures, as compared to the lubricant oil composition comprising the fluorine-containing aromatic compound (A), particularly represented by formula (C-1), and the non-aromatic compound. Further, when Examples 6 and 8 (in which the compound [S1] is employed) are compared with Examples 15 and 16 (in which the compound [S3] is employed), it is found that the lubricant oil composition containing the compound [S3] as the fluorine-containing aromatic compound (A) exhibits a lower limit temperature for miscibility which is far lower than that of a lubricant oil composition containing the compound [S1] as the fluorine-containing aromatic compound (A), despite the fact that the former is more viscous than the latter.

EXAMPLES 17 TO 20

Lubricant oil compositions are individually prepared in accordance with the formulation indicated in Table 5, using the compound [S4] [compound (A)] obtained in Referential Example 4 and each of various alkyl- or alkyl derivative-substituted aromatic compounds (B) indicated in Table 5. Then, in substantially the same manner as in Example 4, the miscibility of each of the lubricant oil compositions with HFC-134a is evaluated. Results are shown in Table 5.

COMPARATIVE EXAMPLE 8

A lubricant oil composition is prepared by mixing the compound [S4] and SUNISO 3GS in a weight ratio ([S4]/SUNISO 3GS) of 20/80. Then, in substantially the same manner as in Example 4, the miscibility of the lubricant oil composition with HFC-134a is evaluated. Results are shown in Table 5.

conducted in substantially the same manner as in Example 4, except that a mixed refrigerant of HFC-32/HFC-125/HFC-134a (weight ratio: 30/10/60) is used as the refrigerant in place of HFC-134a, to thereby evaluate the miscibility of each of the lubricant oil compositions with the mixed refrigerant of HFC-32/HFC-125/HFC-134a. Results are shown in Table 6.

TABLE 5

| | Component I: Compound (A) | Component II: Compound (B) or non-aromatic compound | Weight ratio of I/II | Lower limit temperature for lubricant oil composition to be miscible with HFC-134a (see Note *) |
|---|---|---|---|---|
| Example 17 | [S4] | Aromix 20T | 80/20 | −75° C. |
| Example 18 | [S4] | AB-SG | 80/20 | −75° C. |
| Example 19 | [S4] | Aromix 20T | 20/80 | −42° C. |
| Example 20 | [S4] | Alken L | 20/80 | −42° C. |
| Comparative Example 8 | [S4] | SUNISO 3GS | 20/80 | −5° C. |

Note
*Weight ratio of lubricant oil composition/HFC-134a: 90/10

As is apparent from Examples 17 to 20 and Comparative Example 8, the lubricant oil composition comprising the compound [S4] (which falls within the class of the fluorine-containing aromatic compound (A), particularly represented by formula (C-2)), and the alkyl- or alkyl derivative-substituted aromatic compound (B) exhibits a good miscibility with HFC-134a even at low temperatures, as compared to the lubricant oil composition comprising the fluorine-containing aromatic compound (A), particularly represented by formula (C-2), and the non-aromatic hydrocarbon.

EXAMPLES 21 TO 24

Lubricant oil compositions are individually prepared by mixing the compound [S3] and Aromix 20T in various weight ratios indicated in Table 6. Then, a miscibility test is

TABLE 6

| | Component I: Compound (A) | Component II: Compound (B) | Weight ratio of I/II | Lower limit temperature for lubricant oil composition to be miscible with HFC-134a (see Note *) |
|---|---|---|---|---|
| Example 21 | [S3] | Aromix 20T | 80/20 | −62° C. |
| Example 22 | [S3] | Aromix 20T | 70/30 | −60° C. |
| Example 23 | [S3] | Aromix 20T | 60/40 | −55° C. |
| Example 24 | [S3] | Aromix 20T | 50/50 | −35° C. |

Note
*Weight ratio of lubricant oil composition/mixed refrigerant (HFC-32, HFC-125 and HFC-134a): 90/10

As is apparent from Examples 21 to 24, the lubricant oil compositions prepared by mixing the fluorine-containing aromatic compound (A), particularly represented by formula (C-1), and the alkyl- or alkyl derivative-substituted aromatic compound (B) in various weight ratios exhibit a good miscibility with a mixed refrigerant of HFC-32/HFC-125/HFC-134a (weight ratio: 30/10/60) even at low temperatures.

EXAMPLES 25 TO 27

A lubricant oil composition is prepared by mixing the compound [S3] and Aromix 20T in a weight ratio ([S3]/

Aromix 20T) of 80/20. Then, a miscibility test is conducted in substantially the same manner as in Example 4, except that a mixed refrigerant of HFC- 143a/HFC-134a/HFC-125 (weight ratio: 52/4/44) is used as the refrigerant in place of HFC-134a, and that the weight ratio of the lubricant oil composition to the refrigerant is varied as indicated in Table 7, thereby evaluating the miscibility of the lubricant oil composition with the mixed refrigerant of HFC-143a/HFC-134a/HFC-125. Results are shown in Table 7.

TABLE 7

| | Weight ratio of lubricant oil composition*/ mixed refrigerant** | Lower limit temperature for lubricant oil composition to be miscible with mixed refrigerant |
|---|---|---|
| Example 25 | 70/30 | –70° C. |
| Example 26 | 40/60 | –37° C. |
| Example 27 | 5/95 | –32° C. |

Note
*Weight ratio of [S3]/Aromix 20T: 80/20
**Weight ratio of HFC-143a/HFC-134a/HFC-125: 52/4/44

As is apparent from Examples 25 to 27, the lubricant oil composition comprising a fluorine-containing aromatic compound (A), particularly represented by formula (C-1), and the alkyl- or alkyl derivative-substituted aromatic compound (B) exhibits a good miscibility with a mixed refrigerant of HFC-143a/HFC- 134a/HFC-125 (weight ratio: 52/4/44) even at low temperatures, with respect to various mixing ratios of the lubricant oil composition to the mixed refrigerant.

EXAMPLE 28

A lubricant oil composition is prepared by mixing the compound [S3] and Aromix 20T in a weight ratio ([S3]/Aromix 20T) of 80/20. Then, a miscibility test is conducted in substantially the same manner as in Example 4, except that a mixed refrigerant of HFC-32/HFC- 125/HFC-134a (weight ratio: 23/25/52) is used as the refrigerant in place of HFC-134a, to thereby evaluate the miscibility of the lubricant oil composition with the mixed refrigerant of HFC-32/HFC-125/HFC-134a.

It is found that the lubricant oil composition is miscible with the mixed refrigerant of HFC-32/HFC- 125/HFC-134a at room temperature and the lower limit temperature for miscibility is –70° C.

EXAMPLE 29

A lubricant oil composition is prepared by mixing the compound [S4] and Aromix 20T in a weight ratio ([S4]/Aromix 20T) of 80/20. Then, a miscibility test is conducted in substantially the same manner as in Example 4, except that a mixed refrigerant of HFC- 32/HFC-125/HFC134a (weight ratio: 30/10/60) is used as the refrigerant in place of HFC-134a, to thereby evaluate the miscibility of the lubricant oil composition with the mixed refrigerant of HFC-32/HFC-125/HFC-134a.

It is found that the lubricant oil composition is miscible with the mixed refrigerant of HFC-32/HFC- 125/HFC-134a at room temperature, and also even at a temperature as low as –78° C.

EXAMPLE 30

A lubricant oil composition is prepared by mixing the compound [S5] [compound (A)] obtained in Referential Example 5 and Aromix 20T in a weight ratio ([S5]/Aromix 20T) of 80/20. Then, a miscibility test is conducted in substantially the same manner as in Example 4, except that a mixed refrigerant of HFC- 32/HFC-125/HFC-134a (weight ratio: 30/10/60) is used as the refrigerant in place of HFC-134a, to thereby evaluate the miscibility of the lubricant oil composition with the mixed refrigerant of HFC-32/HFC-125/HFC-134a.

It is found that the lubricant oil composition is miscible with the mixed refrigerant of HFC-32/HFC- 125/HFC-134a at room temperature, and also even at a temperature as low as –50° C.

EXAMPLE 31

Alken 56N (trade name of (branched)alkylbenzene having a kinetic viscosity at 40° C. of 5.8 cSt, manufactured by Nippon Petroleum Detergent Co., Ltd.) and Aromix 22 (trade name of (branched)alkylbenzene having a kinetic viscosity at 40° C. of 29 cSt, manufactured by Nippon Petroleum Detergent Co., Ltd.) are mixed in a weight ratio (Alken 56N/Aromix 22) of 45/55, thereby obtaining an alkyl- or alkyl derivative-substituted compound (B) (having a kinetic viscosity at 40° C. of 14 cSt). Subsequently, the thus obtained compound (B) is mixed with the compound [S3] in a weight ratio ([S3]/the compound (B)) of 80/20, thereby preparing a lubricant oil composition. Then, a miscibility test is conducted in substantially the same manner as in Example 4 except that the mixing ratio of the lubricant oil composition/HFC-134a is changed to 70/30 by weight ratio.

It is found that the lubricant oil composition exhibits an excellent miscibility with HFC-134a at room temperature and that the lower limit temperature for miscibility is –50° C.

EXAMPLES 32 THROUGH 35

Miscibility tests are conducted in substantially the same manner as in Example 4, except that a mixed refrigerant of HFC-32/HFC-125/HFC-134a (weight ratio: 30/10/60) is used as the refrigerant in place of HFC- 134a, to thereby evaluate the miscibilities of the lubricant oil compositions comprising the compound [S3] and each of the alkyl- or alkyl derivative-substituted aromatic compound (B) shown in Table 8 with the mixed refrigerant of HFC-32/HFC-125/HFC-134a. Results are shown in Table 8.

TABLE 8

| | Component I: Compound (A) | Component II: Compound (B) | Weight ratio of (I)/(II) | Kinetic viscosity (cSt) at 40° C. | Lower limit temperature for lubricant oil composition to be miscible with refrigerant*[1] |
|---|---|---|---|---|---|
| Example 32 | [S3] | Aromix 22: (branched) alkylbenzene | 70/30 | 59 | –30° C. |
| Example 33 | [S3] | di(branched)*[2] | 62/38 | 51 | –30° C. |

TABLE 8-continued

| | Component I: Compound (A) | Component II: Compound (B) | Weight ratio of (I)/(II) | Kinetic viscosity (cSt) at 40° C. | Lower limit temperature for lubricant oil composition to be miscible with refrigerant*1 |
|---|---|---|---|---|---|
| Example 34 | [S3] | alkylbenzene Aromix 200P:*3 (linear) alkylbenzene | 60/40 | 53 | −13° C. |
| Example 35 | [S3] | di(linear)*4 alkylbenzene | 71/29 | 51 | −13° C. |

*1Lubricant composition/mixture of refrigerants (HFC-32/HFC-125/HFC-134a = 30/10/60 by wt) = 90/10 by wt
*2Barrel Process Oil B-32AB, manufactured by Matsumura Oil Co., Ltd. (kinetic viscosity at 40° C.; 32 cSt)
*3Manufactured by Nippon Petroleum Detergent Co., Ltd. (kinetic viscosity at 40° C.; 26 cSt)
*4Barrel Process Oil B-27, manufactured by Matsumura Oil Co., Ltd. (kinetic viscosity at 40° C.; 27 cSt)

From the results shown in Table 8, it is apparent that each lubricant oil composition comprising a fluorine-containing aromatic compound (A), particularly represented by formula (C-1), and (branched)alkylbenzene [compound (B)] exhibits an excellent miscibility with the mixed refrigerant of HFC-32/HFC-125/HFC-134a in a further low temperature range, as compared to a lubricant oil composition comprising (linear)alkylbenzene as compound (B).

EXAMPLE 36

A lubricant oil composition is prepared by mixing the compound [S3] with an alkyldiphenyl ether [compound (B)] (LB-15, having a kinetic viscosity at 40° C. of 15 cSt, manufactured by Matsumura Oil Research Co., Ltd.) in a weight ratio ([S3]/alkyldiphenyl ether) of 82/18. Then, a miscibility test is conducted by mixing the lubricant oil composition and HFC-134a in a weight ratio (the oil composition/HFC-134a) of 70/30 in substantially the same manner as in Example 4, to thereby evaluate the miscibility of the lubricant oil composition with HFC-134a.

It is found that the lubricant oil composition is miscible with HFC-134a at room temperature and that the lower limit temperature for miscibility is −42° C.

EXAMPLES 37 THROUGH 42

Each of the compounds [S1], [S3], and [S4] is individually mixed with each of various types of hydrofluoroether (HFE) refrigerants indicated in table 9 in a weight ratio (the compound/the HFE refrigerant) of 10/90. The miscibilities of each of the compounds (A) with the various types of HFE refrigerants are evaluated in substantially the same manner as in Example 4. Results are shown in Table 9.

COMPARABLE EXAMPLES 9 THROUGH 13

In each comparable example, a perfluoropolyether (Fomblin Y-06, having a kinetic viscosity at 40° C. of 27 cSt, manufactured by NIPPON MONTEDISON KK) or a mineral oil (SUNISO 3GS, manufactured by Japan Sun Oil Company, Ltd) is mixed with various types of HFE refrigerants in a weight ratio (the lubricant oil/the fluorine-containing ether) of 10/90. The miscibilities of each of the lubricant oils with the various types of HFE refrigerants are evaluated in substantially the same manner as in Example 4. Results are shown in Table 9.

TABLE 9

| | Component I: Compound (A) or other fluoro compounds | Component II: Compound (B) or non-aromatic compounds | Weight ratio of (I)/(II) | HFE refrigerant | Lower limit temperature for lubricant oil composition to be miscible with refrigerant*1 |
|---|---|---|---|---|---|
| Ex. 37 | [S1] | — | — | $CHF_2OCH_2CF_3$ | lower than −78° C. |
| Ex. 38 | [S4] | — | — | $CHF_2OCH_2CF_3$ | lower than −78° C. |
| Ex. 39 | [S3] | — | — | $CHF_2OCH_2CF_3$ | lower than −78° C. |
| Ex. 40 | [S3] | — | — | $CH_3OCH_2CF_2CF_3$ | lower than −78° C. |
| Ex. 41 | [S3] | — | — | $CH_3CH_2OCF_2CHF_2$ | lower than −78° C. |
| Ex. 42 | [S3] | — | — | $CHF_2OCH_2CF_3/$ $CF_3CH_2F$ | lower than −78° C. |
| Comp. Ex. 9 | perfluoropolyether*2 | — | — | $CHF_2OCH_2CF_3$ | higher than room temperature*4 |
| Comp. Ex. 10 | perfluoropolyether*2 | — | — | $CH_3CH_2OCF_2CHF_2$ | higher than room temperature*4 |
| Comp. Ex. 11 | — | mineral oil*3 | — | $CHF_2OCH_2CF_3$ | higher than room temperature |
| Comp. Ex. 12 | — | mineral oil*3 | — | $CH_3OCH_2CF_2CF_3$ | higher than room temperature*4 |
| Comp. Ex. 13 | — | mineral oil*3 | — | $CH_3CH_2OCF_2CHF_2$ | higher than room temperature*4 |

*1Lubricant/HFE refrigerant = 10/90 by wt
*2Fomblin Y-06 manufactured by NIPPON MONTEDISON K.K. (kinetic viscosity at 40° C.; 27 cSt)
*3SUNISO 3GS manufactured by Japan Sun Oil Company, Ltd. (kinetic viscosity at 40° C.; 30 cSt)
*4room temperature; 22° C.

From the results shown in Table 9, it is apparent that a perfluoropolyether and a mineral oil exhibit an unsatisfactory miscibility with HFE refrigerants, while fluorine-containing aromatic compounds (A) represented by formula (A) exhibit excellent miscibility with various types of HFE refrigerants.

EXAMPLES 43 AND 44

Lubricant oil compositions are individually prepared by mixing the compound [S3] with each of the alkyl- or alkyl derivative-substituted aromatic compounds (B) indicated in Table 10 in a weight ratio indicated in Table 10. Each of the obtained oil composition is individually mixed with each of various HFE refrigerants in a weight ratio (Lubricant oil/ HFE refrigerant) of 70/30. The miscibility of each of the lubricant oil compositions with each of the HFE refrigerants is evaluated in substantially the same manner as in Example 4. Results are shown in Table 10.

COMPARABLE EXAMPLES 14 AND 15

Each of a perfluoropolyether (Fomblin Y-06, having a kinetic viscosity at 40° C. of 27 cSt, manufactured by NIPPON MONTEDISON KK) and a mineral oil (SUNISO 3GS, manufactured by JAPAN SUN OIL COMPANY, Ltd) is individually mixed with each of various HFE refrigerants in a weight ratio (lubricant oil/HFE refrigerant) of 70/30. Then the miscibility of each of the lubricant oils with each of the various types of HFE refrigerants are evaluated in substantially the same manner as in Example 4. Results are shown in Table 10.

With respect to the lubricant oil compound [S3] alone and the lubricant oil compositions shown in Table 11, the pour points are measured according to the method of JIS K2269-1987 (pour point test). Results are shown in Table 11.

TABLE 11

| Example | Component I: Compound (A) | Component II: Compound (B) | Weight ratio of (I)/(II) | Pour point |
|---|---|---|---|---|
| 45 | [S3] | — | — | −15° C. |
| 46 | [S3] | Aromix 20T | 50/50 | −35° C. |
| 47 | [S3] | Aromix 22 | 50/50 | −33° C. |
| 48 | [S3] | AB-SG | 50/50 | −60° C. |

From the results of Table 11, it is apparent that the fluidity at low temperatures is markedly improved by mixing the fluorine-containing aromatic compound (A) with the alkyl- or alkyl derivative-substituted aromatic compound (B).

EXAMPLES 49 THROUGH 52

<Water Absorption Test>

The lubricant oil compound [S3] alone or the lubricant oil compositions individually comprised of the compound [S3] and each of the various alkyl- or alkyl derivative-substituted aromatic compounds shown in Table 12 are individually allowed to stand in a thermo-hygrostat vessel maintained at a temperature of 25° C. and at a relative humidity of 70%, and the equilibrium water absorptions thereof are measured, by means of Karl Fischer moisture meter. Results are shown in Table 12.

TABLE 10

| | Component I: Compound (A) or other fluoro compound | Component II: Compound (B) or non-aromatic compound | Weight ratio of (I)/(II) | HFE refrigerant | Lower limit temperature for lubricant oil composition to be miscible with refrigerant*[1] |
|---|---|---|---|---|---|
| Ex. 43 | [S3] | Aromix 20T | 80/20 | $CHF_2OCH_2CF_3$ | lower than −78° C. |
| Ex. 44 | [S3] | alkyldiphenylether*[3] | 90/10 | $CH_3CH_2OCF_2CHF_2$ | lower than −78° C. |
| Comp. Ex. 14 | perfluoropolyether*[2] | — | — | $CH_3CH_2OCF_2CHF_2$ | higher than room temperature*[5] |
| Comp. Ex. 15 | — | mineral oil*[4] | — | $CH_3CH_2OCF_2CHF_2$ | higher than room temperature*[5] |

*[1]Lubricant/HFE refrigerant = 70/30 by wt
*[2]Fomblin Y-06 manufactured by NIPPON MONTEDISON K.K. (kinetic viscosity at 40° C.; 27 cSt)
*[3]MORESCO Highlub LB-15 manufactured by Matsumura Research Oil Co., Ltd. (kinetic viscosity at 40° C.; 15 cSt)
*[4]SUNISO 3GS manufactured by Japan Sun Oil Company, Ltd. (kinetic viscosity at 40° C.; 30 cSt)
*[5]room temperature; 22° C.

From the results shown in Table 10, it is apparent that a perfluoropolyether and a mineral oil exhibit an unsatisfactory miscibility with HFE refrigerants, while lubricant oil compositions comprising the fluorine-containing aromatic compound (A) and the alkyl- or alkyl derivative-substituted aromatic compound (B) exhibit excellent miscibility with various HFE refrigerants even in a lower temperature range.

EXAMPLES 45 THROUGH 48

<Pour Point Test>

COMPARATIVE EXAMPLE 16

The equilibrium water absorption of a lubricant oil composition comprised of the compound [S3] and an ester oil (pentaerythritol fatty acid ester having a kinetic viscosity of 32 cSt at 40° C.) is measured in the same manner as described in Example 49. Result is shown in Table 12.

TABLE 12

| | Component I: Compound (A) | Component II: Compound (B) or non-aromatic compound | Weight ratio of (I)/(II) | Equilibrium water absorption *[1] (ppm) |
|---|---|---|---|---|
| Ex. 49 | [S3] | — | — | 250 |
| Ex. 50 | [S3] | Aromix 20T | 50/50 | 140 |
| Ex. 51 | [S3] | Aromix 22 | 50/50 | 130 |

TABLE 12-continued

|  | Component I: Compound (A) | Component II: Compound (B) or non-aromatic compound | Weight ratio of (I)/(II) | Equilibrium water absorption *1 (ppm) |
|---|---|---|---|---|
| Ex. 52 | [S3] | Aromix 100P | 50/50 | 110 |
| Comp. Ex. 16 | [S3] | ester oil | 50/50 | 430 |

TABLE 12-continued

|  | Component I: Compound (A) | Component II: Compound (B) or non-aromatic compound | Weight ratio of (I)/(II) | Equilibrium water absorption *1 (ppm) |
|---|---|---|---|---|

*1 Equilibrium water absorption measured at 25° C. and at a relative humidity of 70%
*2 pentaerythritol fatty acid ester (kinetic viscosity at 4° C.: 32 cSt)

Table 12 clearly shows that the water absorption is markedly lowered when the fluorine-containing aromatic compound (A), particularly represented by formula (C-1), is mixed with the alkyl or alkyl derivative-substituted aromatic compound (B).

EXAMPLES 53 AND 54

The equilibrium water absorptions of compound [S4] and compound [S8], both of which fall within the class of compound (A), respectively obtained in Referential Examples 4 and 8 are measured in the same manner as described in Example 49. Results are shown in Table 13.

COMPARATIVE EXAMPLE 17

The equilibrium water absorption of an ester oil (pentaerythritol fatty acid ester having a kinetic viscosity of 32 cSt at 40° C.) is measured in the same manner as described in Example 49. A result is shown in Table 13.

TABLE 13

|  | Compound (A) or other compound | Equilibrium water absorption *1 (ppm) |
|---|---|---|
| Ex. 53 | [S4] | 190 |
| Ex. 54 | [S8] | 150 |
| Comp. Ex. 17 | ester oil | 1300 |

*1 Equilibrium water absorption measured at 25° C. and at a relative humidity of 80%

Table 13 clearly shows that the fluorine-containing aromatic compounds (A), particularly represented by formula (C-2), have lower water absorbing properties.

EXAMPLES 55 THROUGH 57

<Electrical Properties>

The volume resistivities of the lubricant oil [S3] and the lubricant oil compositions individually comprised of the oil [S3] and each of the alkyl- or alkyl derivative-substituted aromatic compounds shown in Table 14 are individually measured according to the method of JIS C2101 (insulating oil test). Results are shown in Table 14.

TABLE 14

|  | Component I: Compound (A) | Component II: Compound (B) | Weight ratio of (I)/(II) | Volume resistivity ($\Omega$cm) | |
|---|---|---|---|---|---|
|  |  |  |  | before water absorption *1 | after water absorption *2 |
| Ex. 55 | [S3] | — | — | $2.0 \times 10^{13}$ | $1.0 \times 10^{12}$ |
| Ex. 56 | [S3] | Aromix 20T | 80/20 | $2.1 \times 10^{13}$ | $1.0 \times 10^{13}$ |
| Ex. 57 | [S3] | Aromix 22 | 50/50 | $1.1 \times 10^{14}$ | $5.0 \times 10^{13}$ |

*1 Amount of water absorbed < 10 ppm
*2 Equilibrium water absorption measured at 25° C. and at a relative humidity of 70%

Table 14 clearly shows that the decrease in volume resistivity of each of the lubricant oil compositions due to the water absorption is less than that of the oil alone.

EXAMPLE 58

<Bioconcentration Test>

The test is conducted substantially in accordance with <Method for Testing the Degree of Bioconcentration of Chemical Substances in Fishes> promulgated in "Test Relating to the New Chemical Substance" (Japanese Environment Agency Notification, No. KANPOGYO 5, Japanese Ministry of Health and Welfare Notification, No. YAKUHATSU 615, and Japanese Ministry of International Trade and Industry 49 KIKYOKU Notification No. 392, July 13, 1974) and <Bioaccumulation: Degree of Bioconcentration in Fish> promulgated in "OECD Guidelines for Testing of Chemicals, 305C" (May 12, 1981).

The illustrative procedure of the test is described below in detail. The compound [S3] is dissolved in water to prepare a test solution having a compound [S3] concentration of 0.01 mg/liter. Normal carps, after acclimatization, are subjected to exposure test in the test solution. After 2-week and 4-week exposures, the carps are collected. The fishes are minced, homogenized and subjected to centrifugation. After the centrifugation, the degree of bioconcentration of the compound [S3], which is defined as a ratio of the concentration of the compound [S3] in a fish body to that of the test solution, is measured by high performance liquid chromatography. Results are shown in Table 15.

EXAMPLES 59 AND 60

The degrees of bioconcentration are measured also with respect to the compound [S9] obtained in Referential Example 9 and the compound [S1] obtained in Referential Example 1, in the same manner as described in Example 58. Results are shown in Table 15.

TABLE 15

| | Fluorine-containing aromatic Compound (A) | Degree of bioconcentration | |
|---|---|---|---|
| | | after 2 weeks | after 4 weeks |
| Ex. 58 | [S3] | 303 | 583 |
| Ex. 59 | [S9] | 3990 | 9240 |
| Ex. 60 | [S1] | 4400 | 11900 |

Table 15 clearly shows that the degree of bioconcentration of the compound represented by formula (C-1) is especially low among the compounds (A).

EXAMPLE 61

The degree of bioconcentration of the compound S4] is measured in the same manner as described in Example 58. After 4-week exposure, it is found that the bioconcentration of the compound [S4] in the carp increases 2260-fold, at which an equilibrium is reached. This shows that the degree of bioconcentration of the compound [S4] is low.

EXAMPLES 62 AND 63

<Heat Resistance>

The fluorine-containing aromatic compounds [S3] and [S6] [compound (A)] obtained in Referential Example are evaluated with respect to the heat resistance by a method described below. A glass tube is charged with 0.5 ml of each of the compound [S3] and the compound [S6], individually. Each of the compounds is individually heated and kept at a temperature of 175° C. for 19 hours under air. The obtained substance is analyzed by gas chromatography to examine if the compound is thermally decomposed. Results are shown in Table 16.

EXAMPLES 64 AND 65

The compound [S10] and [S11] obtained, respectively, in Referential Examples 10 and 11 are evaluated with respect to the heat resistance by the same method as described in Example 62. Results are shown in Table 16.

TABLE 16

| | Fluorine-containing aromatic compound (A) | Degree of thermal decomposition *1 |
|---|---|---|
| Ex. 62 | [S3] | less than 0.01% |
| Ex. 63 | [S6] | 0.2% |
| Ex. 64 | [S10] | 10% |
| Ex. 65 | [S11] | 20% |

*1 gas chromatography (area % of peaks for thermal decomposition products, based on the total area of chromatogram)

Table 16 clearly shows that, among the compounds (A) represented, the compounds of formula (C-1) exhibit especially high heat resistance.

EXAMPLES 66 AND 67

The compounds [S4] and [S8] are evaluated with respect to the heat resistance in the same manner as described in Example 62. Results are shown in Table 17.

EXAMPLES 68 THROUGH 70

The compound [S12], [S13] and [S14] obtained, respectively, in Referential Examples 12, 13 and 14 are evaluated with respect to the heat resistance by the same method as described in Example 62. Results are shown in Table 17. [The Compounds [S13] and [S14] are derivatives of an alkylphenol derivative synthesized from a propylene oligomer. The structures of the alkyl groups bonded to an aromatic nucleus are of the mixture of secondary alkyl and tertiary alkyl structures.]

TABLE 17

| | Fluorine-containing aromatic compound (A) | Degree of thermal degradation *1 |
|---|---|---|
| Ex. 66 | [S4] | less than 0.01% |
| Ex. 67 | [S8] | 0.1% |
| Ex. 68 | [S12] | 15% |
| Ex. 69 | [S13] | 4% |
| Ex. 70 | [S14] | 3% |

*1 gas chromatography (area % of peaks for thermal decomposition products, based on the total area of chromatogram)

Table 17 clearly shows that, among the compounds (A) of the present invention represented by formula (A), the fluorine-containing aromatic compounds (A) of formula (C-2) have especially high heat resistance properties.

EXAMPLES 71 THROUGH 73

<Lubrication Test (Falex Test)>

Lubrication tests are conducted with respect to the lubricant oils [S3] and [S4] and the lubricant oil compositions indicated in Table 18 under conditions described below.

Use is made of a Falex tester. First, a refrigerant gas (HFC-134a) is blown into a sample (oil or an oil composition) at a blow rate of about 10 liter/hour for about 15 minutes. Further, under conditions such that the oil temperature at the start of the testing is 25° C. and a load of 200 pounds is applied, the Falex tester is driven for 5 minutes while continuing the gas blowing. The load is increased to 500 pounds, and the tester is driven for 2 hours while maintaining the load at 500 pounds by means of a gear.

The weight of V-block and pin (test specimen) is measured before and after the test run, and the weight difference before and after the test run is defined as "wear (mg)". Results are shown in Table 18.

EXAMPLES 74 THROUGH 78

The lubricant oils [S3] and [S4] and the lubricant oil compositions indicated in Table 18 are individually mixed with each of various types of additives also indicated in Table 18, and the resultant mixtures are measured with respect to the weight loss of V-block and pin in the same manner as described in Example 71. Results are shown in Table 18.

COMPARATIVE EXAMPLES 18 AND 19

The abrasion losses of aromatic compounds containing no fluorine, including Aromix 20T and SUNISO3GS, are measured in the same manner as described in Example 71. Results are shown in Table 18.

TABLE 18

| | Component I: Compound (A) | Component II: Compound (B) or non-aromatic compound | Weight ratio of I/II | Additives | Falex test: wear (mg) |
|---|---|---|---|---|---|
| Ex. 71 | [S3] | — | — | none | 18 |
| Ex. 72 | [S-3]/[S-4]*[1] | — | — | none | 21 |
| Ex. 73 | [S-3] | Aromix 20T | 80/20 | none | 8 |
| Ex. 74 | [S-3]/[S-4]*[1] | — | — | TCP*[2] | 2 |
| Ex. 75 | [S-3] | Aromix 20T | 80/20 | TCP*[2] | 0.6 |
| Ex. 76 | [S-3] | Aromix 20T | 80/20 | TCP*[2] Benzotriazole*[3] | 0.3 |
| Ex. 77 | [S-3] | Aromix 20T | 80/20 | TCP*[2] 2-ethylhexyl grycizylether*[4] | less than 0.1 |
| Ex. 78 | [S-3] | Aromix 20T | 80/20 | TCP*[2] Benzotriazole*[3] 2-ethylhexel grycizylether*[4] | 0.2 |
| Comp. Ex. 18 | — | Aromix 20T | — | none | seizure |
| Comp. Ex. 19 | — | SUNISO3GS | — | none | seizure |

*[1][S-3]/[S-4] = 87.5/12.5 by wt (kinetic viscosity at 40° C.; 56.7 cSt)
*[2]Tricresyl phosphate; amount added 0.5 wt %
*[3]Amount added 0.001 wt %
*[4]Amount added 0.25 wt %

As is apparent from Table 18, the lubricant oil compositions each comprised of the fluorine-containing aromatic compound (A) of formula (C-1) and the alkyl or alkyl derivative-substituted aromatic compound (B) have excellent abrasion resistance properties, as compared to the alkyl- or alkyl derivative-substituted aromatic compounds (B) alone as well as the fluorine-containing aromatic compounds (A).

EXAMPLES 79 THROUGH 82

<Resistance to Hydrolysis>

Each of the fluorine-containing lubricant oils and the each of the fluorine-containing oil compositions indicated in Table 19 is individually allowed to absorb water to equilibrium in the same manner as described in Example 49. A glass tube is charged with 0.6 ml of each of the oils and the oil compositions, 0.6 ml of HFC-134a as liquid, 2 ml of air as gas, and a metal piece selected from steel, copper and aluminum. The glass tube is then sealed to enclose a refrigerant composition therein. The refrigerant composition is heated at 175° C. for 10 days. After the heating, any change in the hue of the refrigerant composition and any change in the surfaces of the metal piece are examined. It is found that both the hue of the refrigerant composition of the present invention and the surface of the metal are not changed. After evaluation, the oils and the oil compositions are analyzed by gas chromatography/mass spectrometry (GC/MASS). No decomposition is detected with respect to each of the fluorine-containing oils and with respect to each of the fluorine-containing oil compositions of the present invention. Further, the color change of the copper surface, which is slightly observed with respect to the lubricant oil alone, is not observed with respect to the fluorine-containing oil composition, i.e., the mixture of the fluorine-containing lubricant oil and the aromatic compound (B). Results are shown in Table 19.

COMPARATIVE EXAMPLE 20

Ester oil (pentaerythritol fatty acid ester having a kinetic viscosity of 32 cSt at 40° C.) is allowed to absorb water to equilibrium in the same manner as described in Comparative Example 17. The obtained ester oil is evaluated with respect to the heat resistance and hydrolysis resistance in the same manner as described in Example 79. In the ester oil evaluated, decomposition products are detected. Results are shown in Table 19.

TABLE 19

| | Component I: Compound (A) | Component II: Compound (B) | Weight ratio of I/II | Additives | Refrigerant composition hue | Decomposition*[2] of Lubricant oil (composition) | Surface of metal | | |
|---|---|---|---|---|---|---|---|---|---|
| | | | | | | | Fe | Al | Cu |
| Ex. 79 | [S-3] | — | — | none | no change observed | none | no change observed | no change observed | slight color change |
| Ex. 80 | [S-4] | — | — | none | no change observed | none | no change observed | no change observed | slight color change |
| Ex. 81 | [S-3] | Aromix 20T | 80/20 | none | no change observed | none | no change observed | no change observed | no change observed |
| Ex. 82 | [S-3] | Aromix 20T | 80/20 | TCP*[1] | no change | none | no change | no change | no change |

TABLE 19-continued

| | Component I: Compound (A) | Component II: Compound (B) | Weight ratio of I/II | Additives | Refrigerant composition hue | Decomposition*2 of Lubricant oil (composition) | Surface of metal | | |
|---|---|---|---|---|---|---|---|---|---|
| | | | | | | | Fe | Al | Cu |
| Comp. Ex. 20 | ester oil | — | — | none | no change observed | detected | no change observed | no change observed | no change observed |

*1Tricresyl phosphate; Amount added 0.5 wt %
*2Decomposition due to hydrolysis is analyzed by GC/MASS.

As is apparent from Table 19, the refrigerant compositions using compound (A) alone as well as the refrigerant compositions using the lubricant oil composition composed of both of compound (A) and compound (B), exhibit satisfactory heat resistance and hydrolysis resistance.

EXAMPLES 83 THROUGH 85

Each of the lubricant oil compositions indicated in Table 20 are evaluated with respect to the resistance to hydrolysis in the same manner as described in Example 79, except the temperature is elevated from 175° C. to 200° C. and the heating duration is prolonged from 10 days to 14 days so as to render the test conditions harder. Results are shown in Table 20.

From Table 20, it is understood that anti-corrosives, such as benzotriazole and 2-ethylhexyl glycidyl ether, are effective to inhibit the color change of the surface of the metal piece.

It is found that the compound [S15] is completely miscible with HFC-134a to form a homogeneous refrigerant composition.

EXAMPLES 87 THROUGH 90

Substantially the same procedure as in Example 86 is repeated except that each of the compounds [S16] to [S19] respectively obtained in Referential Examples 16 to 19 is used instead of the compound [S15], thereby evaluating the miscibility of the oil compounds with HFC-134a at 0° C.

It is found that all of the oil compounds are completely miscible with HFC-134a to form homogeneous refrigerant compositions.

EXAMPLE 91

<Miscibility Test between a lubricant oil composition and HFC-134a>

TABLE 20

| | Component I: Compound (A) | Component II: Compound (B) or non-aromatic compound | Weight ratio of I/II | Additives | Refrigerant composition hue | Decomposition*4 of Lubricant oil (composition) | Surface of metal | | |
|---|---|---|---|---|---|---|---|---|---|
| | | | | | | | Fe | Al | Cu |
| Ex. 83 | [S-3] | Aromix 20T | 80/20 | TCP*1 | no change observed | none | slight color change | no change observed | no change observed |
| Ex. 84 | [S-3] | Aromix 20T | 80/20 | TCP*1 benzotri- azole*2 | no change observed | none | no change observed | no change observed | no change observed |
| Ex. 85 | [S-3] | Aromix 20T | 80/20 | TCP*1 benzotri- azole*2 2-ethyl- hexyl glycidyl- ether*3 | no change observed | none | no change observed | no change observed | no change observed |

*1Tricresyl phosphate; Amount added 0.5 wt %
*2Amount added 0.001 wt %
*3Amount added 0.25 wt %
*4Decomposition due to hydrolysis is analyzed by GC/MASS.

EXAMPLE 86

<Miscibility Test between compound (A) and HFC-134a>

The compound [S15] [compound (A)] obtained in Referential Example 15 is evaluated with respect to the miscibility with HFC-134a as a refrigerant by the following method.

First, 1.8 g of oil compound [S15] is charged in a glass tube having an inner volume of 6 ml and then, the whole is cooled using liquid nitrogen. The interior of the glass tube is evacuated and, about 0.2 g of HFC-134a is introduced into the glass tube. The glass tube is sealed, and the miscibility of the oil compound [S15] with HFC-134a at 0° C. is visually evaluated.

The compound [S15] is mixed with ethylbenzene in a weight ratio ([S15]/ethylbenzene) of 80/20, to thereby obtain a lubricant oil composition. The miscibility of the obtained lubricant oil composition with HFC-134a is evaluated in the same manner as described in Example 86.

It is found that the oil composition is completely miscible with HFC-134a to form a homogeneous refrigerant composition.

EXAMPLES 92 THROUGH 95

Substantially the same procedure as in Example 91 is repeated except that each of the lubricant oil compositions respectively containing compounds [S16] to [S19] [compound (A)] obtained respectively in Referential Examples 16 to 19 instead of the compound [S15] is used, thereby evaluating the miscibility of each of the lubricant oil compositions with HFC-134a at 0° C.

It is found that all of the lubricant oil compositions are completely miscible with HFC-134a to form homogeneous refrigeous refrigerant compositions.

EXAMPLE 96

The compound [S3] is mixed with a compound [E1] represented by the formula indicated below (having a kinetic viscosity of 18 cSt at 40° C.), in a weight ratio ([S3]/[E1]) of 80/20, to thereby obtain a lubricant oil composition (having a kinetic viscosity of 59 cSt at 40° C.). The miscibility of the oil composition with a mixed refrigerant of HFC-134a is evaluated in the same manner as in Example 4, except that a mixed refrigerant of HFC-32/HFC-125/HFC-134a (mixed in a weight ratio of 30/10/60) is used as a hydrofluoroalkane in place of HFC-134a. The oil composition is mixed with the mixed refrigerant in a weight ratio of 70/30.

It is found that the oil composition is miscible with the refrigerant at room temperature and also at –30° C. to form a homogeneous composition.

30/10/60) is used as a HFC refrigerant in place of HFC-134a. The oil composition is mixed with the mixed refrigerant in a weight ratio of 70/30.

It is found that the oil composition is miscible with the HFC refrigerant at room temperature and also at –30° C. to form a homogeneous composition.

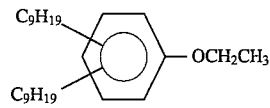

[E2]

COMPARATIVE EXAMPLES 21 THROUGH 25

<Miscibility Test between perfrluoropolyether and compound (B)>

The miscibility of each of the various perfluoropolyethers indicated in Table 21 with Aromix 20T at 25° C. is individually evaluated in the same manner as described in Example 1. It is found that those perfluoropolyethers are not miscible with Aromix 20T when they are mixed in a weight ratio of 80/20, 50/50 or 20/80 (perfluoropolyether/Aromix 20T).

TABLE 21

| | Component I: Perfluoropolyether | | Component II: | Miscibility of I with II at 25° C. (weight ratio of I/II) | | |
|---|---|---|---|---|---|---|
| | | Mn | Compound (B) | 80/20 | 50/50 | 20/80 |
| Comp. Ex. 21 | Fomblin Y-06*[1] | 1800 | Aromix 20T | Not miscible | Not miscible | Not miscible |
| Comp. Ex. 22 | Fomblin Y-25*[1] | 3000 | Aromix 20T | Not miscible | Not miscible | Not miscible |
| Comp. Ex. 23 | Fomblin Y-45*[1] | 4100 | Aromix 20T | Not miscible | Not miscible | Not miscible |
| Comp. Ex. 24 | KRYTOX 143AY*[2] | 3000 | Aromix 20T | Not miscible | Not miscible | Not miscible |
| Comp. Ex. 25 | DEMNUM S-20*[3] | 2700 | Aromix 20T | Not miscible | Not miscible | Not miscible |

*[1]:
$$CF_3O-(CFCF_2O)_n-(CF_2O)_m-CF_3, \text{ manufactured by Montefluos, Italy}$$
with $CF_3$ branch

*[2]:
$$F-(CFCF_2O)_{m1}-CF_2CF_3, \text{ manufactured by Du Pont, USA}$$
with $CF_3$ branch

*[3]: $F-(CF_2CF_2CF_2O)_{m2}-CF_2CF_3$, manufactured by Daikin Kogyo, Japan

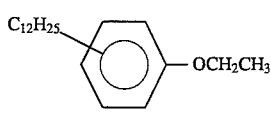

[E1]

EXAMPLE 97

The compound [ S3 ] is mixed with a compound [ E2] represented by the formula indicated below (having a kinetic viscosity of 46 cSt at 40° C.), in a weight ratio ([S3]/[E2]) of 80/20, to thereby obtain a lubricant oil composition (having a kinetic viscosity of 80 cSt at 40° C.). The miscibility of the oil composition with a mixed refrigerant of HFC-32/HFC-125/HFC-134a is evaluated in the same manner as in Example 4, except that a mixed refrigerant of HFC-32/HFC-125/HFC-134a (mixed in a weight ratio of

What is claimed is:

1. A lubricant oil composition comprising:
   (A) a fluorine-containing aromatic compound, and
   (B) an alkyl- or alkyl derivative-substituted aromatic compound, wherein said fluorine-containing aromatic compound (A) is present in an amount of from 0.1 to 99.9% by weight, based on the total weight of said fluorine-containing aromatic compound (A) and said alkyl- or alkyl derivative-substituted aromatic compound (B), said fluorine-containing aromatic compound being represented by the formula:

$$R(XR_f)_n \qquad (A)$$

wherein:

X represents an oxygen or a sulfur atom;

n is an integer of from 1 to 4;

R represents an n-valent aromatic group, having from 6 to 60 carbon atoms, wherein n is as defined above, comprising at least one unsubstituted or substituted aromatic nucleus selected from the group consisting of an unsubstituted or substituted benzene nucleus and an unsubstituted or substituted naphthalene nucleus, wherein the ratio of carbon atoms in the aromatic nucleus of said R to carbon atoms in said R is from 0.10 to 1.0, with the proviso that when said n-valent aromatic group comprises at least two unsubstituted or substituted aromatic nuclei, said at least two aromatic nuclei are linked through a single bond or a linkage group containing no aromatic nuclei and having from 0 to 50 carbon atoms and a valence of from 2 to 6 to form a multinuclear structure; and $R_f$ represents an unsubstituted or partially substituted fluorocarbon group having from 1 to 25 carbon atoms in which the ratio of fluorine atom or atoms to carbon atom or atoms is from 0.6 to 3, wherein said unsubstituted fluorocarbon group is selected from the group consisting of a fluoroalkyl group, a fluoroalkenyl group, a fluoroalkyl group, a fluoroalkylaryl and a fluoroaralkyl group, in which each of the alkyl, alkenyl, aryl, alkylaryl and aralkyl groups is partially or entirely substituted with at least one fluorine atom, and said partially substituted fluorocarbon group has at least one substituent other than fluorine and hydrogen atoms in an amount such that the ratio of said at least one substituent to the total number of fluorine and hydrogen atoms of said partially substituted fluorocarbon group is not greater than 1.5, and wherein a main chain of said unsubstituted or partially substituted fluorocarbon group optionally has from 1 to 7 ether linkages;

wherein when n is an integer of from 2 to 4, the $XR_f$ groups are the same or different; and said alkyl- or alkyl derivative-substituted aromatic compound (B) comprising at least one substituted aromatic nucleus selected from the group consisting of a substituted benzene nucleus and a substituted naphthalene nucleus, wherein a substituent of said at least one substituted aromatic nucleus is an unsubstituted or substituted alkyl group having from 1 to 30 carbon atoms, or a derivative thereof, said alkyl- or alkyl derivative-substituted aromatic compound (B) having a kinetic viscosity of from 0.1 to 500 cSt as measured at 40° C., said lubricant oil composition having a kinetic viscosity of from 2 to 500 cSt as measured at 40° C.

2. The lubricant oil composition according to claim 1, wherein said n-valent aromatic group R of formula (A) is represented by the formula:

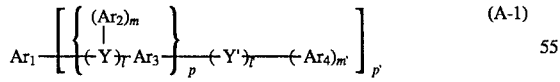
(A-1)

wherein:
p is an integer of from 0 to 2,
p' is an integer of from 0 to 4,
each of l and l' is independently 0 or 1,
m is an integer of from 0 to 2,
m' is an integer of from 0 to 5,
each of $Ar_1$, $Ar_2$, $Ar_3$ and $Ar_4$ is independently an unsubstituted or substituted aromatic nucleus selected from the group consisting of an unsubstituted or substituted benzene nucleus and an unsubstituted or substituted naphthalene nucleus, Y and Y' are multivalent linkage groups having a valence of from 2 to 4 and a valence of from 2 to 6, respectively, and are each independently selected from the group consisting of the following ($a_1$) to ($a_3$):

($a_1$) a 2 to 6-valent saturated or unsaturated hydrocarbon group having from 1 to 20 carbon atoms, which is optionally, partially or entirely substituted with at least one fluorine atom, ($a_2$) a bivalent or a trivalent group having from 0 to 20 carbon atoms selected from the group consisting of the following ($a_2$-1) to ($a_2$-4):

($a_2$-1) an oxygen atom (—O—), ($a_2$-2) a carbonyl-containing multivalent group selected from the group consisting of a carbonyl group, an ester linkage, an amide linkage and a carbonate linkage, ($a_2$-3) a sulfur atom (—S—), or a sulfur-containing multivalent group selected from the group consisting of a sulfonyl group and a sulfinyl group, and ($a_2$-4) a multivalent group containing a nitrogen atom, a phosphorus atom or a silicon atom, which is selected from the group consisting of:

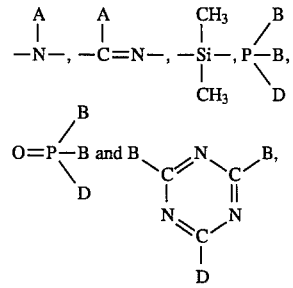

wherein:
A represents a single bond, a hydrogen atom or an alkyl group having from 1 to 6 carbon atoms,
B represents a single bond or an oxygen atom (—O—),
D represents a single bond, an oxygen atom (—O—), —R or —OR in which R represents an alkyl group having from 1 to 20 carbon atoms, ($a_3$) a 2 to 6-valent group having from 1 to 50 carbon atoms and having a structure such that said group ($a_1$) has said group ($a_2$) introduced therein or to a terminal thereof, wherein each of said substituted aromatic nuclei $Ar_1$, $Ar_2$, $Ar_3$ and $Ar_4$ has at least one monovalent substituent independently selected from the group consisting of the following ($b_1$) to ($b_4$):

($b_1$) a monovalent hydrocarbon group having from 1 to 30 carbon atoms, selected from the group consisting of an alkyl, an alkenyl, a cycloalkyl and a cycloalkenyl group, ($b_2$) a monovalent group selected from the group consisting of a hydroxyl group, a thiol group, a nitrile group, a nitro group, a fluorine atom and a chlorine atom, ($b_3$) a substituted monovalent hydrocarbon group having 50 or less carbon atoms, wherein said monovalent hydrocarbon group is substituted with at least one substituent selected from the group consisting of said monovalent group ($b_2$) defined above and said bivalent group ($a_2$) defined for said linkage groups Y and Y', with the proviso that the sum of the number of said monovalent group ($b_2$) and the number of said bivalent group ($a_2$) is from 1 to 3, and ($b_4$) a fluorine-substituted monovalent group having a structure such that at least one hydrogen atom of carbon-to-hydrogen bonds of said monovalent hydrocarbon group ($b_1$) or said substituted monovalent hydrocarbon group ($b_3$) is substituted with a fluorine atom, with the proviso that the sum, per aromatic nucleus, of the number of substituents bonded to the aromatic nucleus of each of $Ar_1$, $Ar_2$, $Ar_3$ and $Ar_4$ and the number of said linkage groups Y and Y' is from 0 to 4 and that each $-XR_f$ group of formula (A) is bonded to a carbon atom of said R group represented by formula (A-1); and wherein said unsubstituted or partially substituted fluorocarbon group $R_f$ of formula (A) is represented by the formula:

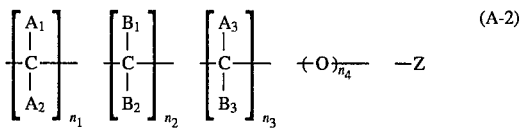 (A-2)

wherein:

each of $A_1$, $A_2$ and $A_3$ is independently a fluorine atom or a fluoroalkyl group having from 1 to 6 carbon atoms, wherein said fluorine atom is optionally replaced with or said fluoroalkyl group is optionally substituted with at least one substituent selected from the group consisting of:

($C_1$) a halogen atom, exclusive of a fluorine atom, ($C_2$) an active hydrogen-containing monovalent group selected from the group consisting of a hydroxyl group, an amino group and a thiol group, with the proviso that said active hydrogen-containing group is not bonded to a carbon atom having a halogen atom, inclusive of a fluorine atom, bonded thereto, and ($C_3$) a monovalent group having from 1 to 10 carbon atoms, selected from the group consisting of a thioalkoxy group, an alkyl-substituted amino group, an acyl group, an acyloxy group, a carboalkoxy group, a nitrile group, an amido group and an imido group, which are optionally substituted with at least one fluorine atom, each of $B_1$, $B_2$ and $B_3$ is independently a hydrogen atom or an alkyl group having from 1 to 6 carbon atoms, wherein said hydrogen atom is optionally replaced with or said alkyl group is optionally substituted with a substituent selected from the group consisting of:

($C_1$) a halogen atom, exclusive of a fluorine atom, ($C_2$) an active hydrogen-containing monovalent group selected from the group consisting of a hydroxyl group, an amino group and a thiol group, with the proviso that said active hydrogen-containing group is not bonded to a carbon atom having a halogen atom, inclusive of a fluorine atom, bonded thereto, and ($C_3$) a monovalent group having from 1 to 10 carbon atoms, selected from the group consisting of a thioalkoxy group, an alkyl-substituted amino group, an acyl group, an acyloxy group, a carboalkoxy group, a nitrile group, an amido group and an imido group, which are optionally substituted with a fluorine atom, Z is a terminal group selected from the group consisting of a hydrogen atom, a fluorine atom, and a phenyl group unsubstituted or substituted with an alkyl group having from 1 to 10 carbon atoms, wherein said unsubstituted or substituted phenyl group is optionally substituted with at least one fluorine atom, $n_1$ is an integer of from 0 to 25, each of $n_2$ and $n_3$ is independently an integer of from 0 to 10, with the proviso that ($n_1$+$n_3$) is not zero, $n_4$ is an integer of from 0 to 7, wherein when $n_1$ is an integer of 2 or more, the ($CA_1A_2$) units are the same or different, when $n_2$ is an integer of 2 or more, the ($CB_1B_2$) units are the same or different, and when $n_3$ is an integer of 2 or more, the ($CA_3B_3$) units are the same or different; and wherein the ($CA_1A_2$), ($CB_1B_2$), ($CA_3B_3$) and $-\!(\!-O-\!)\!-$ are arranged in any order, with the proviso that the $-\!(\!-O-\!)\!-$ units are not directly linked to each other, that the $-\!(\!-O-\!)\!-$ unit is not positioned at a terminal of formula (A-2) and not directly linked to a hydrogen atom or a fluorine atom, and that a main chain of formula (A-2) optionally contains one or two double bonds each formed, between a unit selected from ($CA_1A_2$), ($CB_1B_2$) and ($CA_3B_3$) units and a neighbouring unit selected from ($CA_1A_2$), ($CA_2B_2$) and ($CA_3B_3$), by a connection of $A_1$-$B_1$, $A_1$-$A_3$, $B_1$-$A_3$, $A_2$-$B_2$, $A_2$-$B_3$ or $B_2$-$B_3$ thereof in which each of $A_1$, $A_2$, $A_3$, $B_1$, $B_2$ and $B_3$ is a single bond; and wherein said alkyl- or alkyl derivative-substituted aromatic compound (B) is represented by the formula:

 (B-1)

wherein:

each of $Ar_a$ and $Ar_b$ independently represents a benzene nucleus or a naphthalene nucleus, $n_1$ is an integer of from 0 to 4, $n_2$ is an integer of from 0 to 3, $n_3$ is an integer of from 1 to 3, $n_4$ is an integer of from 0 to 2, with the proviso that when $n_4$ is zero, $n_1$ is not zero and that when $n_4$ is not zero, ($n_1$+$n_2$) is not zero, K is a linkage group selected from the group consisting of:
1) a single bond,
2) a bivalent group selected from the group consisting of an oxygen atom (—O—), a sulfonyl group and a carbonyl group, and
3) a saturated hydrocarbon group having from 1 to 12 carbon atoms and having a valence of 2 to 4, and each of $R_1$ and $R_2$ independently represents an unsubstituted or fluorine-substituted alkyl group having from 1 to 30 carbon atoms, wherein a main chain of said unsubstituted or fluorine-substituted alkyl group optionally has at least one ether linkage introduced therein or to a terminal thereof, with the proviso that the ratio of said at least one ether linkage to all carbon atoms of said alkyl- or alkyl derivative-substituted aromatic compound of formula (B-1) is not more than ⅓, wherein when $n_1$ is an integer of 2 to 4, the $R_1$ groups are the same or different; when $n_2$ is an integer of 2 or 3, the $R_2$ groups are the same or different; when $n_3$ is an integer of 2 or 3, the $R_2$ groups are the same or different and the $Ar_b$ groups are the same or different; and when $n_4$ is 2, the K groups are the same or different, the $R_2$ groups are the same or different and the $Ar_b$ groups are the same or different, wherein said alkyl- or alkyl derivative-substituted aromatic compound of formula (B-1) optionally has at least one hydrogen atom replaced with a polar group at a ratio of not more than ⅓ relative to all hydrogen atoms of said alkyl- or alkyl derivative-substituted aromatic compound of formula (B-1), said polar group being selected from the group consisting of a chlorine atom, an unsubstituted or substituted amino group, an acyl group, an acyloxy group, a carboalkoxy group and a nitrile group.

3. The lubricant oil composition according to claim 2, wherein p and p' of formula (A-1) are 0 and 1, respectively, so that said n-valent aromatic group represented by R of formula (A) is represented by the formula:

$$Ar_1 \text{-}(Y'\text{-})_{l'}(Ar_4)_{m'} \quad (A\text{-}1a)$$

wherein $Ar_1$, $Ar_4$, Y', l' and m' are as defined for formula (A-1).

4. The lubricant oil composition according to claim 3, wherein each of l' and m' of formula (A-1a) is 1, so that said n-valent aromatic group represented by R of formula (A) is represented by the formula:

$$Ar_1\text{—}Y'\text{—}Ar_4 \quad (A\text{-}1b)$$

wherein $Ar_1$, $Ar_4$ and Y' are as defined for formula (A-1).

5. The lubricant oil composition according to claim 4, wherein said linkage group Y' of formula (A-1b) is a single bond, or a bivalent group selected from the group consisting of an oxygen atom (—O—), a sulfonyl group, a carbonyl group and an alkylene group having from 1 to 20 carbon atoms.

6. The lubricant oil composition according to claim 1, wherein said fluorine-containing aromatic compound (A) is represented by the formula:

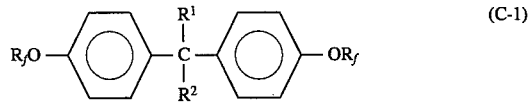

(C-1)

wherein each of $R^1$ and $R^2$ independently represents a hydrogen atom or an alkyl group having from 1 to 19 carbon atoms, wherein the total number of carbon atoms in $R^1$ and $R^2$ is from 4 to 19, and each $R_f$ is as defined for formula (A), wherein the $R_f$ groups are the same or different.

7. The lubricant oil composition according to claim 2, wherein p' of formula (A-1) is 0, so that said n-valent aromatic group represented by R of formula (A) is $Ar_1$ of formula (A-1), wherein $Ar_1$ is an aromatic nucleus substituted with at least one alkyl group having from 1 to 30 carbon atoms.

8. The lubricant oil composition according to claim 1, wherein said fluorine-containing aromatic compound (A) is represented by the formula:

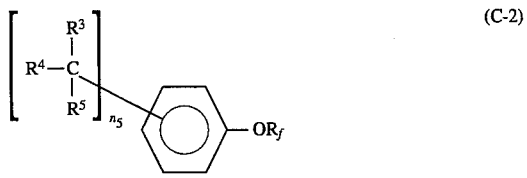

(C-2)

wherein each of $R^3$, $R^4$ and $R^5$ independently represents an alkyl group having from 1 to 20 carbon atoms, $n_5$ is an integer of from 1 to 3, the $R_f$ group is as defined for formula (A), wherein when $n_5$ is an integer of 2 or 3, the $R^3R^4R^5C$— groups are the same or different, and wherein the total number of carbon atoms of all $R^3R^4R^5C$— groups is from 4 to 25.

9. The lubricant oil composition according to claim 1, wherein said fluorine-containing aromatic compound (A) is represented by the formula:

(C-3)

wherein each of $R^6$, $R^7$ and $R^8$ independently represents an alkyl group having from 1 to 20 carbon atoms, and the $R_f$ group is as defined for formula (A), wherein the total number of carbon atoms of the $R^6R^7R^8C$— group is from 5 to 25.

10. The lubricant oil composition according to claim 1, wherein said $R_f$ of formula (A) is selected from the group consisting of a fluoroalkyl and a fluoroalkenyl group, each having from 1 to 10 carbon atoms.

11. The lubricant oil composition according to claim 1, wherein said $R_f$ of formula (A) is a fluoroalkyl group having from 2 to 25 carbon atoms and having in a main chain thereof 1 to 7 ether linkages.

12. The lubricant oil composition according to claim 2, wherein said $R_f$ of formula (A) represented by formula (A-2) is substituted with from 1 to 4 chlorine atoms.

13. The lubricant oil composition according to claim 1, wherein said $R_f$ of formula (A) is selected from the group consisting of an unsubstituted fluoroalkyl group having from 1 to 3 carbon atoms, —CF=CFCF$_3$, —CF$_2$CFClH, —CF=CFCl, and —CF$_2$CHFO–(C$_3$F$_6$O–)$_n$CF$_2$CF$_2$CF$_3$, wherein n is an integer of from 0 to 6.

14. The lubricant oil composition according to claim 1, wherein X of formula (A) is an oxygen atom.

15. The lubricant oil composition according to claim 2, wherein said alkyl- or alkyl derivative-substituted aromatic compound is represented by formula (B-1), wherein $n_4$ is zero.

16. The lubricant oil composition according to claim 15, wherein said alkyl- or alkyl derivative-substituted aromatic compound is benzene substituted with at least one branched alkyl group having from 3 to 30 carbon atoms.

17. A refrigerant composition comprising the lubricant oil composition according to any one of claims 1 to 16, and at least one refrigerant selected from the group consisting of a hydrofluorocarbon and a hydrofluoroether, wherein the weight ratio of said lubricant oil composition to said at least one refrigerant is 99/1 to 1/99.

18. The refrigerant composition according to claim 17, wherein said hydrofluorocarbon refrigerant has from 1 to 4 carbon atoms.

19. The refrigerant composition according to claim 18, wherein said hydrofluorocarbon refrigerant is at least one member selected from the group consisting of HFC-134a, HFC-143a, HFC-125 and HFC-32.

20. The refrigerant composition according to claim 19, wherein said hydrofluorocarbon refrigerant is HFC-134a.

21. The refrigerant composition according to claim 17, wherein the sum of the number of carbon atoms and the number of oxygen atoms of said hydrofluoroether is from 3 to 6.

22. A fluorine-containing aromatic compound represented by the formula:

(C-1)

wherein:
each of $R^1$ and $R^2$ independently represents a hydrogen atom or an alkyl group having from 1 to 19 carbon atoms, wherein the total number of carbon atoms in $R^1$ and $R^2$ is from 4 to 19; and
each $R_f$ is an unsubstituted or partially substituted fluorocarbon group having from 1 to 25 carbon atoms in which the ratio of fluorine atom or atoms to carbon atom or atoms is from 0.6 to 3, wherein said unsubstituted fluorocarbon group is selected from the group consisting of a fluoroalkyl group, a fluoroalkenyl group, a fluoroaryl group, a fluoroalkylaryl and a fluoroaralkyl group, in which each of the alkyl, alkenyl, aryl, alkylaryl and aralkyl groups is partially or entirely substituted with at least one fluorine atom, and said partially substituted fluorocarbon group has at least one substituent other than fluorine and hydrogen atoms in an amount such that the ratio of said at least one substituent to the total number of fluorine and hydrogen atoms of said partially substituted fluorocarbon group is not greater than 1.5, and wherein a main chain of said unsubstituted or partially substituted fluorocarbon group optionally has from 1 to 7 ether linkages;

wherein the $R_f$ groups are the same or different.

23. The fluorine-containing aromatic compound according to claim 22, wherein said $R_f$ is selected from the group consisting of a fluoroalkyl and a fluoroalkenyl group each having from 1 to 10 carbon atoms.

24. The fluorine-containing aromatic compound according to claim 22, wherein said $R_f$ is a fluoroalkyl group having from 2 to 25 carbon atoms and having in a main chain thereof 1 to 7 ether linkages.

25. The fluorine-containing aromatic compound according to claim 22, wherein said $R_f$ is substituted with from 1 to 4 chlorine atoms.

26. The fluorine-containing aromatic compound according to claim 22, wherein said $R_f$ is selected from the group consisting of an unsubstituted fluoroalkyl group having from 1 to 3 carbon atoms, —CF=CFCF$_3$, —CF$_2$CFClH, —CF=CFCl, and —CF$_2$CHFO—(C$_3$F$_6$O—)$_n$CF$_2$CF$_2$CF$_3$, wherein n is an integer of from 0 to 6.

27. A fluorine-containing aromatic compound represented by the formula:

(C-3)

wherein each of R$^6$, R$^7$ and R$^8$ independently represents an alkyl group having from 1 to 20 carbon atoms, wherein the total number of carbon atoms of the R$^6$R$^7$R$^8$C— group is from 5 to 25, and the $R_f$ group is an unsubstituted or partially substituted fluorocarbon group having from 1 to 25 carbon atoms in which the ratio of fluorine atom or atoms to carbon atom or atoms is from 0.6 to 3, wherein said unsubstituted fluorocarbon group is selected from the group consisting of a fluoroalkyl group, a fluoroalkenyl group, a fluoroaryl group, a fluoroalkylaryl and a fluoroaralkyl group, in which each of the alkyl, alkenyl, aryl, alkylaryl and aralkyl groups is partially or entirely substituted with at least one fluorine atom, and said partially substituted fluorocarbon group has at least one substituent other than fluorine and hydrogen atoms in an amount such that the ratio of said at least one substituent to the total number of fluorine and hydrogen atoms of said partially substituted fluorocarbon group is not greater than 1.5, and wherein a main chain of said unsubstituted or partially substituted fluorocarbon group optionally has from 1 to 7 ether linkages.

28. The fluorine-containing aromatic compound according to claim 27, wherein said $R_f$ is selected from the group consisting of a fluoroalkyl and a fluoroalkenyl group each having from 1 to 10 carbon atoms.

29. The fluorine-containing aromatic compound according to claim 27, wherein said $R_f$ is a fluoroalkyl group having from 2 to 25 carbon atoms and having in a main chain thereof 1 to 7 ether linkages.

30. The fluorine-containing aromatic compound according to claim 27, wherein said $R_f$ is substituted with from 1 to 4 chlorine atoms.

31. The fluorine-containing aromatic compound according to claim 27, wherein said $R_f$ is selected from the group consisting of an unsubstituted fluoroalkyl group having from 1 to 3 carbon atoms, —CF=CFCF$_3$, —CF$_2$CFClH, —CF=CFCl, and —CF$_2$CHFO—(C$_3$F$_6$O—)$_n$CF$_2$CF$_2$CF$_3$, wherein n is an integer of from 0 to 6.

32. The lubricant oil composition according to claim 4, wherein said linkage group Y' of formula (A-1b) is a methylene group or an alkylene group having from 2 to 20 carbon atoms, and each of Ar$_1$ and Ar$_4$ is independently an unsubstituted or substituted benzene nucleus, wherein the substituent of a benzene nucleus is an alkyl group having from 1 to 30 carbon atoms.

33. The lubricant oil composition according to claim 1, wherein said fluorine-containing aromatic compound (A) is represented by the formula:

(A')

wherein R' is a bivalent aromatic group represented by the formula:

(A-1c)

wherein Ar$_1$ and Ar$_4$ are as defined for formula (A-1), and Y' is a single bond, or a bivalent group selected from the group consisting of an oxygen atom (—O—), a sulfonyl group, a carbonyl group and an alkylene group having from 1 to 20 carbon atoms.

34. The lubricant oil composition according to claim 1, wherein said fluorine-containing aromatic compound (A) is represented by the formula:

(A")

wherein R" is a bivalent aromatic group represented by the formula:

(A-1d)

wherein Y' is a methylene group or an alkylene group having from 2 to 20 carbon atoms, and each of Ar$_1$ and Ar$_4$ is independently an unsubstituted or substituted benzene nucleus, wherein the substituent of a benzene nucleus is an alkyl group having from 1 to 30 carbon atoms.

* * * * *